(12) United States Patent
Parham et al.

(10) Patent No.: US 10,407,394 B2
(45) Date of Patent: Sep. 10, 2019

(54) TRIARYLAMINE-SUBSTITUTED BENZO[H]QUINOLINE-DERIVATIVES AS MATERIALS FOR ELECTRONIC DEVICES

(71) Applicant: Merck Patent GmbH, Darmstadt (DE)

(72) Inventors: Amir Hossain Parham, Frankfurt am Main (DE); Philipp Stoessel, Frankfurt am Main (DE); Thomas Eberle, Landau (DE); Anja Jatsch, Frankfurt am Main (DE); Jonas Valentin Kroeber, Frankfurt am Main (DE); Christof Pflumm, Darmstadt (DE); Irina Martynova, Griesheim (DE); Frank Voges, Bad Duerkheim (DE); Frank Stieber, Einhausen (DE)

(73) Assignee: Merck Patent GmbH, Darmstadt (DE)

( * ) Notice: Subject to any disclaimer, the term of this patent is extended or adjusted under 35 U.S.C. 154(b) by 332 days.

(21) Appl. No.: 15/026,650

(22) PCT Filed: Sep. 5, 2014

(86) PCT No.: PCT/EP2014/002416
§ 371 (c)(1),
(2) Date: Apr. 1, 2016

(87) PCT Pub. No.: WO2015/049022
PCT Pub. Date: Apr. 9, 2015

(65) Prior Publication Data
US 2016/0214942 A1   Jul. 28, 2016

(30) Foreign Application Priority Data
Oct. 4, 2013   (EP) .................................... 13004785

(51) Int. Cl.
| | | |
|---|---|---|
| C07D 221/10 | (2006.01) |
| C07D 401/14 | (2006.01) |
| C07D 405/14 | (2006.01) |
| C07D 401/04 | (2006.01) |
| C07D 401/10 | (2006.01) |
| C07D 401/12 | (2006.01) |
| C07D 405/10 | (2006.01) |
| C07D 405/12 | (2006.01) |
| C07D 409/14 | (2006.01) |
| C07D 413/04 | (2006.01) |
| C07D 417/04 | (2006.01) |
| C07D 471/04 | (2006.01) |
| C07D 487/04 | (2006.01) |
| C07D 405/04 | (2006.01) |
| C07D 409/12 | (2006.01) |
| C09K 11/06 | (2006.01) |
| H01L 51/00 | (2006.01) |
| C09K 11/02 | (2006.01) |
| H01L 51/50 | (2006.01) |

(52) U.S. Cl.
CPC ......... *C07D 221/10* (2013.01); *C07D 401/04* (2013.01); *C07D 401/10* (2013.01); *C07D 401/12* (2013.01); *C07D 401/14* (2013.01); *C07D 405/04* (2013.01); *C07D 405/10* (2013.01); *C07D 405/12* (2013.01); *C07D 405/14* (2013.01); *C07D 409/12* (2013.01); *C07D 409/14* (2013.01); *C07D 413/04* (2013.01); *C07D 417/04* (2013.01); *C07D 471/04* (2013.01); *C07D 487/04* (2013.01); *C09K 11/025* (2013.01); *C09K 11/06* (2013.01); *H01L 51/006* (2013.01); *H01L 51/0052* (2013.01); *H01L 51/0059* (2013.01); *H01L 51/0061* (2013.01); *H01L 51/0072* (2013.01); *H01L 51/0073* (2013.01); *H01L 51/0074* (2013.01); *C09K 2211/1011* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *C09K 2211/1092* (2013.01); *C09K 2211/185* (2013.01); *H01L 51/0067* (2013.01); *H01L 51/0085* (2013.01); *H01L 51/5016* (2013.01); *H01L 51/5056* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 8,318,325 | B2 | 11/2012 | Lee et al. |
| 8,974,921 | B2 | 3/2015 | Lee et al. |
| 9,627,626 | B2 | 4/2017 | Stoessel et al. |

(Continued)

FOREIGN PATENT DOCUMENTS

| | | | |
|---|---|---|---|
| JP | 2003282270 A | | 10/2003 |
| JP | 2007189001 A | * | 7/2007 |

(Continued)

OTHER PUBLICATIONS

Machine translation of JP 2009246097 A.*

(Continued)

*Primary Examiner* — Eli S Mekhlin
*Assistant Examiner* — William E McClain
(74) *Attorney, Agent, or Firm* — Drinker Biddle & Reath LLP

(57) ABSTRACT

The invention relates to a heteroaryl compound according to formula (I) and to the use thereof in electronic devices.

15 Claims, No Drawings

(56) References Cited

U.S. PATENT DOCUMENTS

| | | | | |
|---|---|---|---|---|
| 2011/0156017 A1* | 6/2011 | Lee | ............... | C07C 15/28 257/40 |
| 2013/0292653 A1* | 11/2013 | Park | ............... | C07D 221/08 257/40 |
| 2014/0326960 A1* | 11/2014 | Kim | ............... | H01L 51/0067 257/40 |
| 2014/0332758 A1* | 11/2014 | Kwong | ............... | H01L 51/0061 257/40 |
| 2016/0315270 A1 | 10/2016 | Seo et al. | | |

FOREIGN PATENT DOCUMENTS

| | | | |
|---|---|---|---|
| JP | 2009246097 A | * | 10/2009 |
| JP | 2013001707 A | | 1/2013 |
| JP | 2013065842 A | | 4/2013 |
| KR | 20120117693 A | * | 10/2012 |
| WO | WO-2008031743 A1 | | 3/2008 |
| WO | WO-2010036036 A2 | | 4/2010 |
| WO | WO-201295143 A1 | | 7/2012 |

OTHER PUBLICATIONS

Machine translation of JP 2003282270 A.*
Oi, et al. "Ruthenium complex-catalyzed direct ortho arylation and alkenylation of 2-arylpyridines with organic halides." Organic letters 3.16 (2001): 2579-2581.*
Machine translation of KR-20120117693-A.*
Machine Translation of JP-2007189001-A.*
International Search Report for PCT/EP2014/002416 dated Oct. 15, 2014.

* cited by examiner

TRIARYLAMINE-SUBSTITUTED BENZO[H]QUINOLINE-DERIVATIVES AS MATERIALS FOR ELECTRONIC DEVICES

CROSS-REFERENCE TO RELATED APPLICATIONS

This application is a national stage application (under 35 U.S.C. § 371) of PCT/EP2014/002416, filed Sep. 5, 2014, which claims benefit of European Application No. 13004785.5, filed Oct. 4, 2013, both applications of which are incorporated herein by reference in their entirety.

The present application relates to heteroaromatic analogs of phenanthroline according to a formula (I) defined below. The compounds are suitable, inter alia, as functional materials in electronic devices, especially in organic electroluminescent devices (OLEDs).

BACKGROUND OF THE INVENTION

Electronic devices in the context of this application are understood to mean what are called organic electronic devices, which contain organic compounds as functional materials. More particularly, these are understood to mean OLEDs.

The structure of OLEDs in which organic compounds are used as functional materials is described, for example, in U.S. Pat. Nos. 4,539,507, 5,151,629, EP 0676461 and WO 98/27136. In general, the term OLEDs is understood to mean electronic devices which have one or more layers comprising organic compounds and emit light on application of electrical voltage.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by layers having a hole-transporting function, for example hole-injecting layers, hole transport layers, electron blocker layers and emitting layers. For use in these layers, there is a continuous search for novel materials having hole-transporting properties, for example hole injection materials, hole transport materials, electron blocker materials and matrix materials, for use in combination with emitter materials, especially phosphorescent emitter materials.

For this purpose, the prior art describes, inter alia, mono-triarylamines (cf. JP 1995/053955, WO 2006/123667 and JP 2010/222268) and bisfunctional or higher-functionality amines (cf. U.S. Pat. No. 7,504,163 and US 2005/0184657). Additionally known for this purpose are carbazole compounds, for example biscarbazolylbiphenyl (CBP) and the compounds described in WO 2008/086851, US 2005/0221124 A1, EP 2202818 A1 and WO 2013/060418. Additionally known for this purpose are bridged triarylamine compounds, as described, for example, in WO 2007/031165, WO 2010/083871, WO 2011/088877, WO 2011/107186 and WO 2011/128017.

However, there is an unchanged need for alternative compounds for this use.

DETAILED DESCRIPTION OF THE INVENTION

It has now been found that arylamines, bridged arylamines and carbazole derivatives which are characterized in that they have a benzo[h]quinoline unit are of outstanding suitability for use in OLEDs.

These compounds preferably have one or more advantageous properties selected from very good hole-conducting properties and high thermal and oxidation stability. More particularly, the compounds have a HOMO of relatively high energy compared to other compounds of similar structure, and are therefore excellent hole conductors. In the case of use in OLEDs, the compounds preferably achieve a high lifetime and low operating voltage.

The present application thus provides compounds of the formula (I)

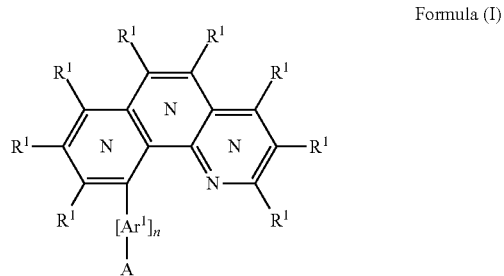

Formula (I)

where:
A is selected from groups of the formulae (A-1) and (A-2)

Formula (A-1)

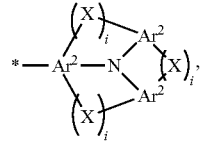

Formula (A-2)

which are bonded via the bond marked *, $Ar^1$ is the same or different at each instance and is an aromatic or heteroaromatic ring system which has 5 to 24 aromatic ring atoms and may be substituted by one or more $R^1$ radicals;

$Ar^2$ is the same or different at each instance and is an aromatic or heteroaromatic ring system which has 5 to 24 aromatic ring atoms and may be substituted by one or more $R^1$ radicals;

X is the same or different at each instance and is a single bond or a group selected from $BR^2$, $C(R^2)_2$, —$C(R^2)_2$—$C(R^2)_2$—, —$C(R^2)$=$C(R^2)$—, —$C(R^2)_2$—O—, —$C(R^2)_2$—$NR^2$—, $Si(R^2)_2$, C=O, $NR^2$, $PR^2$, $P(=O)R^2$, O, S, S=O and $SO_2$;

$R^1$, $R^2$ are the same or different at each instance and are H, D, F, C(=O)$R^3$, CN, $Si(R^3)_3$, $N(R^3)_2$, P(=O)($R^3$)$_2$, $OR^3$, S(=O)$R^3$, S(=O)$_2R^3$, a straight-chain alkyl or alkoxy group having 1 to 20 carbon atoms or a branched or cyclic alkyl or alkoxy group having 3 to 20 carbon atoms or an alkenyl or alkynyl group having 2 to 20 carbon atoms, where the abovementioned groups may each be substituted by one or more $R^3$ radicals and where one or more $CH_2$ groups in the abovementioned groups may be replaced by —$R^3$C=$CR^3$—, —C≡C—, $Si(R^3)_2$, C=O, C=$NR^3$, —C(=O)O—, —C(=O)$NR^3$—, $NR^3$, P(=O)($R^3$), —O—, —S—, SO or $SO_2$, or an aromatic or heteroaromatic ring system which has 5 to 30 aromatic ring atoms and may be substituted by one or more $R^3$ radicals; two or more $R^1$ or $R^2$ radicals may be joined to one another and form a ring;

$R^3$ is the same or different at each instance and is H, D, F, $C(=O)R^4$, CN, $Si(R^4)_3$, $N(R^4)_2$, $P(=O)(R^4)_2$, $OR^4$, $S(=O)R^4$, $S(=O)_2R^4$, a straight-chain alkyl or alkoxy group having 1 to 20 carbon atoms or a branched or cyclic alkyl or alkoxy group having 3 to 20 carbon atoms or an alkenyl or alkynyl group having 2 to 20 carbon atoms, where the abovementioned groups may each be substituted by one or more $R^4$ radicals and where one or more $CH_2$ groups in the abovementioned groups may be replaced by $—R^4C=CR^4—$, $—C≡C—$, $Si(R^4)_2$, $C=O$, $C=NR^4$, $—C(=O)O—$, $—C(=O)NR^4—$, $NR^4$, $P(=O)(R^4)$, $—O—$, $—S—$, SO or $SO_2$, or an aromatic or heteroaromatic ring system which has 5 to 30 aromatic ring atoms and may be substituted by one or more $R^4$ radicals; two or more $R^3$ radicals may be joined to one another and form a ring;

$R^4$ is the same or different at each instance and is H, D, F, CN or an aliphatic, aromatic or heteroaromatic organic radical having 1 to 20 carbon atoms, in which one or more hydrogen atoms may also be replaced by D, F or CN; two or more $R^4$ substituents may be joined to one another and form a ring:

n is 0, 1, 2 or 3;

i is the same or different at each instance and is 0 or 1; and in the benzene rings with an N drawn in the middle, one or more ring members $—CR^1=$ in each case may be replaced by $—N=$.

An aryl group in the context of this invention contains 6 to 60 aromatic ring atoms; a heteroaryl group in the context of this invention contains 5 to 60 aromatic ring atoms, at least one of which is a heteroatom. The heteroatoms are preferably selected from N, O and S. This is the fundamental definition. If other preferences are stated in the description of the present invention, for example with regard to the number of aromatic ring atoms or of heteroatoms present, these are applicable.

An aryl group or heteroaryl group is understood here to mean either a simple aromatic cycle, i.e. benzene, or a simple heteroaromatic cycle, for example pyridine, pyrimidine or thiophene, or a fused (annelated) aromatic or heteroaromatic polycycle, for example naphthalene, phenanthrene, quinoline or carbazole. A fused (annelated) aromatic or heteroaromatic polycycle, in the context of the present application, consists of two or more simple aromatic or heteroaromatic cycles fused to one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 60 carbon atoms in the ring system. A heteroaromatic ring system in the context of this invention contains 5 to 60 aromatic ring atoms, at least one of which is a heteroatom. The heteroatoms are preferably selected from N, O and/or S. An aromatic or heteroaromatic ring system in the context of this invention shall be understood to mean a system which does not necessarily contain only aryl or heteroaryl groups but in which it is also possible for a plurality of aryl or heteroaryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl or heteroaryl groups are joined to one another via single bonds are also to be regarded as aromatic or heteroaromatic ring systems in the context of this invention, for example systems such as biphenyl, terphenyl or diphenyltriazine.

An aromatic or heteroaromatic ring system which has 5-60 aromatic ring atoms and may also be substituted in each case by radicals as defined above and which may be joined to the aromatic or heteroaromatic system via any desired positions is especially understood to mean groups derived from the groups mentioned above under aryl and heteroaryl groups, and also from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole or combinations of these groups.

In the context of the present invention, a straight-chain alkyl group having 1 to 40 carbon atoms and a branched or cyclic alkyl group having 3 to 40 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals. An alkoxy or thioalkyl group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, the compound of the formula (I) does not comprise any further arylamino group, any further bridged arylamino group or any further carbazole group in addition to the A group. Bridged arylamino groups are understood to mean groups corresponding to groups of the formula (A-1) or (A-2) in which at least one X bridge which is not a single bond is present.

In addition, it is preferable that the compound of the formula (I) does not have any fused aryl or heteroaryl group having more than 14 aromatic ring atoms, more preferably any fused aryl or heteroaryl group having more than 10 aromatic ring atoms, as substituent $R^1$, $R^2$, $R^3$ and $R^4$.

For the compounds of formula (I), it is preferable that, in the benzene rings with an N drawn in the middle, no or exactly one or two ring members —$CR^1$= are replaced by —N=, more preferably none or exactly one and most preferably none.

In a preferred embodiment of the invention, exactly one or exactly two ring members —$CR^1$= in the middle one of the three benzene rings in formula (I) are replaced by —N=, and no ring member —$CR^1$= in the two outer rings is replaced by —N=.

In an alternative preferred embodiment of the invention, in all three benzene rings in formula (I) with an N drawn in the middle, no ring member —$CR^1$= is replaced by N.

It is preferable that n is 0, 1 or 2, more preferably 0 or 1, most preferably 0.

It is preferable that $Ar^1$ is the same or different at each instance and is an aromatic or heteroaromatic ring system which has 6 to 14 aromatic ring atoms and may be substituted by one or more $R^1$ radicals. More preferably, $Ar^1$ is the same or different at each instance and is selected from benzene, pyridine, pyrimidine, triazine, naphthalene, quinoline, fluorene, spirobifluorene, indenofluorene, carbazole, indenocarbazole, indolocarbazole, dibenzofuran and dibenzothiophene, each of which may be substituted by one or more $R^1$ radicals.

Most preferably, the —$(Ar^1)_n$— unit is the same or different at each instance and is selected from groups of the following formulae (L-1) to (L-18):

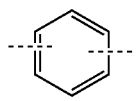

Formula (L-1)

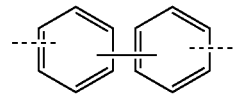

Formula (L-2)

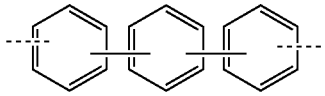

Formula (L-3)

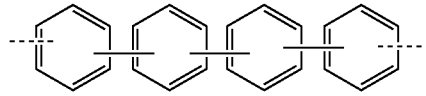

Formula (L-4)

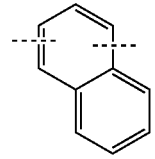

Formula (L-5)

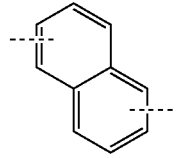

Formula (L-6)

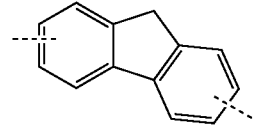

Formula (L-7)

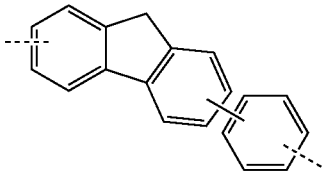

Formula (L-8)

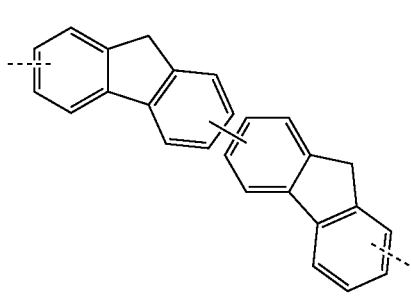

Formula (L-9)

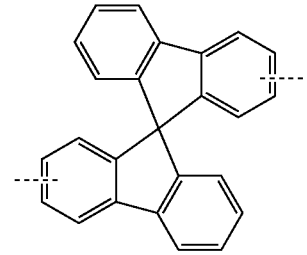

Formula (L-10)

-continued

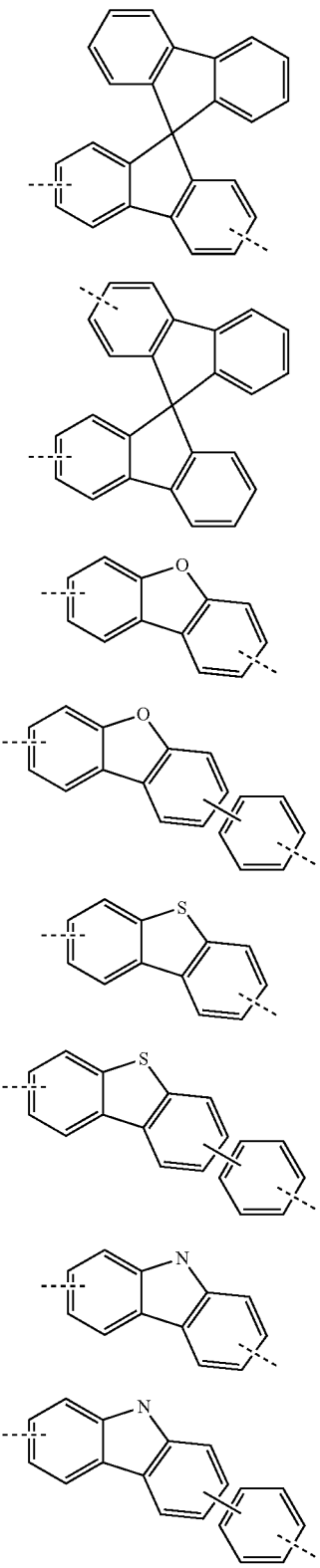

Formula (L-11)

Formula (L-12)

Formula (L-13)

Formula (L-14)

Formula (L-15)

Formula (L-16)

Formula (L-17)

Formula (L-18)

where the groups may each be substituted by $R^1$ radicals at the unoccupied positions and where the dashed lines indicate the bonds to the rest of the compound.

$R^1$ is preferably the same or different at each instance and is H, D, F, CN, $Si(R^3)_3$, $N(R^3)_2$, a straight-chain alkyl or alkoxy group having 1 to 20 carbon atoms or a branched or cyclic alkyl or alkoxy group having 3 to 20 carbon atoms, where the abovementioned groups may each be substituted by one or more $R^3$ radicals and where one or more $CH_2$ groups in the abovementioned groups may be replaced by —C≡C—, —$R^3$C=$CR^3$—, $Si(R^3)_2$, C=O, C=$NR^3$, —$NR^3$—, —O—, —S—, —C(=O)O— or —C(=O)$NR^3$—, or an aromatic or heteroaromatic ring system having 5 to 20 aromatic ring atoms, each of which may be substituted by one or more $R^3$ radicals, where two or more $R^1$ radicals may be joined to one another and may form a ring.

$R^2$ is preferably the same or different at each instance and is H, D, F, $Si(R^3)_3$, a straight-chain alkyl or alkoxy group having 1 to 20 carbon atoms or a branched or cyclic alkyl or alkoxy group having 3 to 20 carbon atoms, where the abovementioned groups may each be substituted by one or more $R^3$ radicals and where one or more $CH_2$ groups in the abovementioned groups may be replaced by —C≡C—, —$R^3$C=$CR^3$—, $Si(R^3)_2$, C=O, C=$NR^3$, —$NR^3$—, —O—, —S—, —C(=O)O— or —C(=O)$NR^3$—, or an aromatic or heteroaromatic ring system having 5 to 20 aromatic ring atoms, each of which may be substituted by one or more $R^3$ radicals, where two or more $R^2$ radicals may be joined to one another and may form a ring.

In a preferred embodiment, two $R^2$ groups which bind to the same atom of an X group, for example to the carbon atom of an X group which is $C(R^2)_2$, together form a ring. More preferably, in this case, they form a cycloalkyl ring, for example a cyclopentyl or cyclohexyl ring.

$R^3$ is preferably the same or different at each instance and is H, D, F, CN, $Si(R^4)_3$, $N(R^4)_2$, a straight-chain alkyl or alkoxy group having 1 to 20 carbon atoms or a branched or cyclic alkyl or alkoxy group having 3 to 20 carbon atoms, where the abovementioned groups may each be substituted by one or more $R^4$ radicals and where one or more $CH_2$ groups in the abovementioned groups may be replaced by —C≡C—, —$R^4$C=$CR^4$—, $Si(R^4)_2$, C=O, C=$NR^4$, —$NR^4$—, —O—, —S—, —C(=O)O— or —C(=O)$NR^4$—, or an aromatic or heteroaromatic ring system having 5 to 20 aromatic ring atoms, each of which may be substituted by one or more $R^4$ radicals, where two or more $R^3$ radicals may be joined to one another and may form a ring.

For groups of the formula (A-2), it is preferable that no, exactly one or exactly two indices i are 1, and the other indices i are 0.

In addition, it is preferable that not more than two X groups which are a single bond are present in one group of the formula (A-2).

It is preferable that X is the same or different at each instance and is selected from a single bond and a group selected from $C(R^2)_2$, —$C(R^2)_2$—$C(R^2)_2$—, —$C(R^2)$=C($R^2$)—, C=O, $NR^2$, O and S. Most preferably, X is the same or different at each instance and is selected from a single bond and a group selected from $C(R^2)_2$, C=O, $NR^2$, O and S.

It is preferable that $Ar^2$ is the same or different at each instance and is an aromatic or heteroaromatic ring system which has 6 to 24 aromatic ring atoms and may be substituted by one or more $R^1$ radicals. More preferably, $Ar^2$ is the same or different at each instance and is selected from benzene, biphenyl, terphenyl, quaterphenyl, pyridine, pyrimidine, pyrazine, pyridazine, triazine, naphthalene, quinoline, fluorene, spirobifluorene, indenofluorene, carbazole, indenocarbazole, indolocarbazole, dibenzofuran and dibenzothiophene, each of which may be substituted by one or more $R^1$ radicals. Most preferably, $Ar^2$ is the same or different at each instance and is selected from benzene, biphenyl, terphenyl, quaterphenyl, fluorene, spirobifluorene, indenofluorene, carbazole, indenocarbazole, indolocarbazole, dibenzofuran and dibenzothiophene, each of which may be substituted by one or more $R^1$ radicals.

Preferred embodiments of the groups of the formula (A-1) are the following formulae (A-1-1) to (A-1-30):

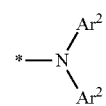

Formula (A-1-1)

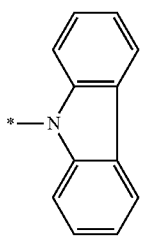

Formula (A-1-2)

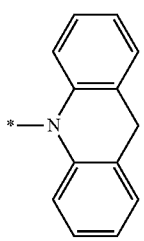

Formula (A-1-3)

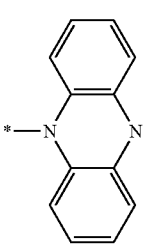

Formula (A-1-4)

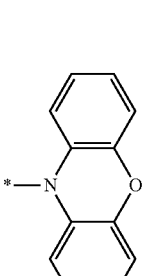

Formula (A-1-5)

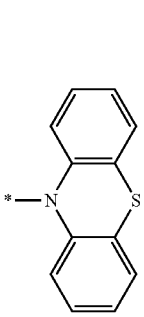

Formula (A-1-6)

-continued

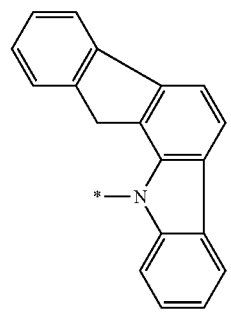

Formula (A-1-7)

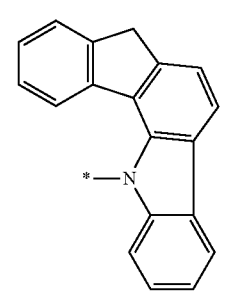

Formula (A-1-8)

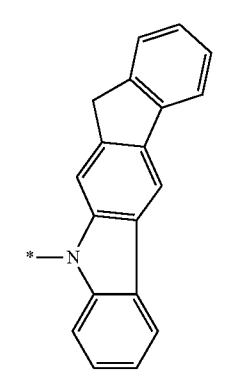

Formula (A-1-9)

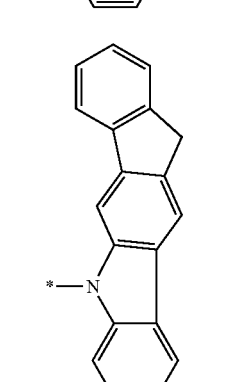

Formula (A-1-10)

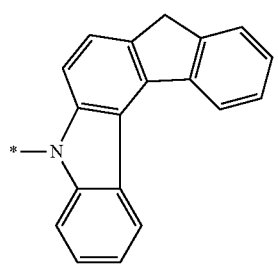

Formula (A-1-11)

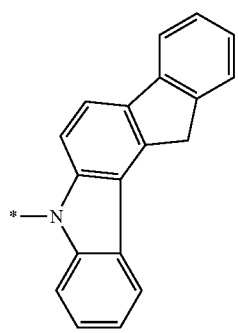
Formula (A-1-12)
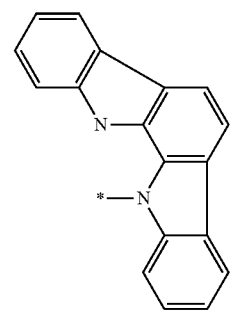
Formula (A-1-13)
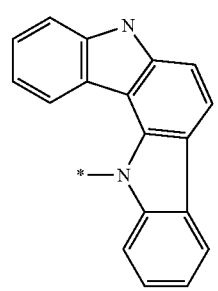
Formula (A-1-14)
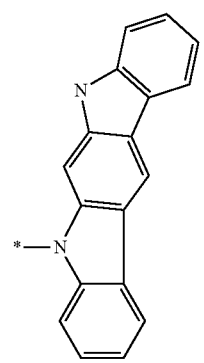
Formula (A-1-15)
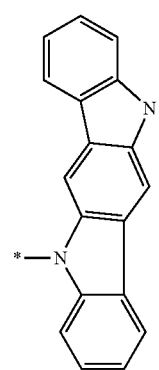
Formula (A-1-16)
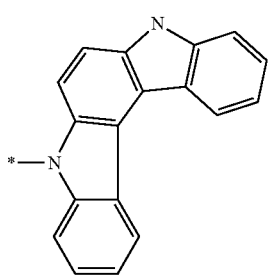
Formula (A-1-17)
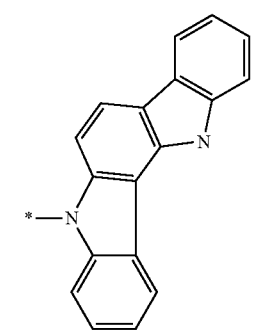
Formula (A-1-18)
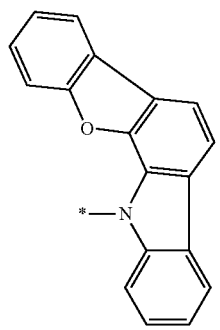
Formula (A-1-19)
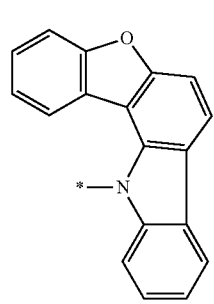
Formula (A-1-20)
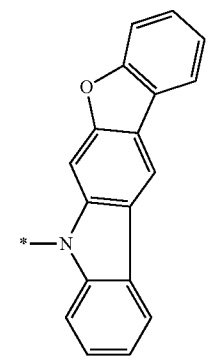
Formula (A-1-21)

Formula (A-1-22)
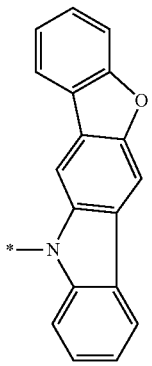

Formula (A-1-23)
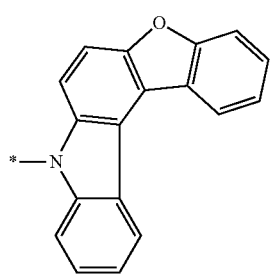

Formula (A-1-24)
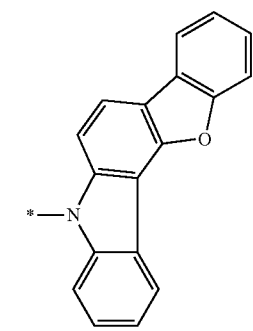

Formula (A-1-25)
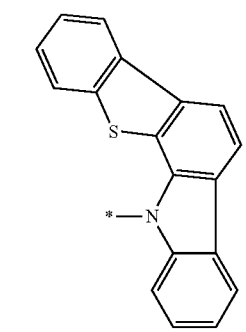

Formula (A-1-26)
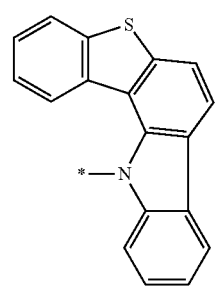

Formula (A-1-27)
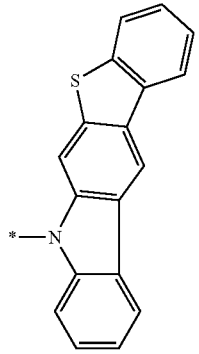

Formula (A-1-28)
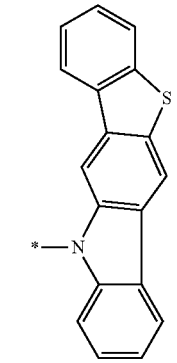

Formula (A-1-29)
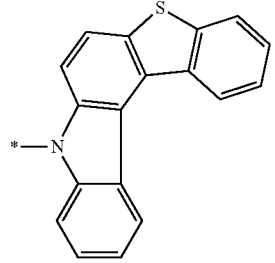

Formula (A-1-30)
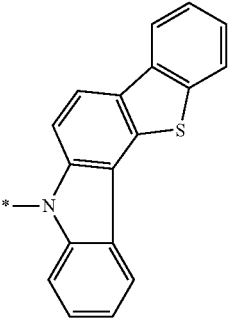

which may each be substituted by $R^1$ radicals at the unoccupied positions. For the formula (A-1-1), it is preferable that $Ar^2$ is the same or different at each instance and is selected from benzene, biphenyl, terphenyl, quaterphenyl, fluorene, spirobifluorene, indenofluorene, carbazole, indenocarbazole, indolocarbazole, dibenzofuran and dibenzothiophene, each of which may each be substituted by one or more $R^1$ radicals.

Preferred embodiments of the groups of the formula (A-2) are the following formulae (A-2-1) to (A-2-59):

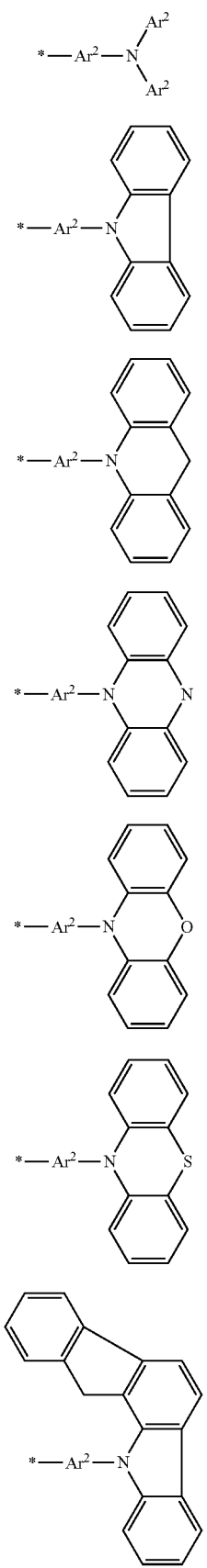
Formula (A-2-1)
Formula (A-2-2)
Formula (A-2-3)
Formula (A-2-4)
Formula (A-2-5)
Formula (A-2-6)
Formula (A-2-7)
-continued
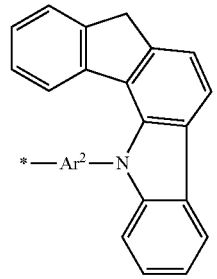
Formula (A-2-8)
Formula (A-2-9)
Formula (A-2-10)
Formula (A-2-11)
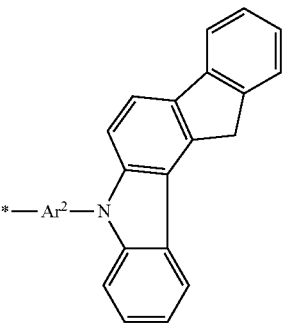
Formula (A-2-12)

Formula (A-2-13)
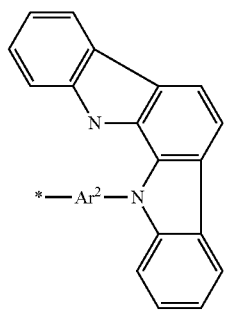
Formula (A-2-14)
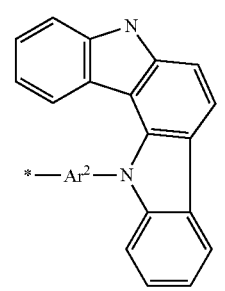
Formula (A-2-15)
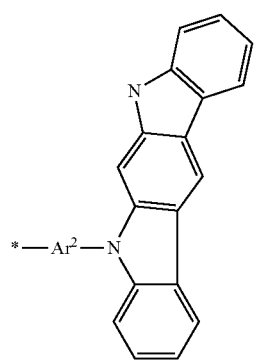
Formula (A-2-16)
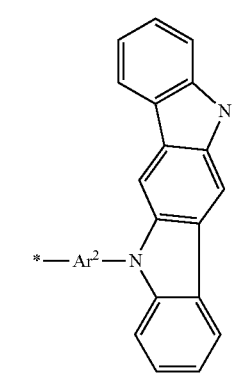
Formula (A-2-17)
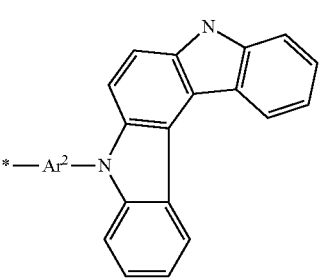
Formula (A-2-18)
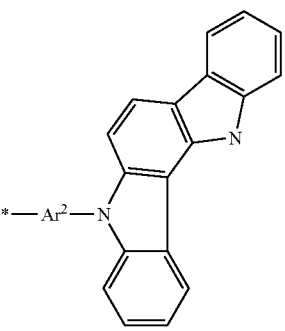
Formula (A-2-19)
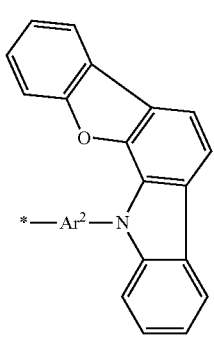
Formula (A-2-20)
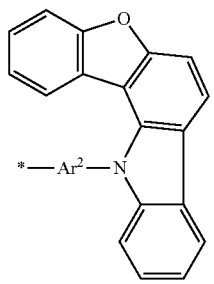
Formula (A-2-21)
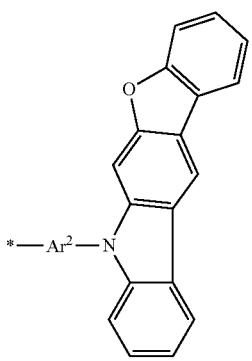

-continued
Formula (A-2-22)
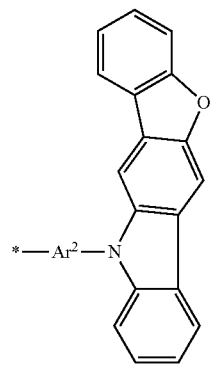
Formula (A-2-23)
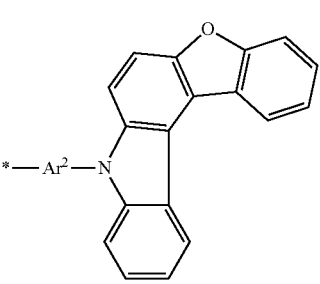
Formula (A-2-24)
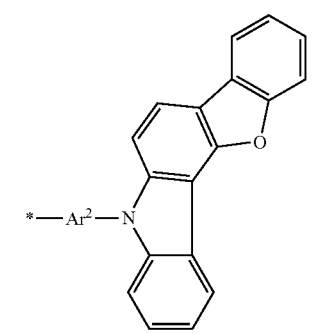
Formula (A-2-25)
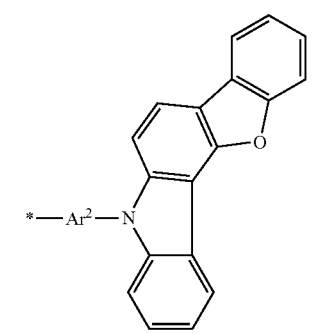
Formula (A-2-26)
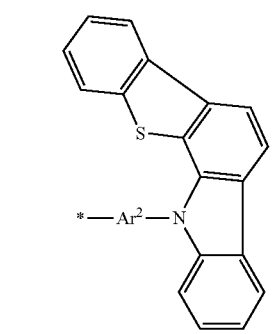
Formula (A-2-27)
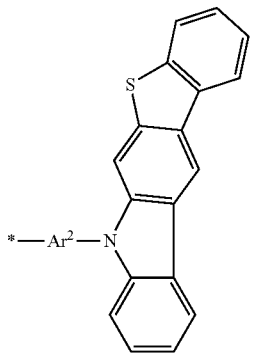
Formula (A-2-28)
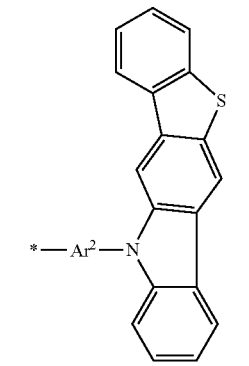
Formula (A-2-29)
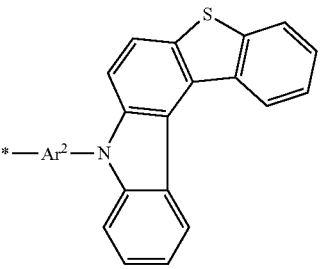
Formula (A-2-30)
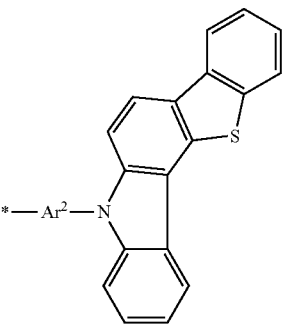
Formula (A-2-31)
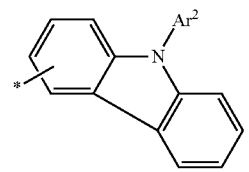

Formula (A-2-32)
Formula (A-2-33)
Formula (A-2-34)
Formula (A-2-35)
Formula (A-2-36)
Formula (A-2-37)
Formula (A-2-38)
Formula (A-2-39)
Formula (A-2-40)
Formula (A-2-41)
Formula (A-2-42)
Formula (A-2-43)
Formula (A-2-44)

Formula (A-2-45)
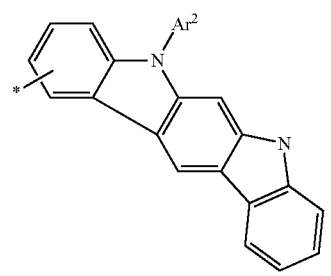
Formula (A-2-46)
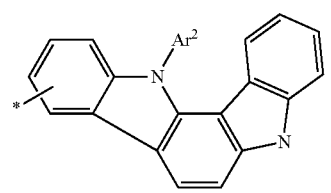
Formula (A-2-47)
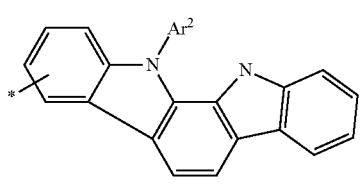
Formula (A-2-48)
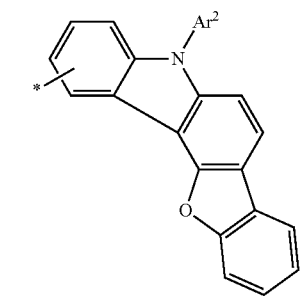
Formula (A-2-49)
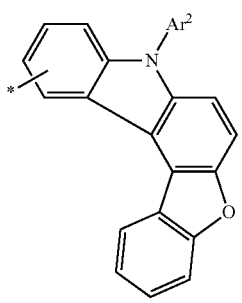
Formula (A-2-50)
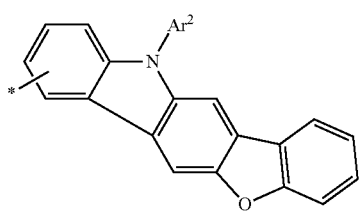
Formula (A-2-51)
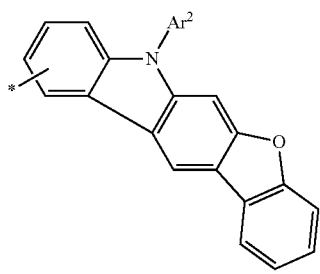
Formula (A-2-52)
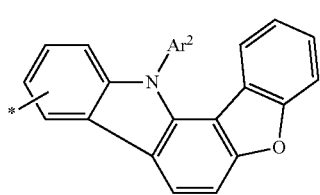
Formula (A-2-53)
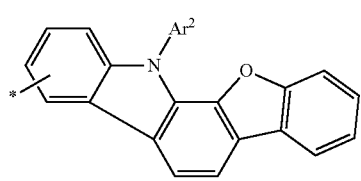
Formula (A-2-54)
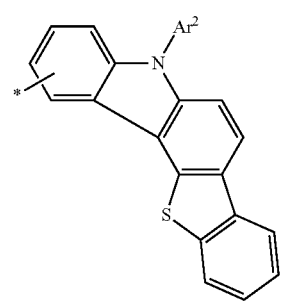
Formula (A-2-55)
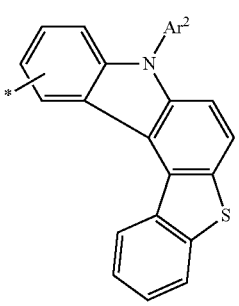
Formula (A-2-56)
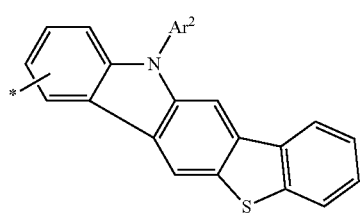

Formula (A-2-57)

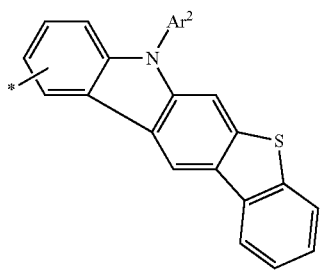

Formula (A-2-58)

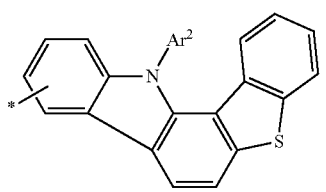

Formula (A-2-59)

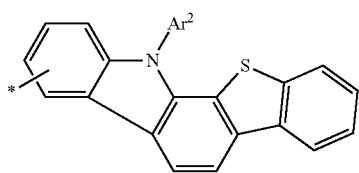

which may each be substituted by R¹ radicals at the unoccupied positions. For Ar², it is preferable that it is the same or different at each instance and is selected from benzene, biphenyl, terphenyl, quaterphenyl, fluorene, spirobifluorene, indenofluorene, carbazole, indenocarbazole, indolocarbazole, dibenzofuran and dibenzothiophene, each of which may be substituted by one or more R¹ radicals.

Preferred compounds of the formula (I) correspond to one of the formulae (I-1) to (I-3)

Formula (I-1)

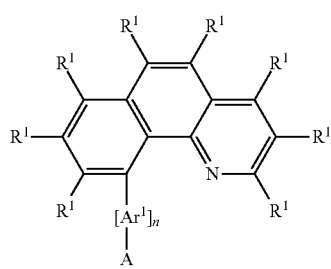

Formula (I-2)

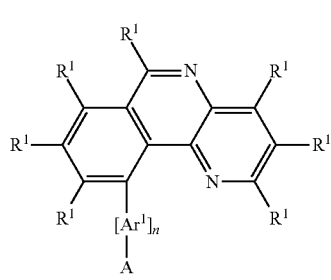

Formula (I-3)

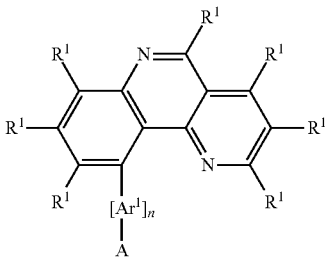

where the groups and indices that occur are as defined above. At the same time, preference is given to the above-detailed preferred embodiments of the groups and indices.

More particularly, it is preferable for formulae (I-1) to (I-3) that the A group is selected from the preferred embodiments of the groups of the formulae (A-1) and (A-2), especially from the groups of the formulae (I-1-1) to (I-1-30) and (I-2-1) to (I-2-59).

Once again, it is especially preferable for formulae (I-1) to (I-3) that the —[Ar¹]$_n$-unit is selected from the above-listed formulae (L-1) to (L-18).

Once again, it is especially preferable for formulae (I-1) to (I-3) that n is 0.

Among the formulae (I-1) to (I-3), particular preference is given to formula (I-1).

Examples of compounds of the formula (I) are listed below.

1

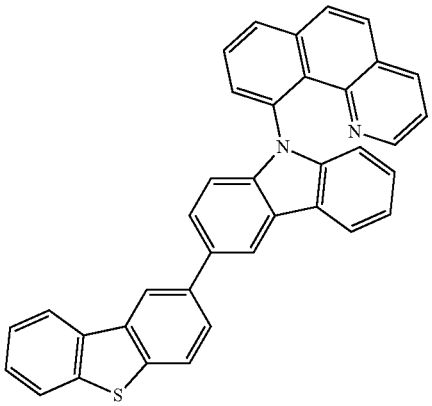

2

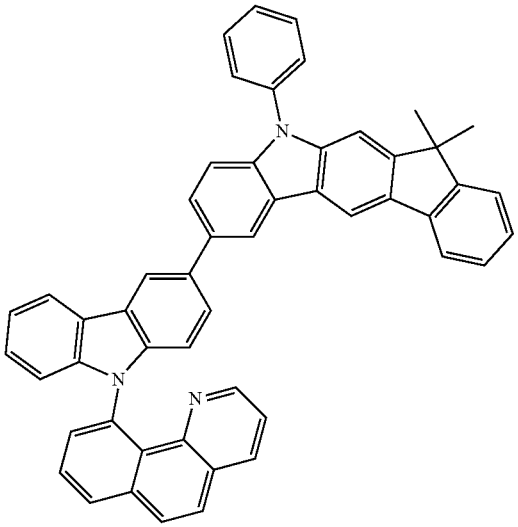

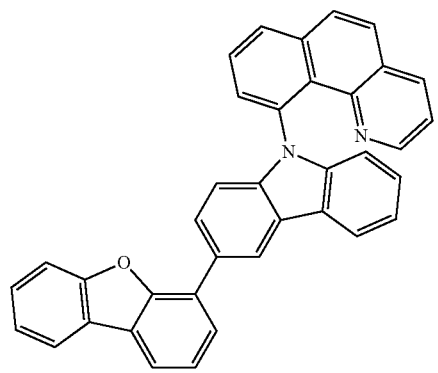
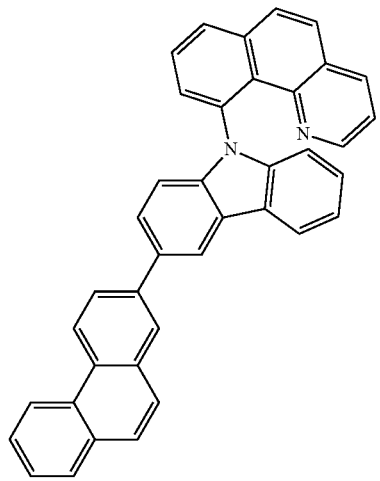
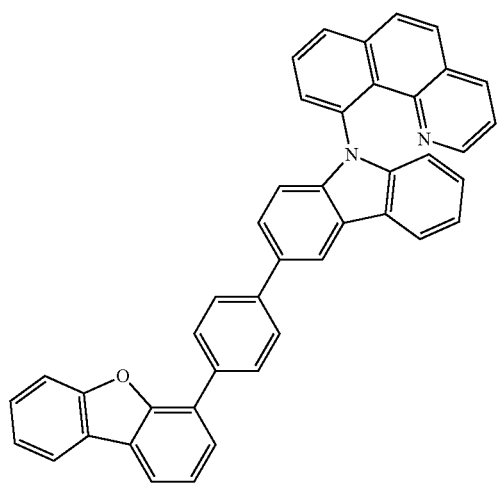
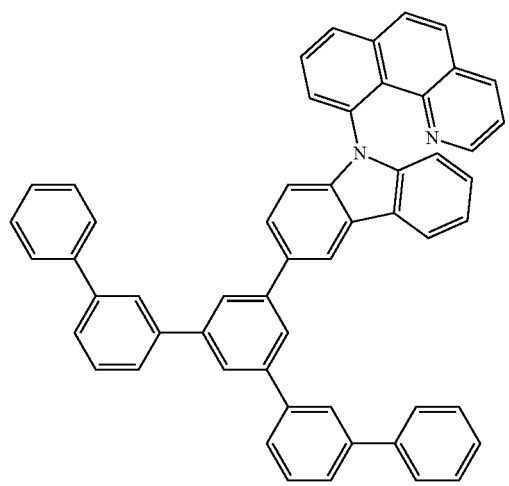
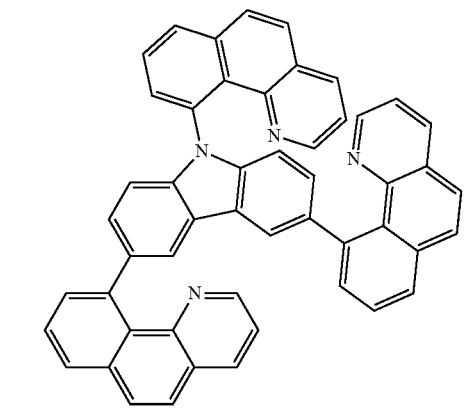
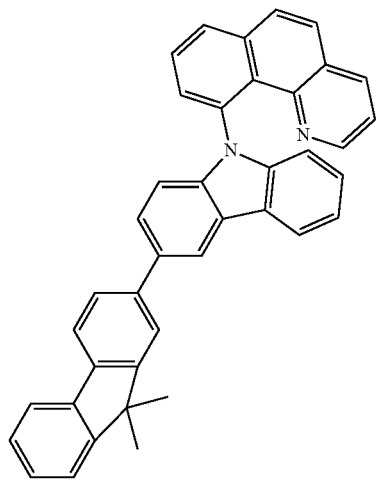

9
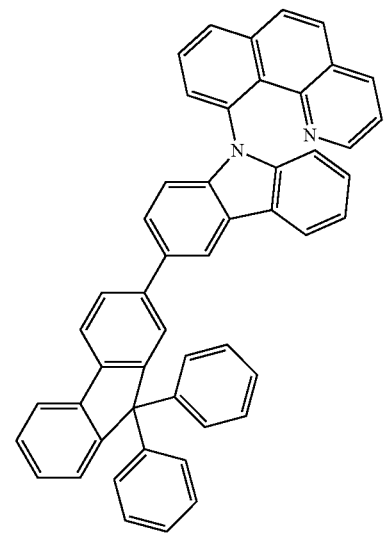
10
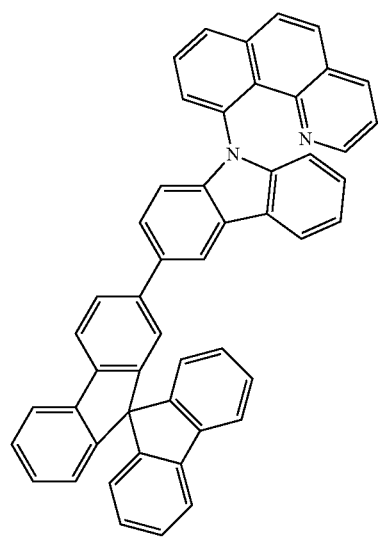
11
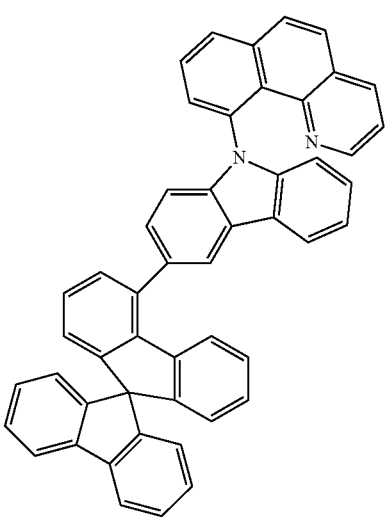
12
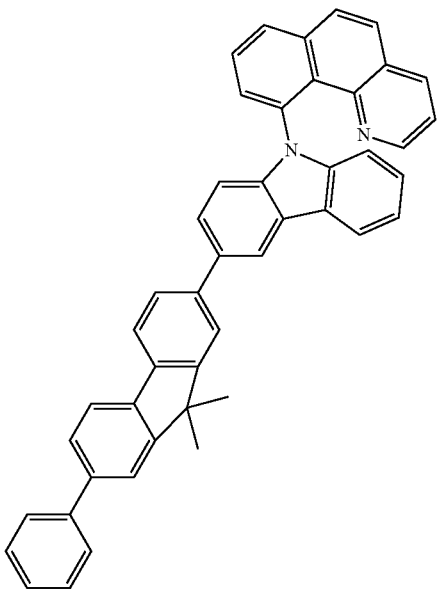
13
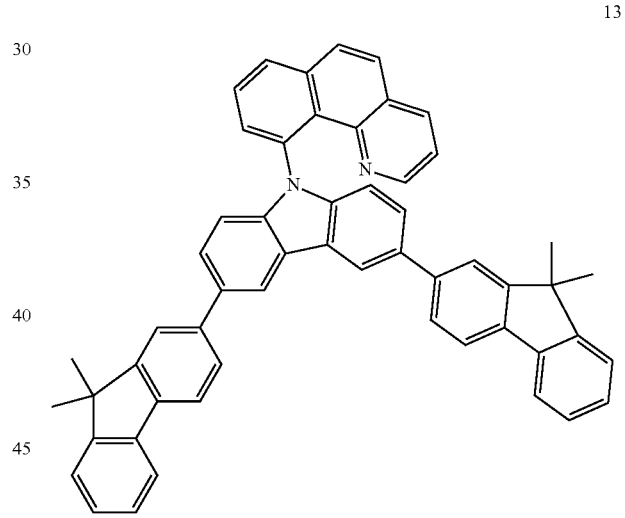
14
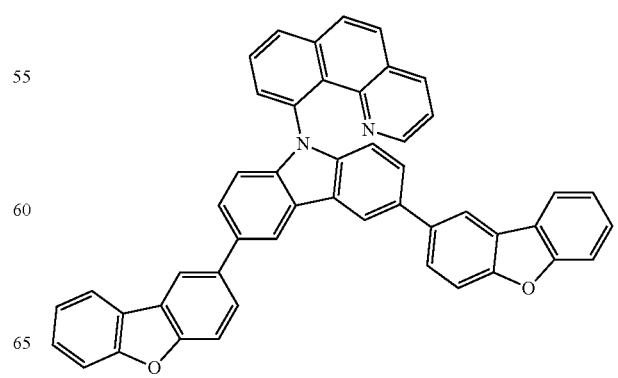

15
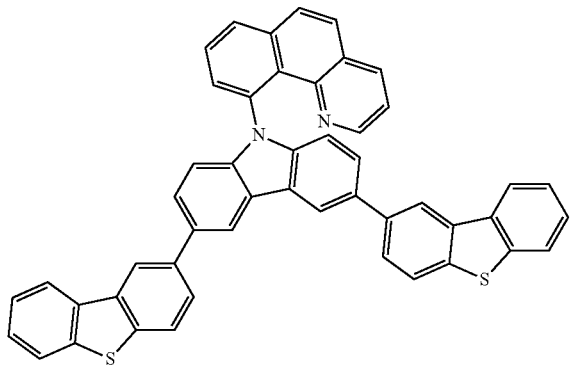
16
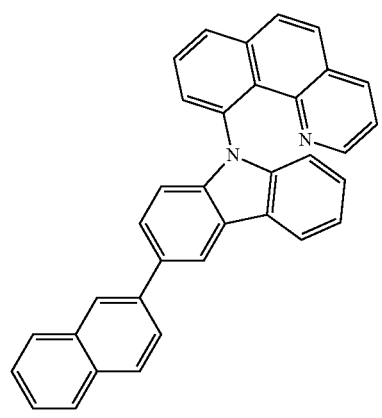
17
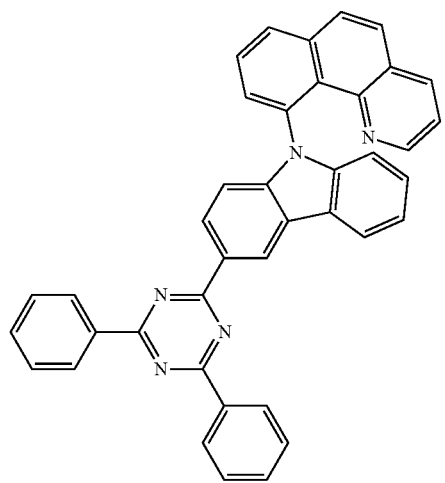
18
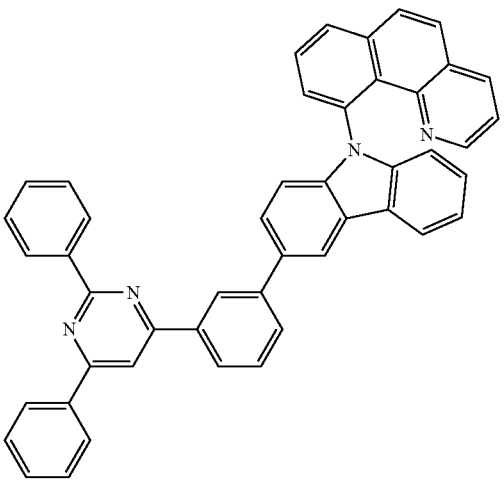
19
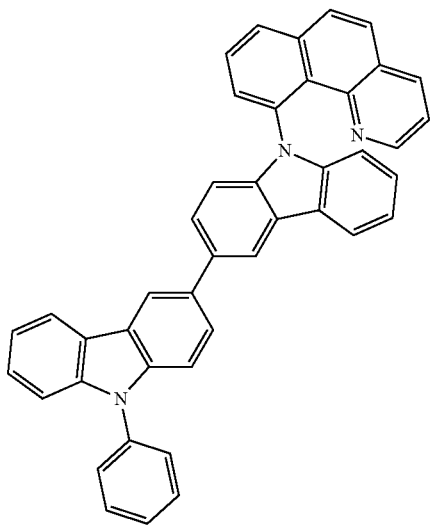
20
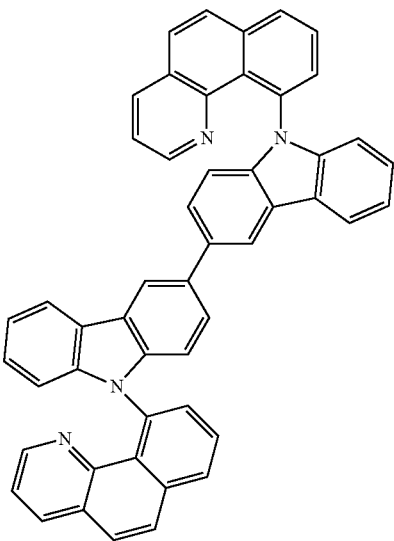

21
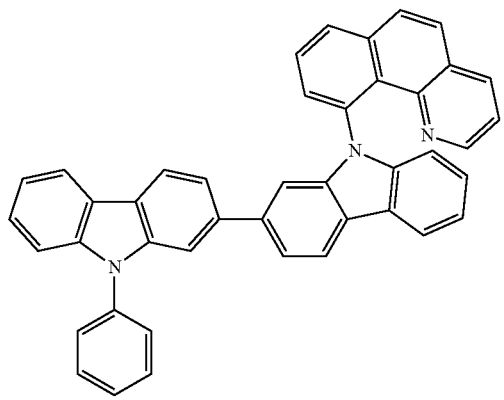
22
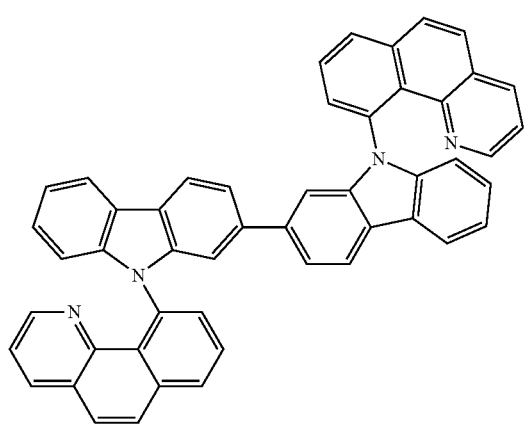
23
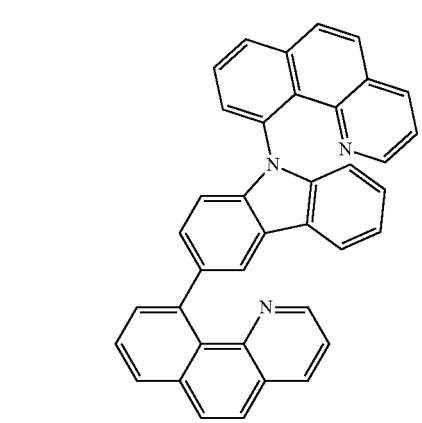
24
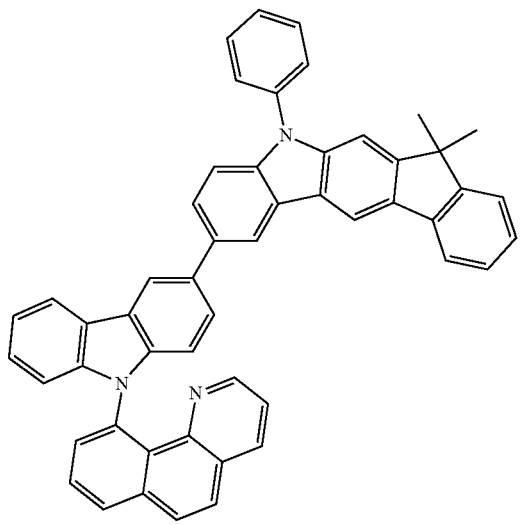
25
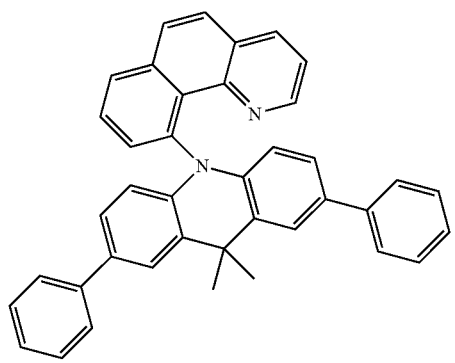
26
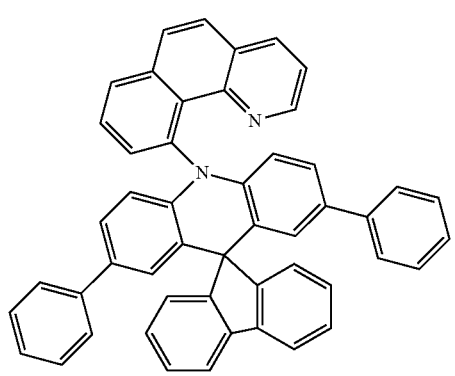
27
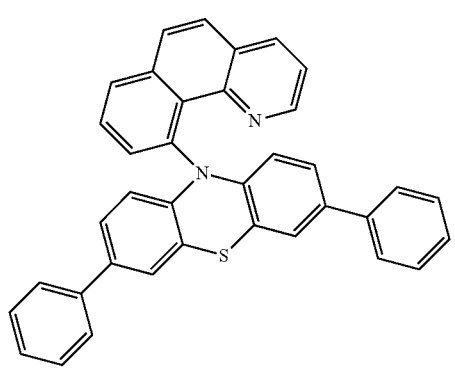

-continued
28
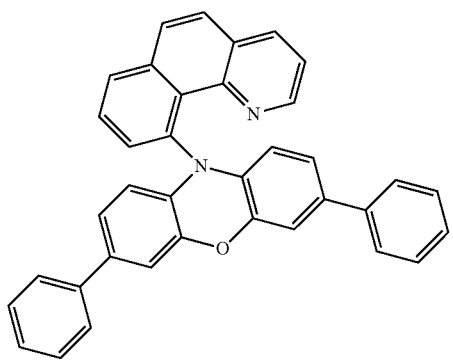
29
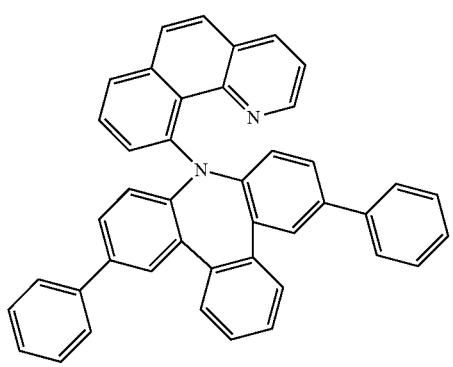
30
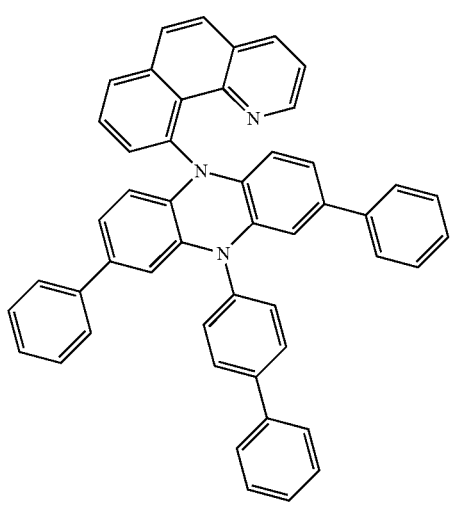
-continued
31
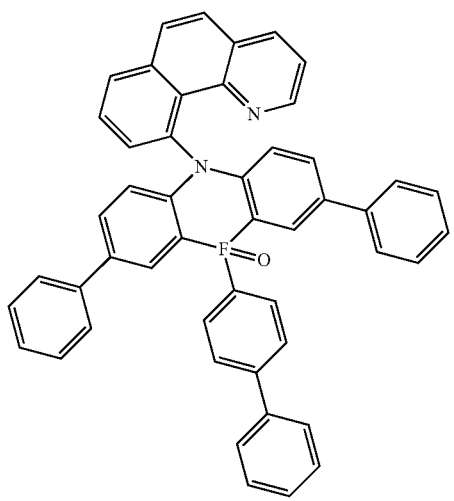
32
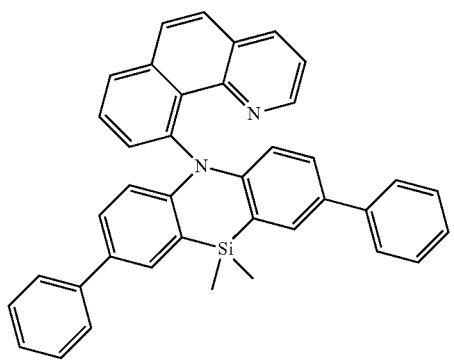
33
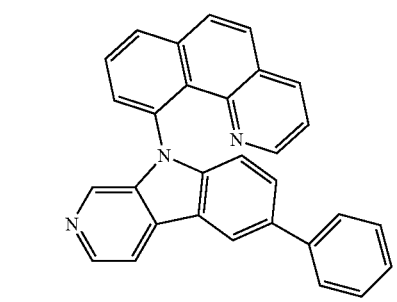
34
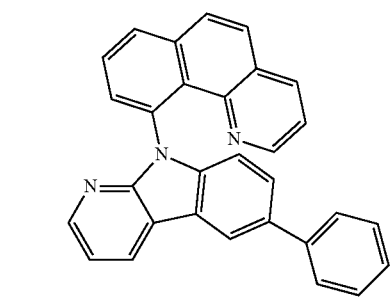

-continued
35
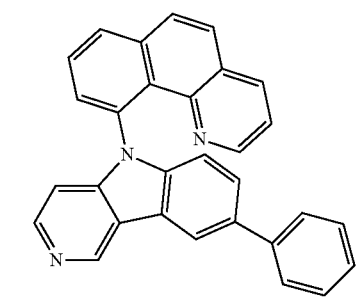
36
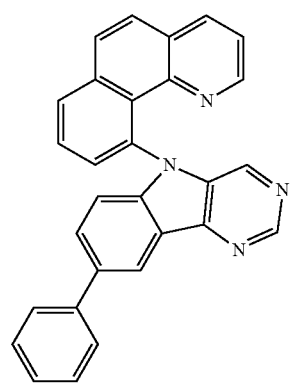
37
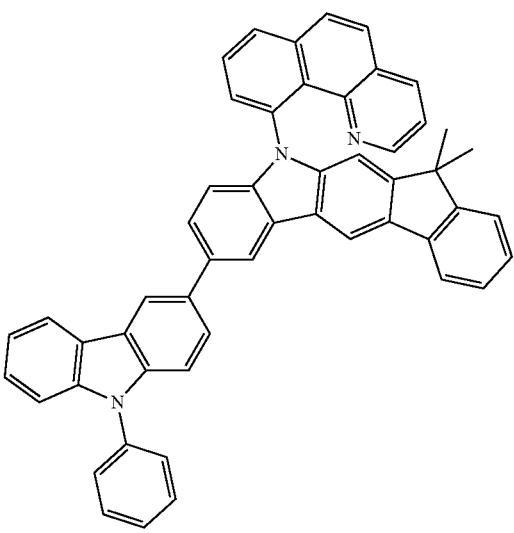
-continued
38
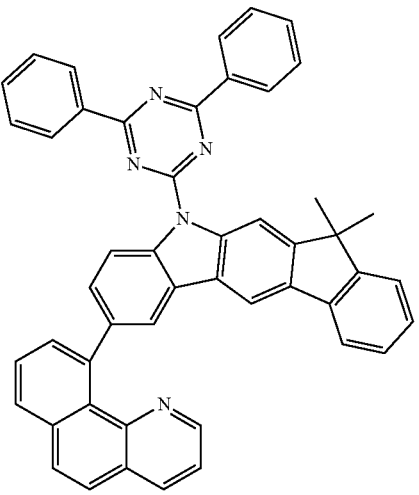
39
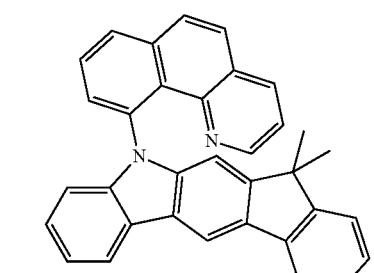
40
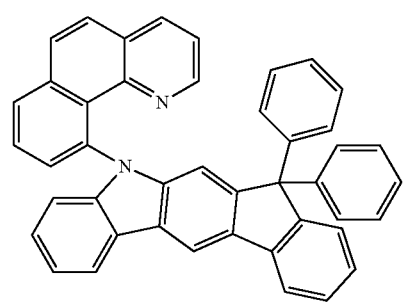
41
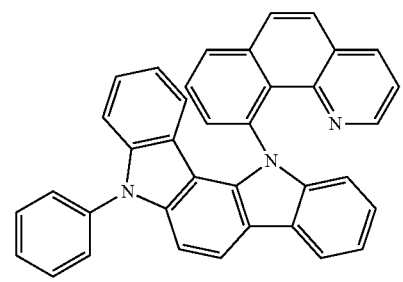
42
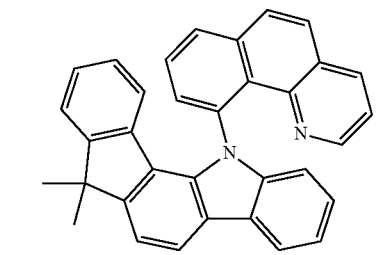

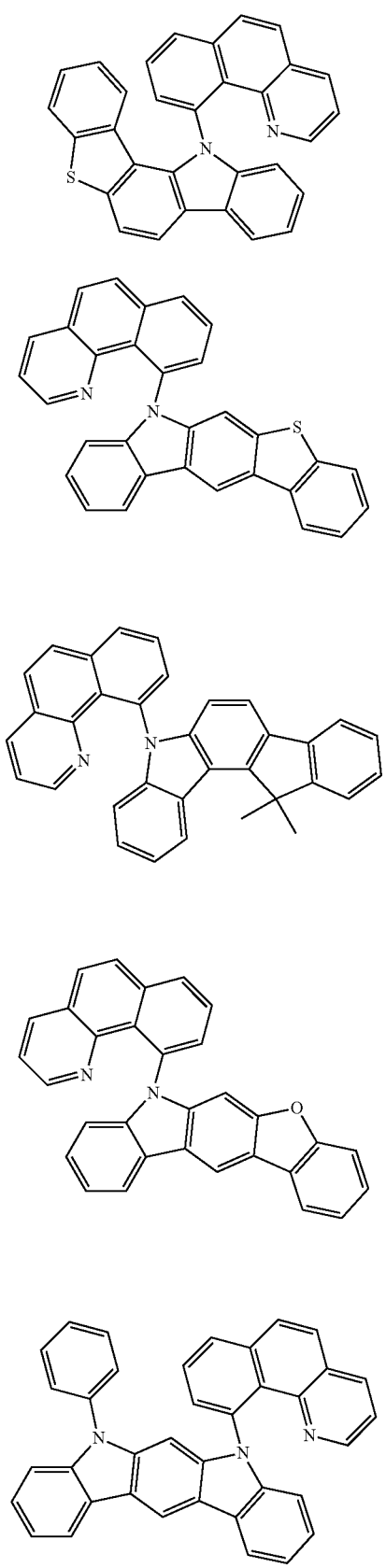
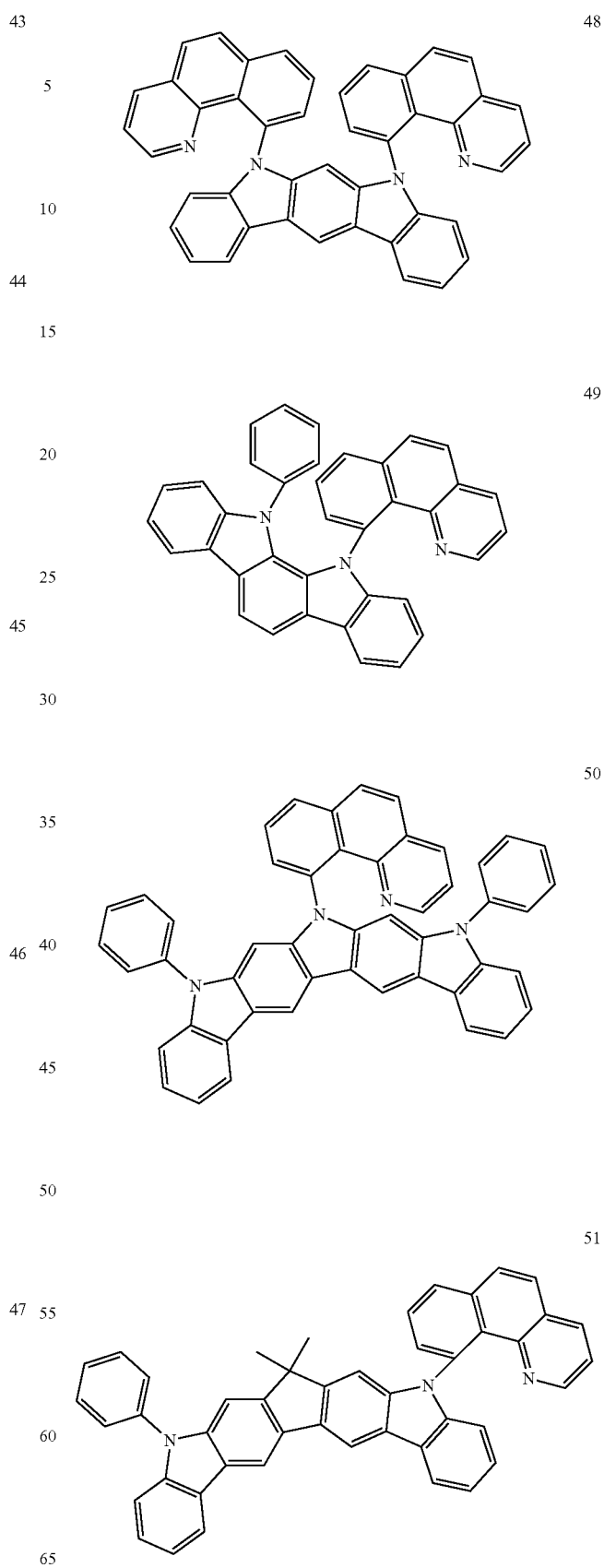

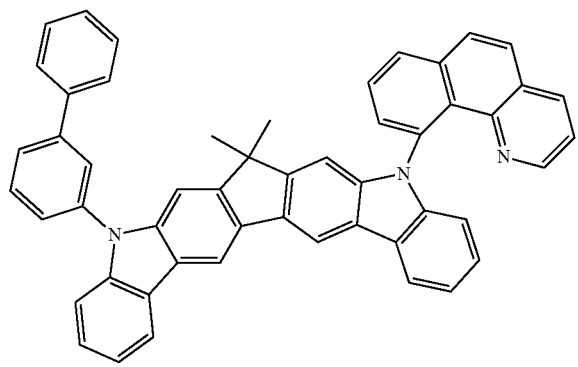
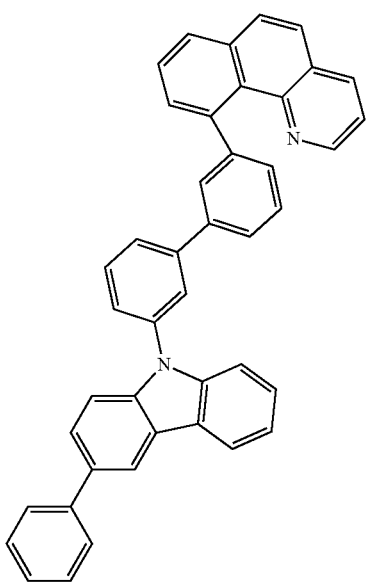
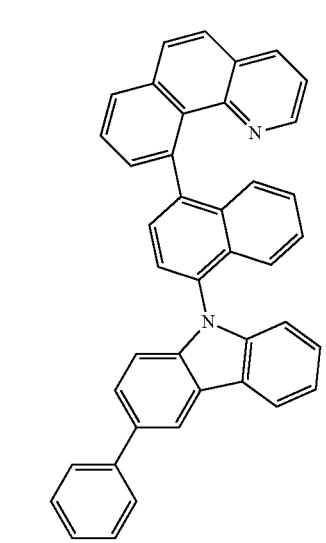

58
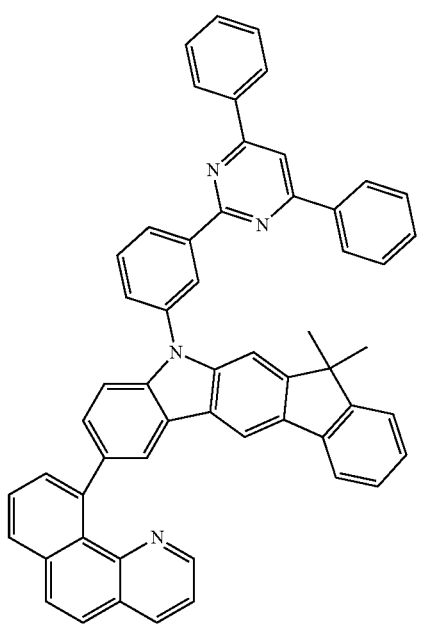
59
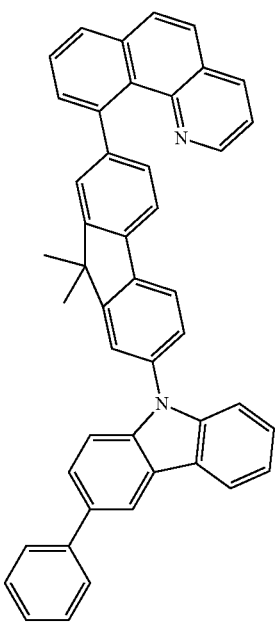
60
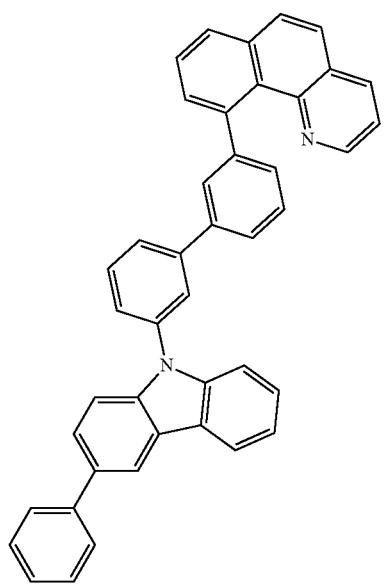
61
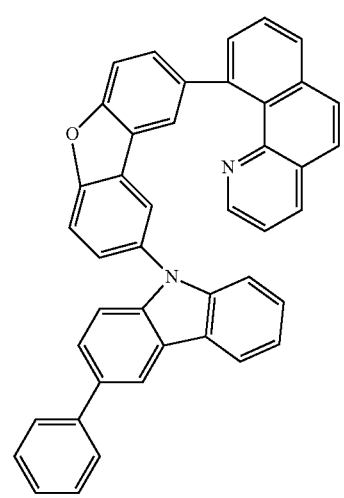
62
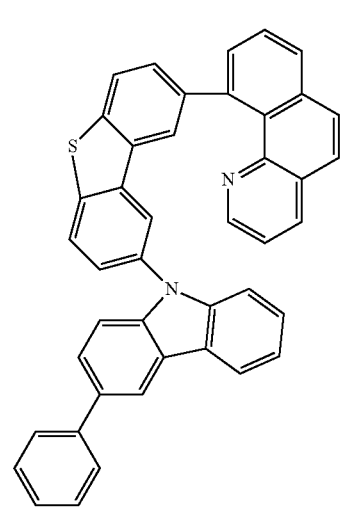

63
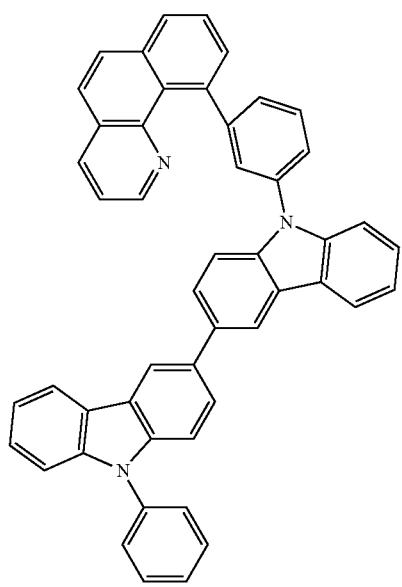
64
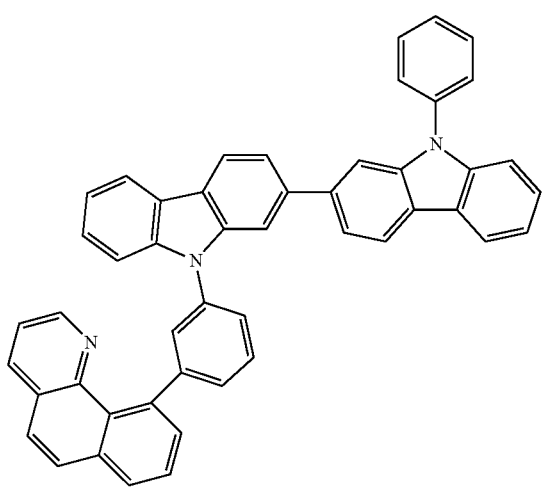
65
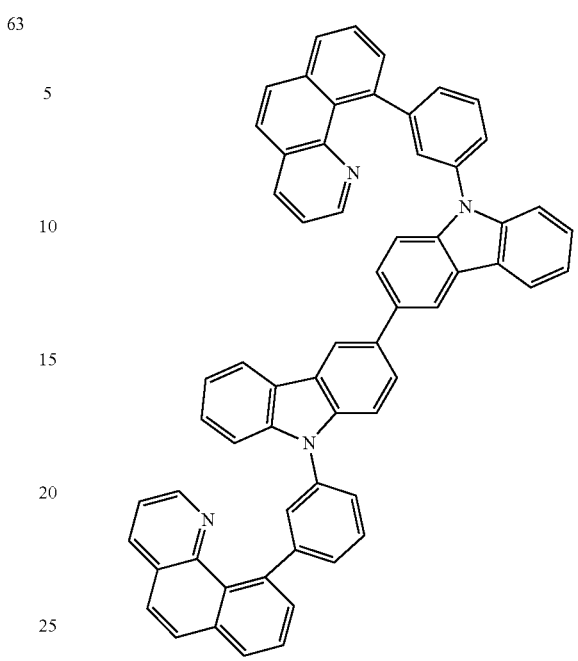
66
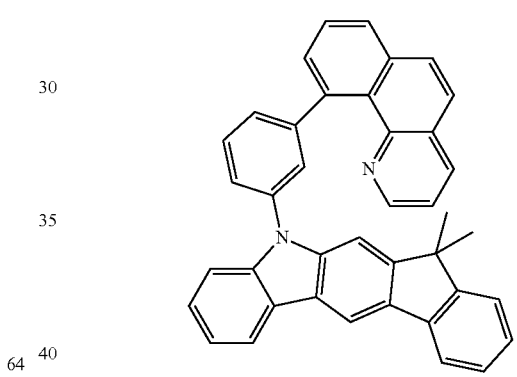
67
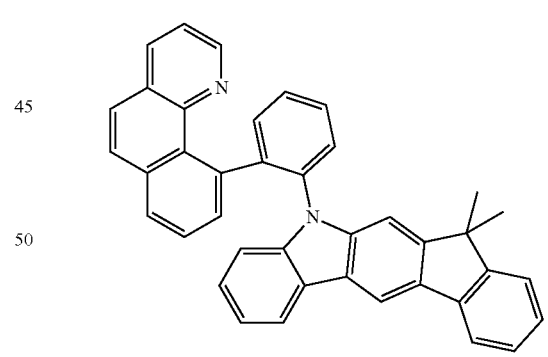
68
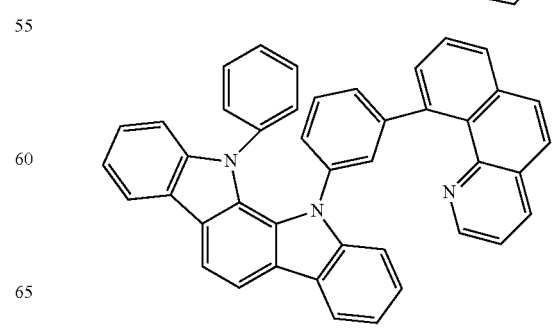

69
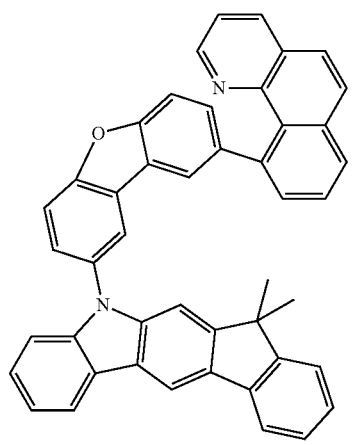
70
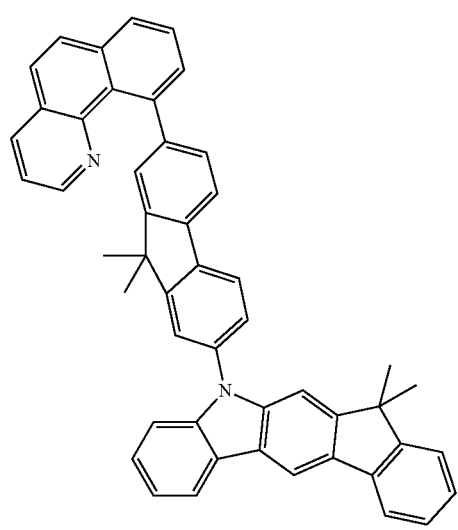
71
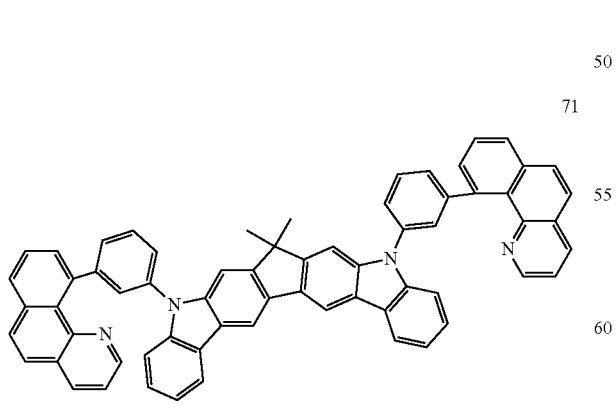
72
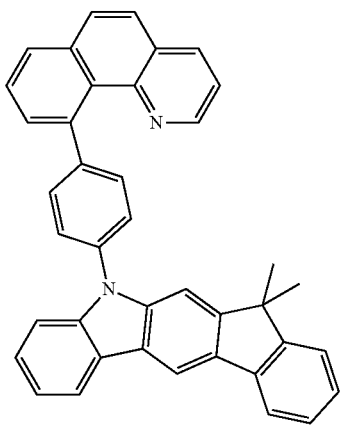
73
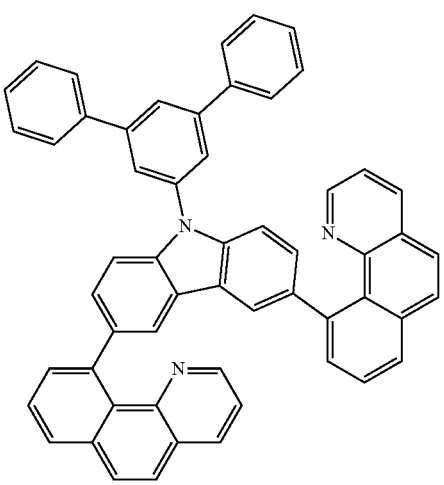
74
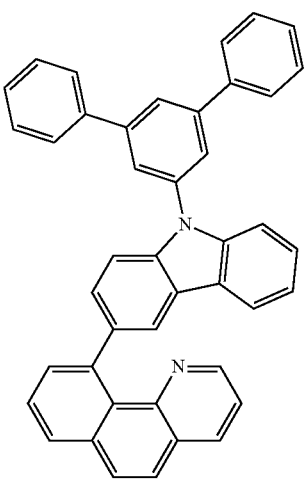

-continued
75
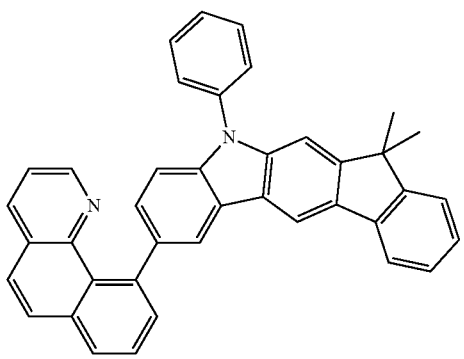
76
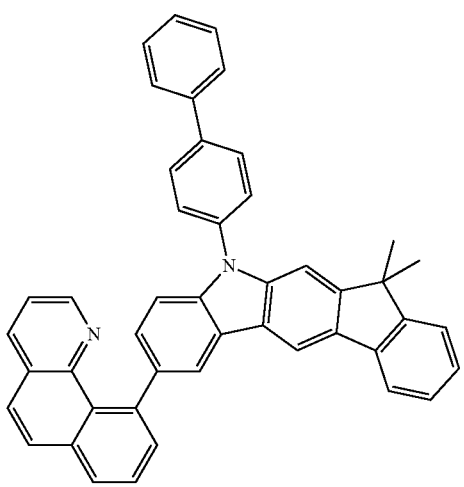
77
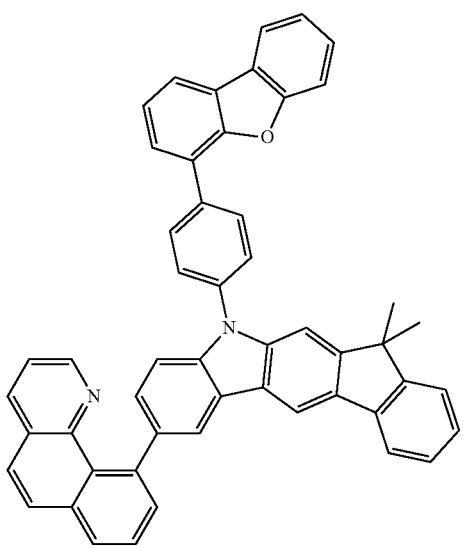
-continued
78
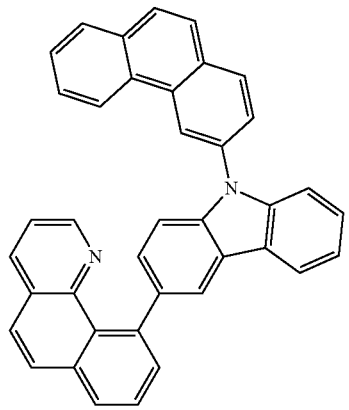
79
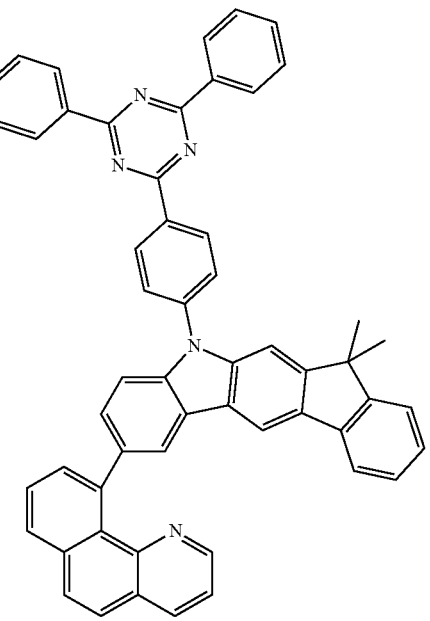
80
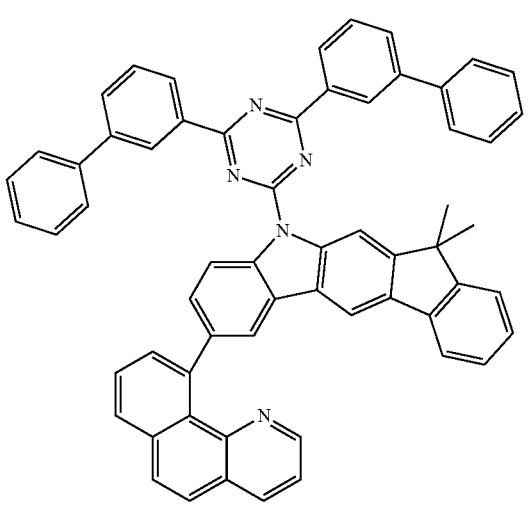

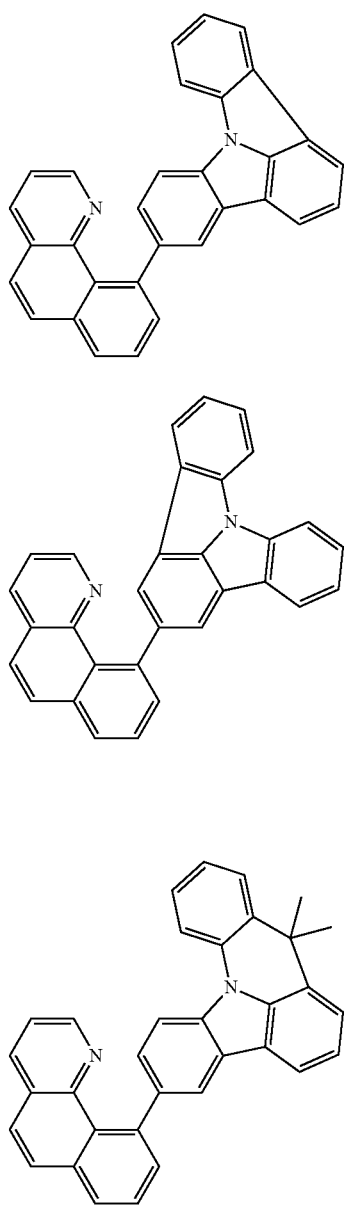
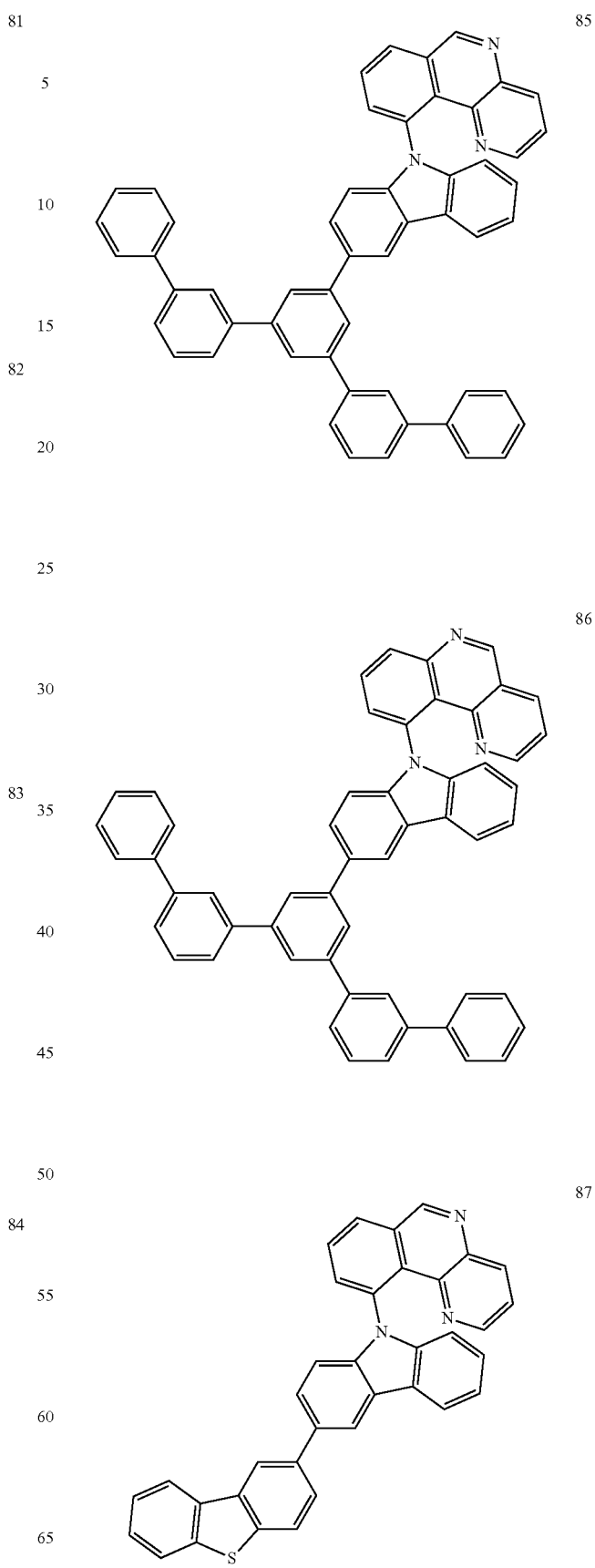

88
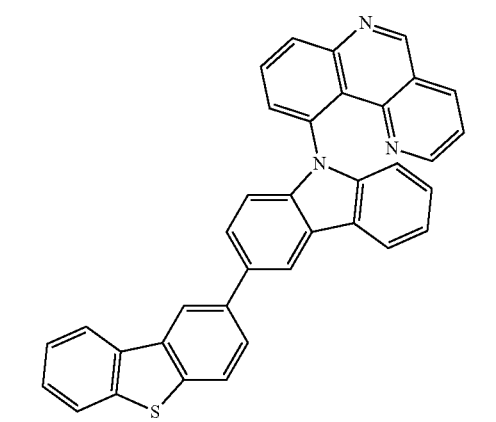
89
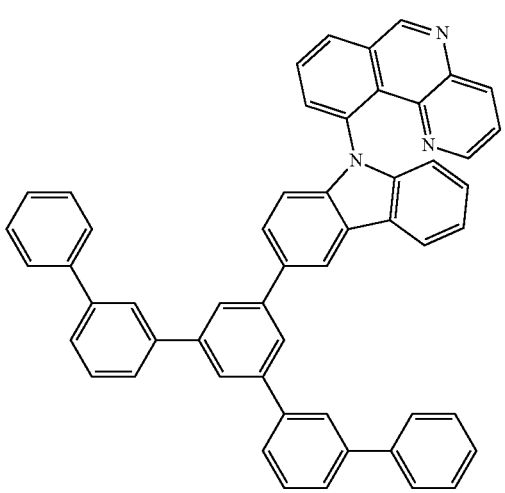
90
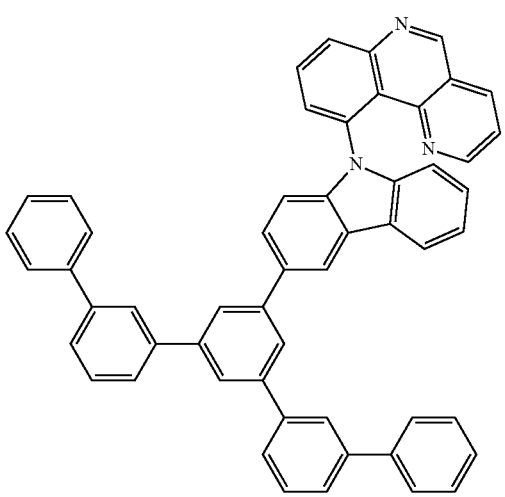
91
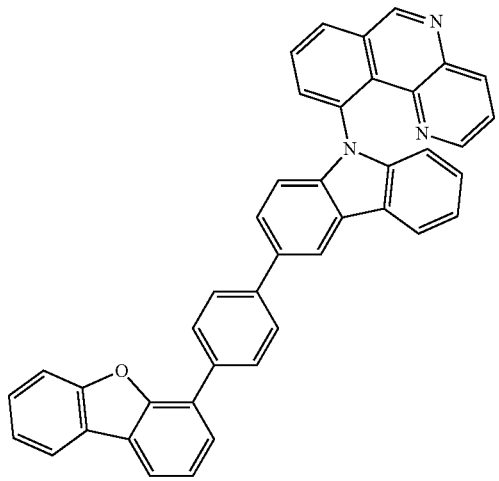
92
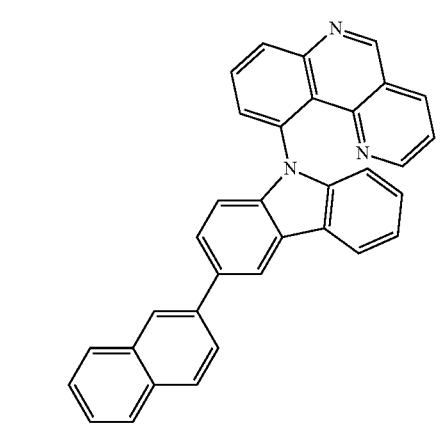
93
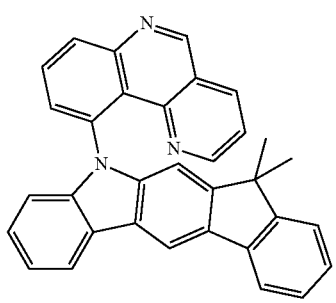
94
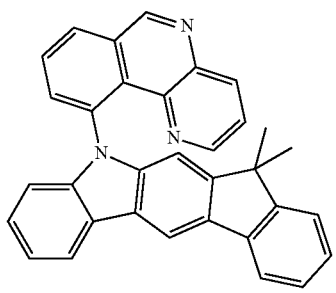

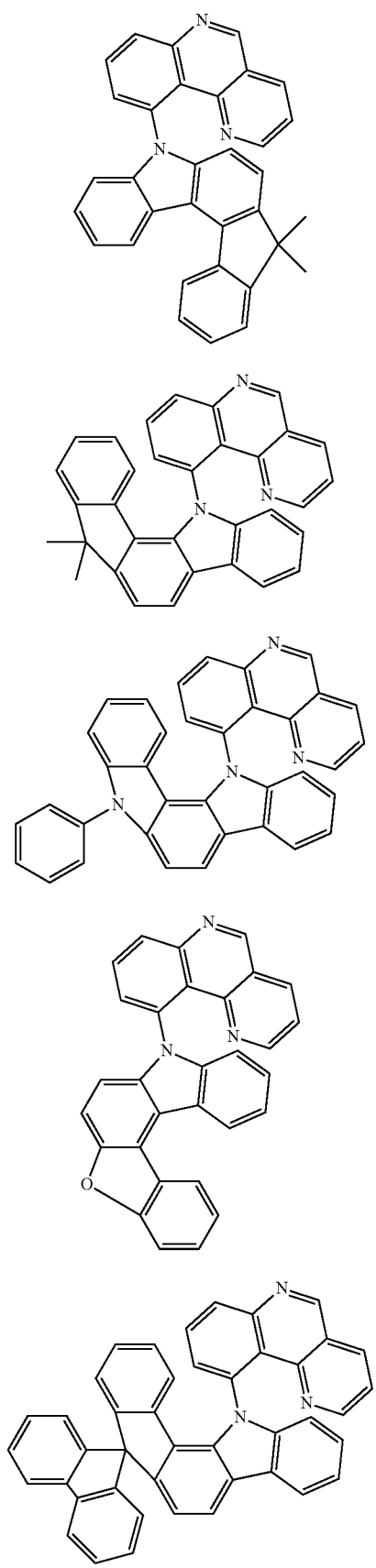
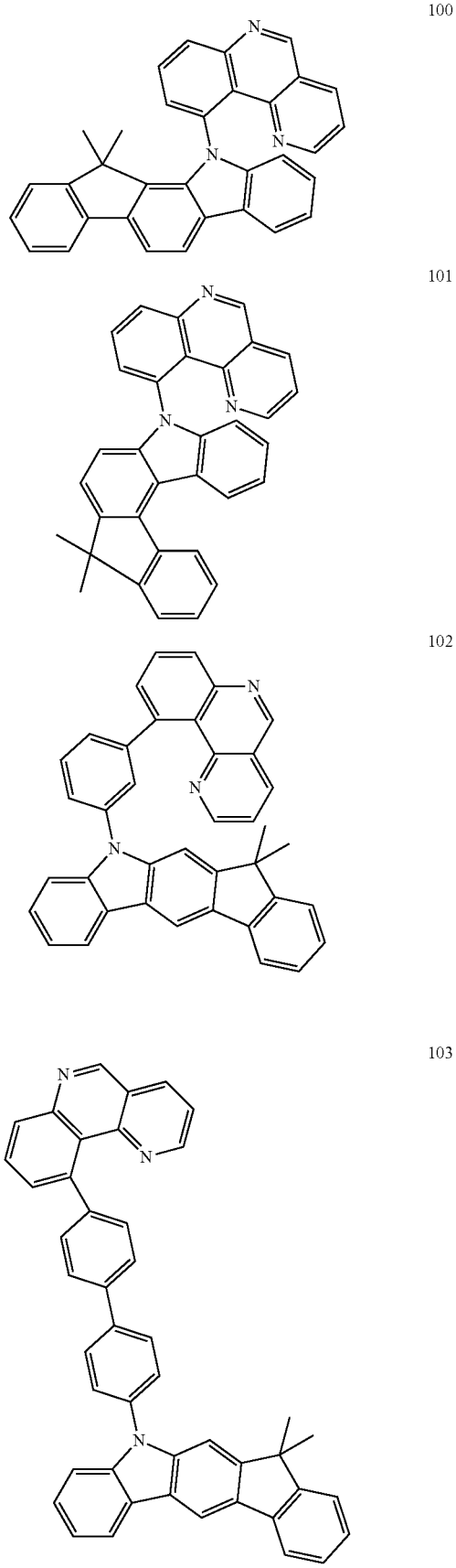

104
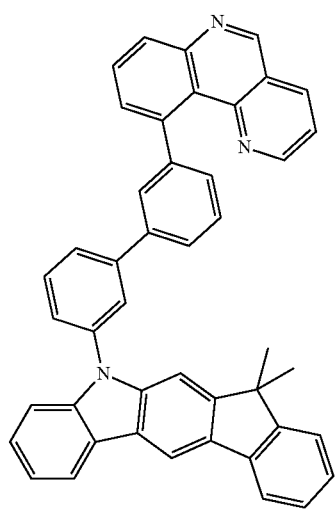
105
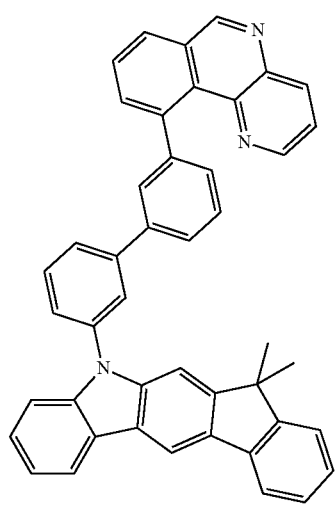
106
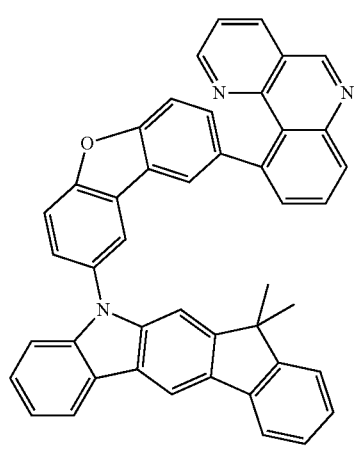
107
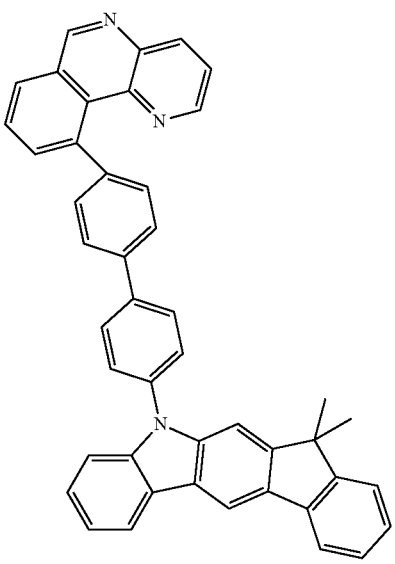
108
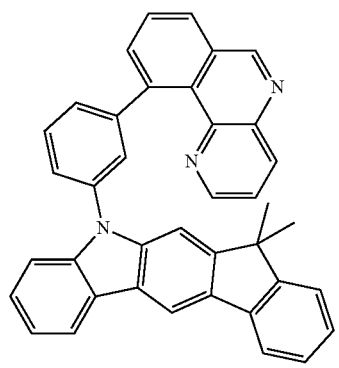
109
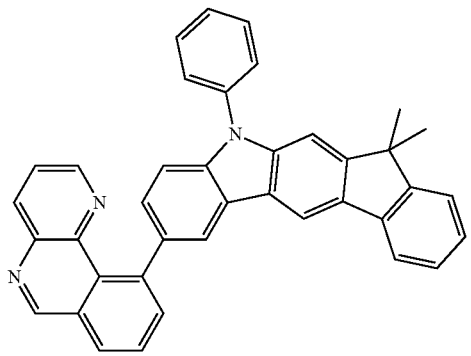

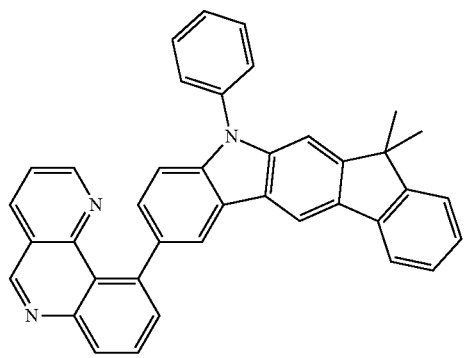
110
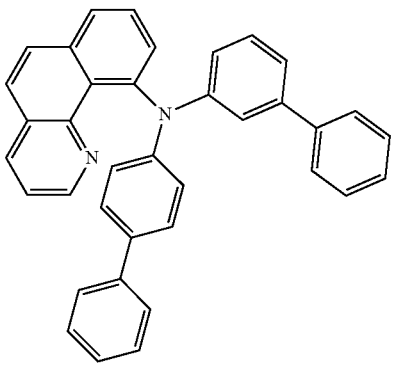
114
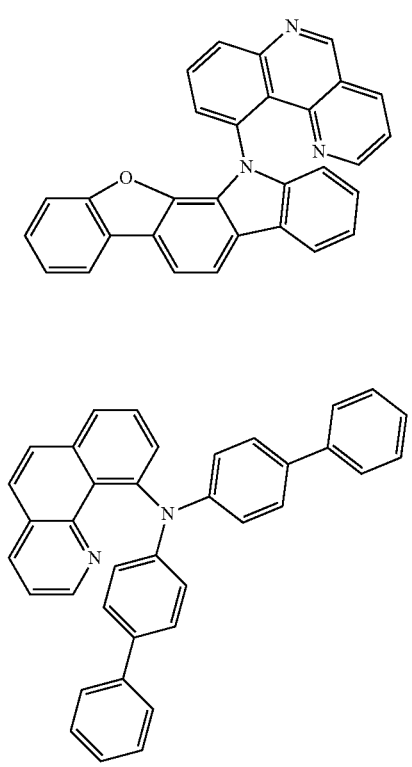
111
112
113
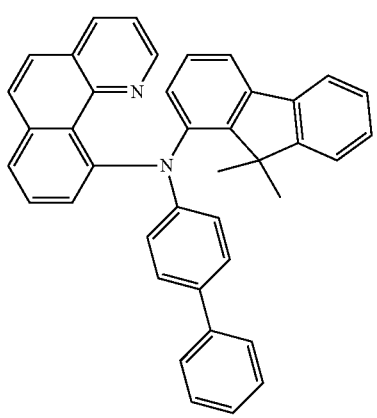
115
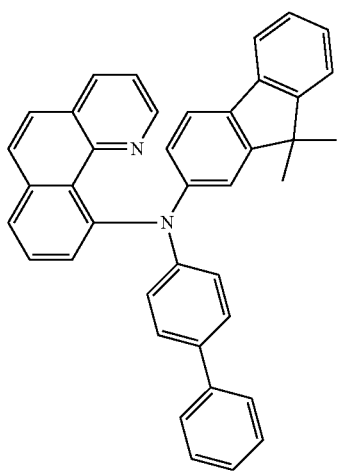
116

117
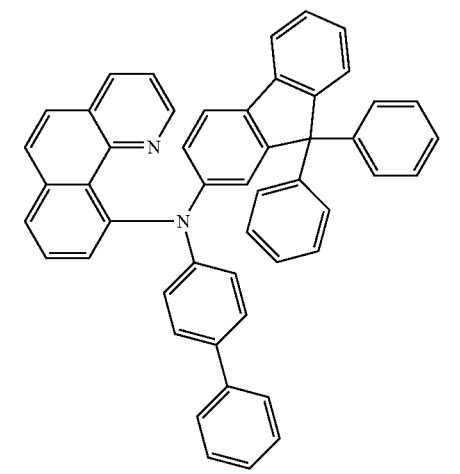
118
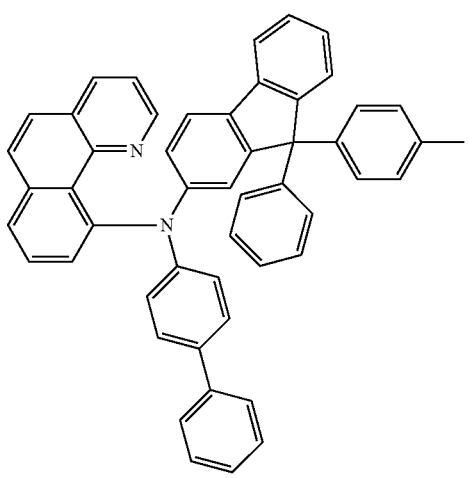
119
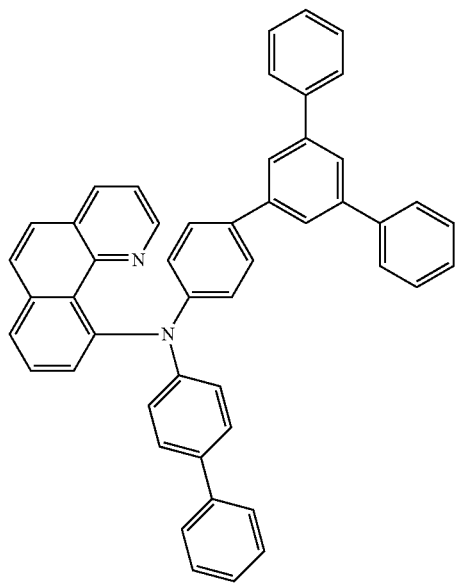
120
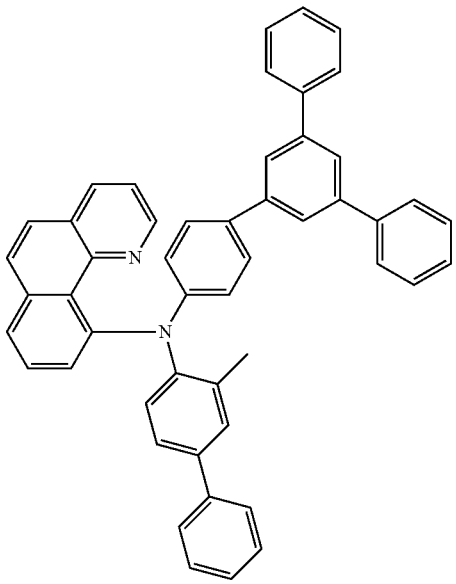
121
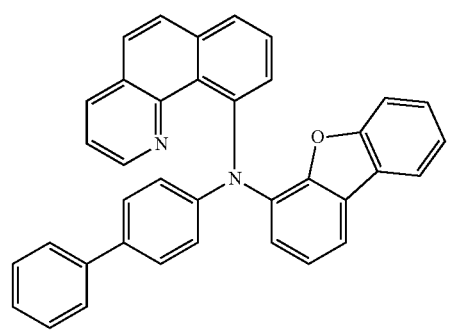
122
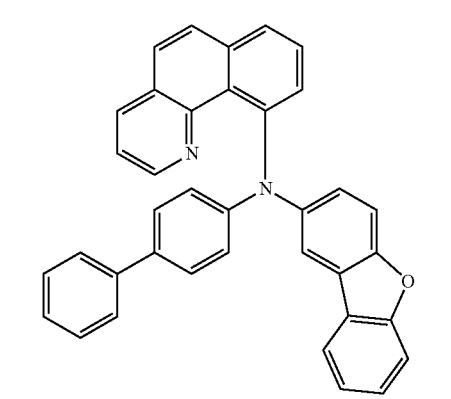
123
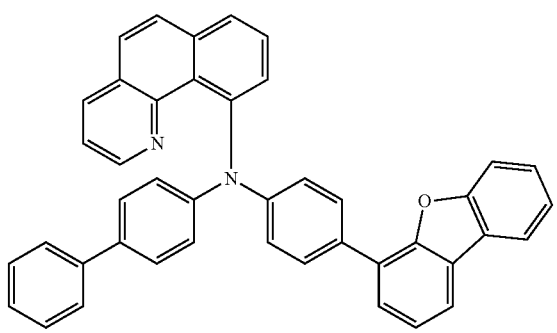

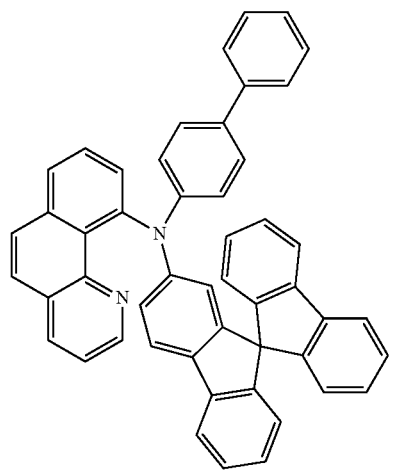
124
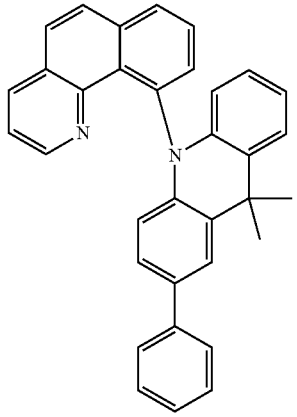
127
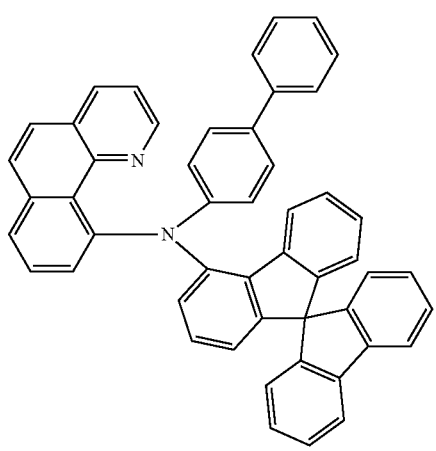
125
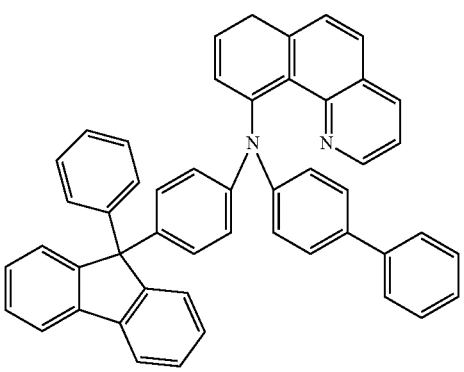
128
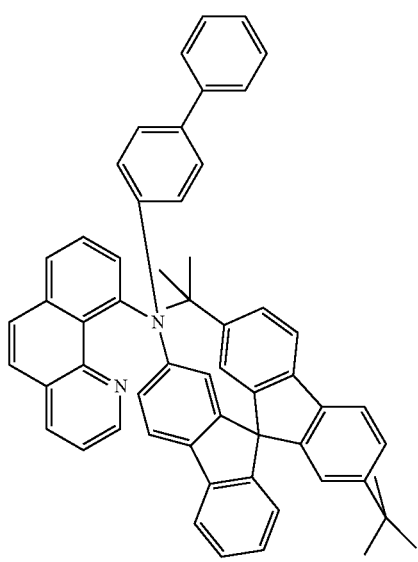
126
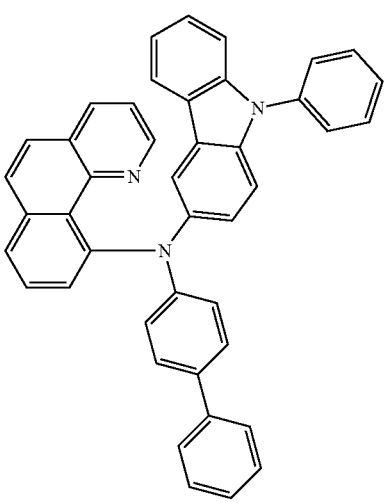
129

65
-continued
130
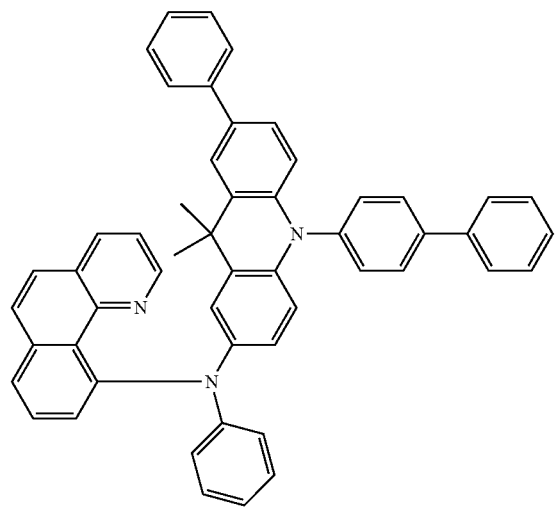
131
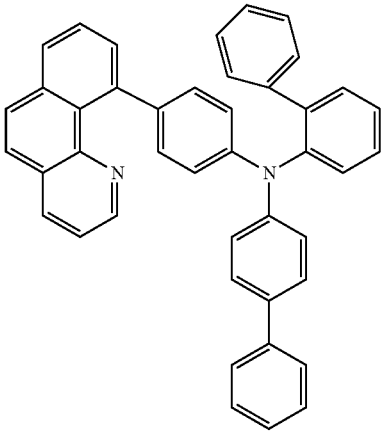
132
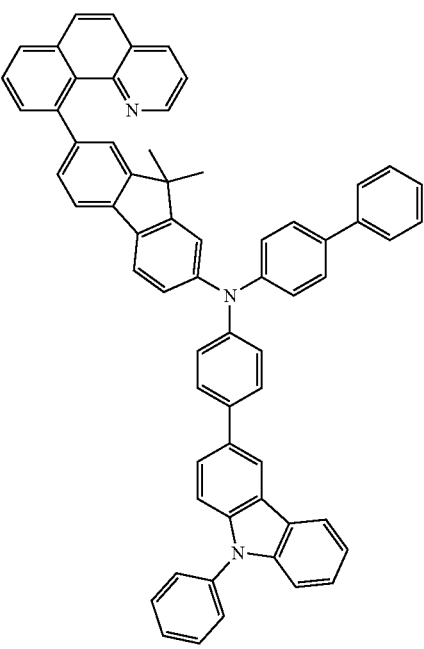
66
-continued
133
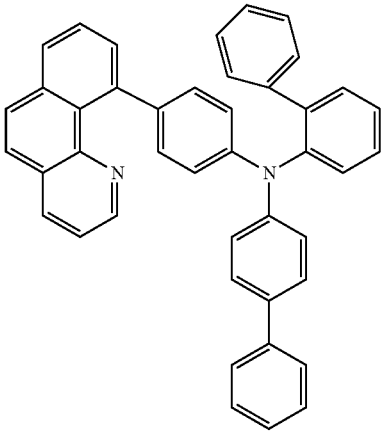
134
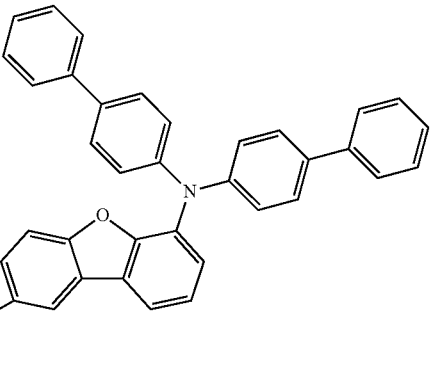
135
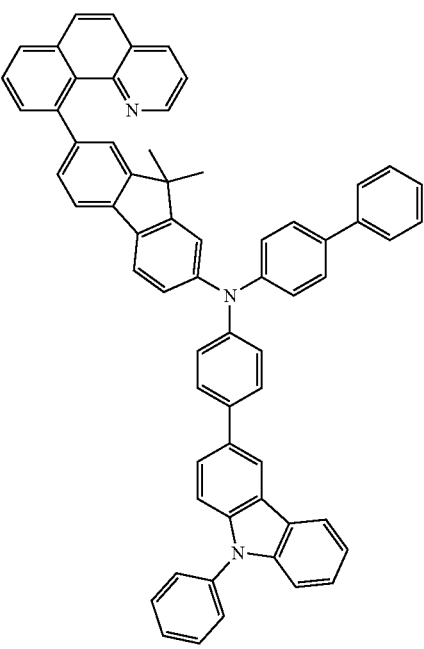

136
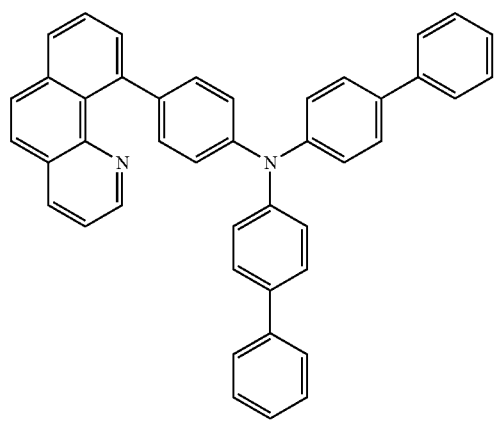
137
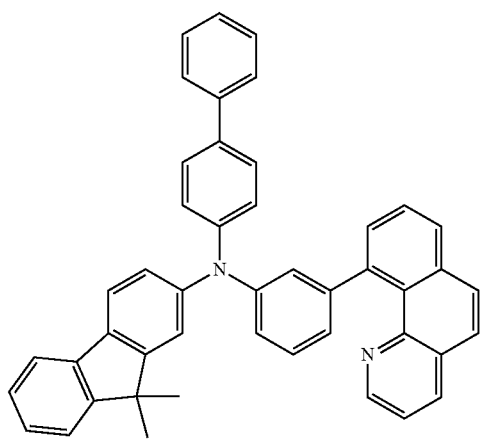
138
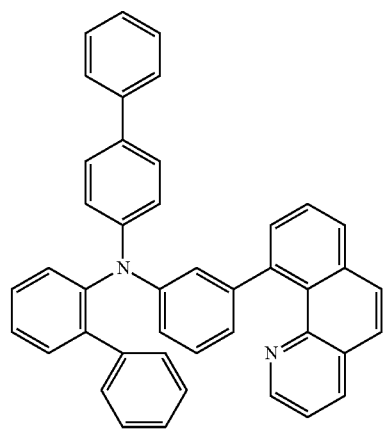
139
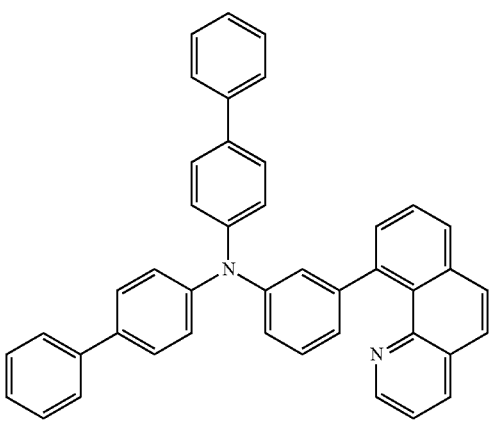
140
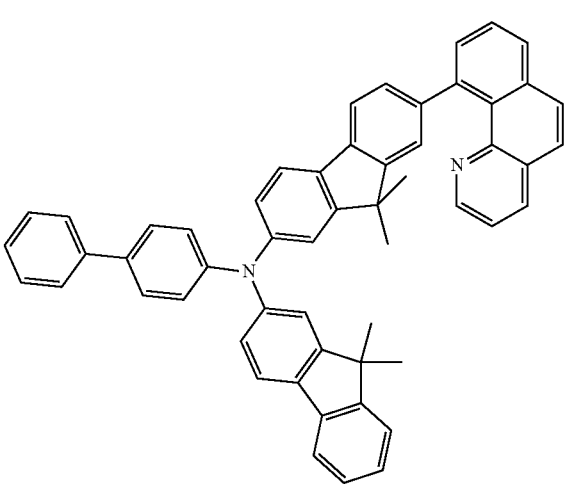
141
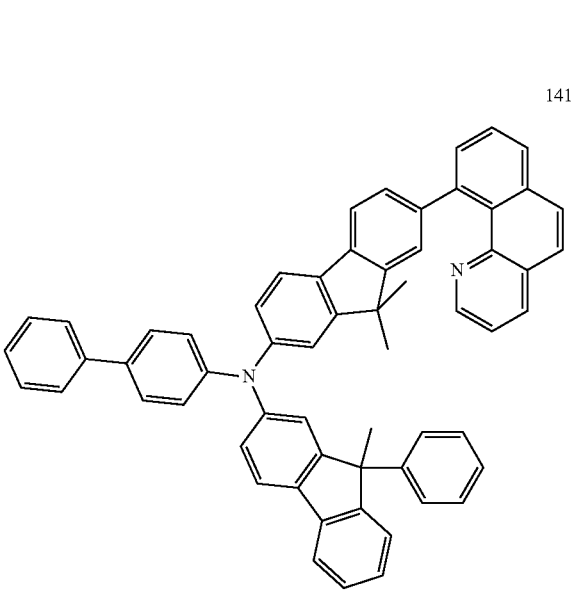

142
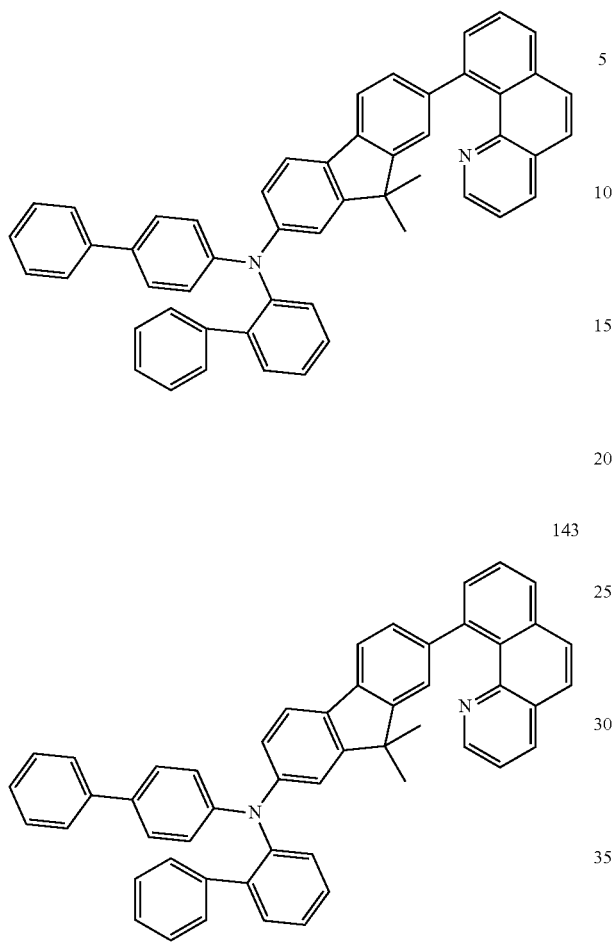
143
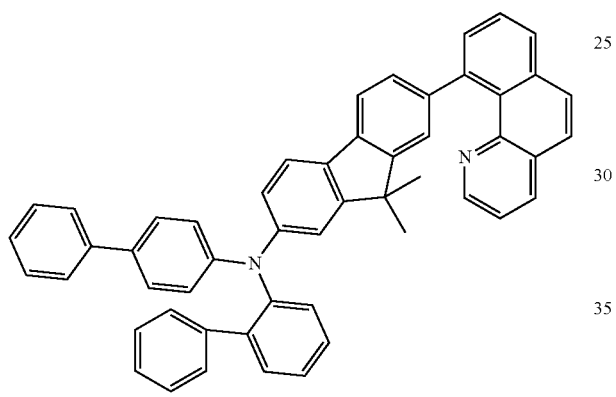
144
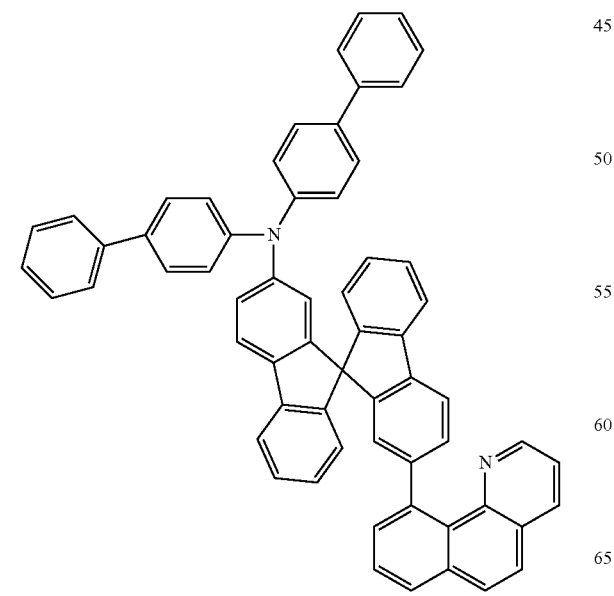
145
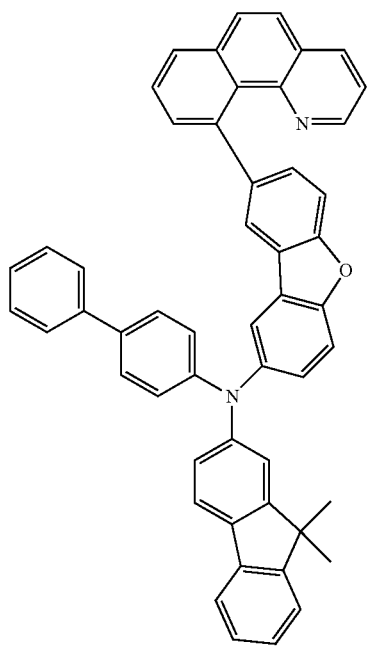
146
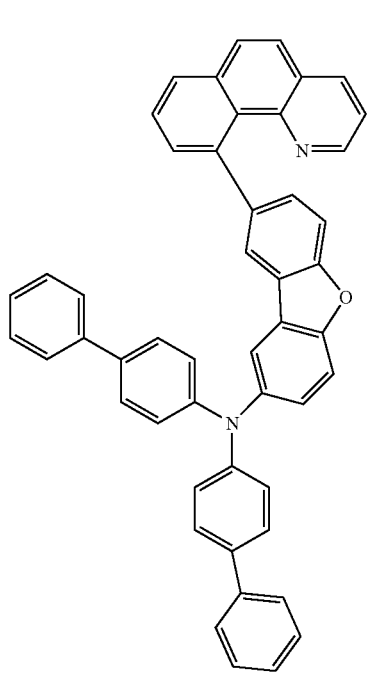

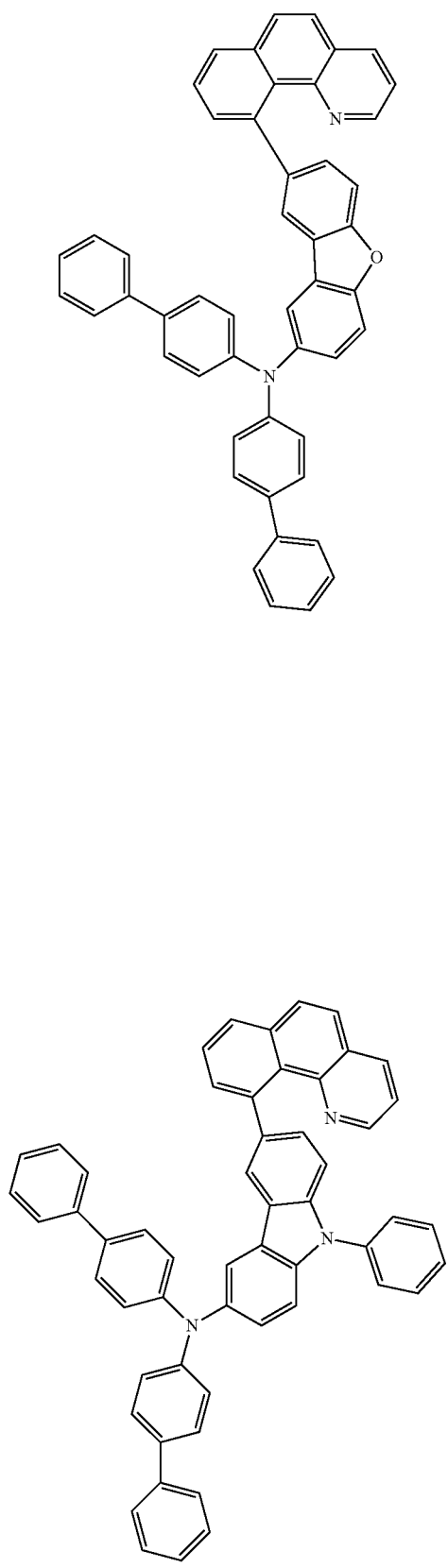
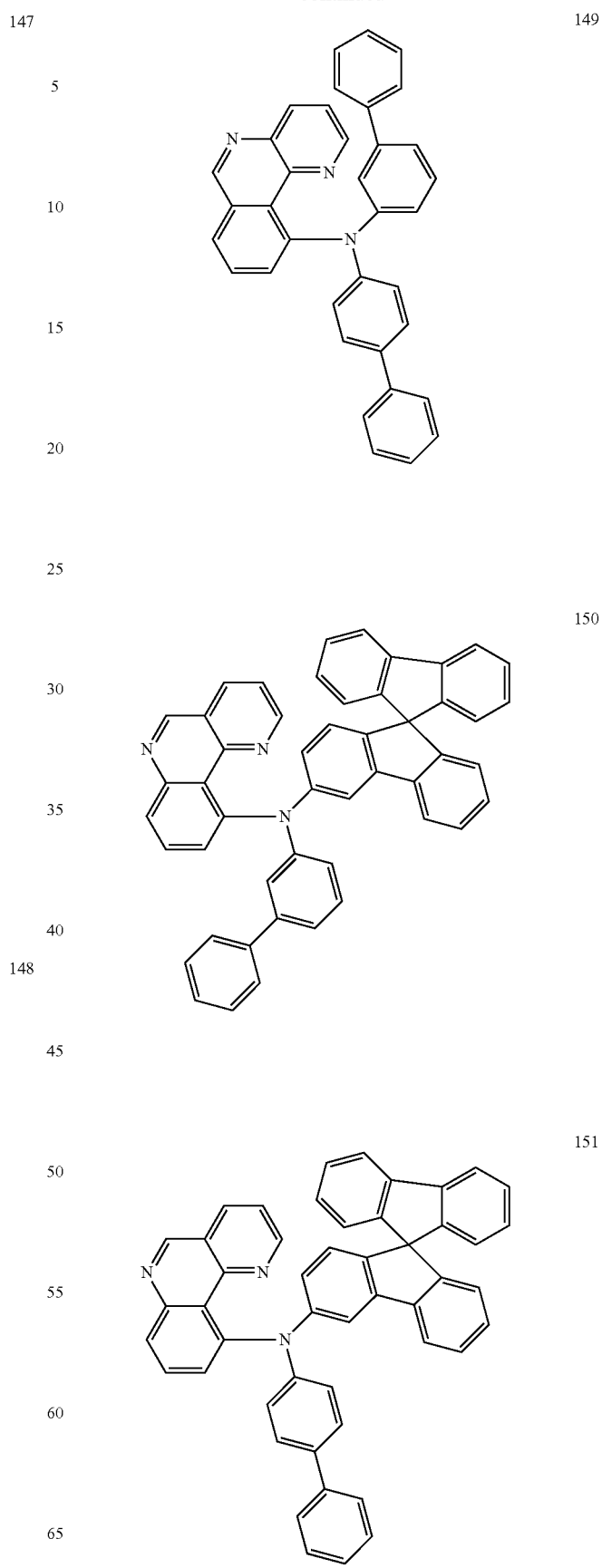

152

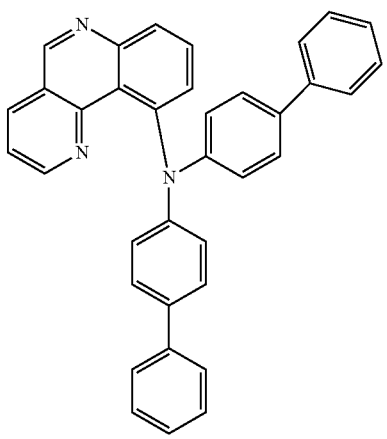

153

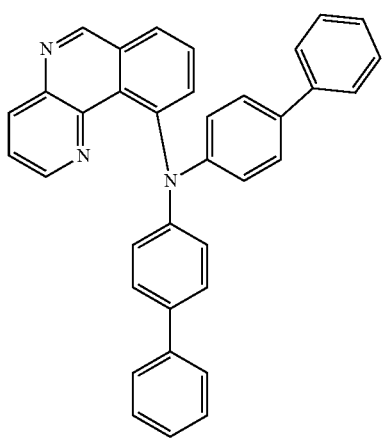

154

155

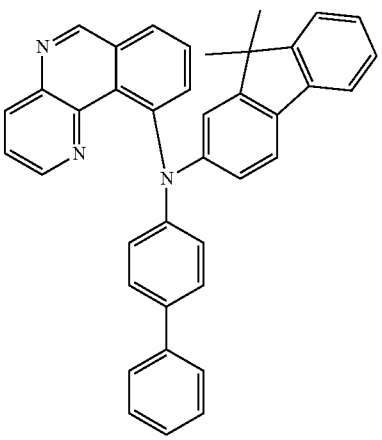

The synthesis of the inventive compounds can be conducted by the methods and reaction types known in the prior art, for example halogenation, Buchwald coupling and Suzuki coupling.

Scheme 1 shows a preferred synthesis route for preparation of the compounds of the invention. For synthesis of the compounds of the invention, the benzo[h]quinoline compound A is reacted with an amine B of the formula Ar—NH—Ar in a Buchwald coupling. In this scheme and in those which follow, the compounds are shown in unsubstituted form. They may alternatively be provided with any desired substituents.

Scheme 1

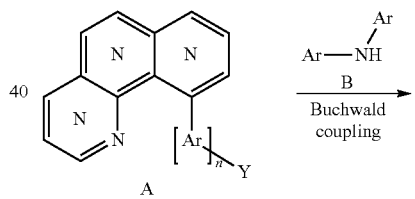

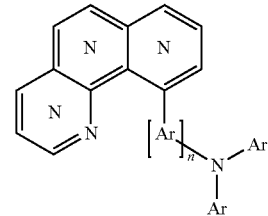

Y = leaving group, for example halogen
Ar = aromatic or heteroaromatic ring system
n = 0, 1, 2 or 3
Benzene ring with N in the middle: one or more ring atoms may be replaced by N Another preferred synthesis route for preparation of the compounds of the invention is shown in scheme 2. The synthesis route comprises two coupling reactions: first, the benzo[h]quinoline compound A is reacted with an amine C of the formula Ar—NH$_2$ in a first Buchwald coupling. Finally, a second Buchwald coupling is effected with a compound D, for example with a bromoaryl compound.

Scheme 2

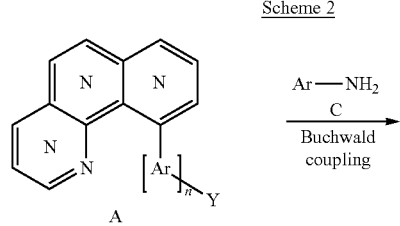
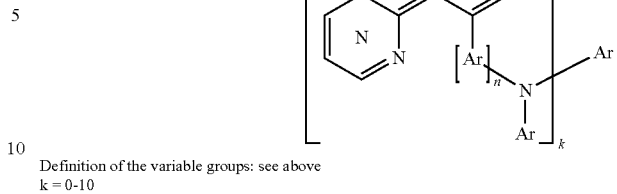

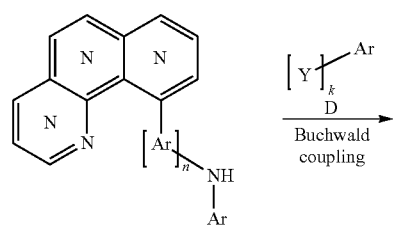

Definition of the variable groups: see above
k = 0-10

Synthesis routes for the starting compounds A which are used in the synthesis of the compounds of the invention are known to those skilled in the art. In addition, in the working examples, some explicit synthesis methods are illustrated in detail.

A further suitable synthesis method for preparation of compounds of the formula (I), especially those having carbazole substituents, is shown in general form in scheme 3 below. Carbazole groups (compounds G) are introduced into the compounds therein via Ullmann or Buchwald couplings. In addition, it is possible to introduce aryl groups substituted by carbazole or diarylamino groups (compounds H) via Suzuki couplings.

Scheme 3

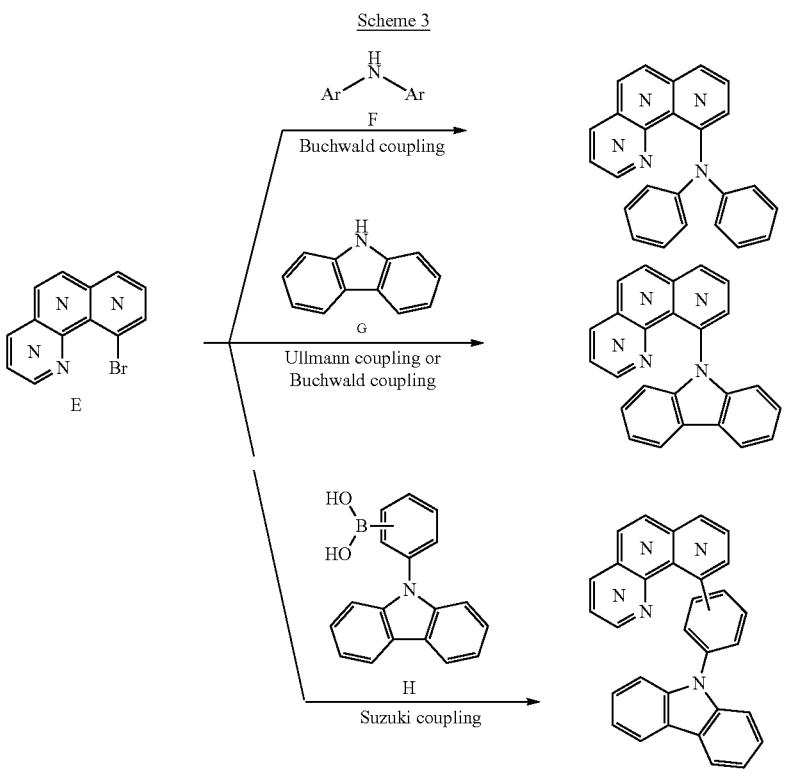

Definition of the variable groups: see above

The present invention thus further provides a process for preparing a compound of formula (I), characterized in that a compound of a formula (Int-I)

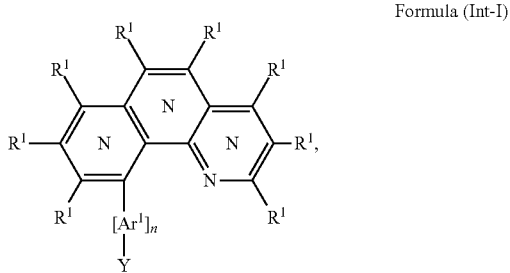

Formula (Int-I)

where the variable groups and indices that occur in the compound of the formula (Int-I) are as defined for the compound of the formula (I) and, in the benzene rings with an N drawn in the middle, one or more ring members —CR$^1$═ in each case may be replaced by —N═, and where Y is any reactive group, is converted further in a coupling reaction.

This coupling reaction is preferably a transition metal-catalyzed coupling reaction, more preferably a Pd- or Cu-catalyzed coupling reaction. It is most preferably a Buchwald coupling or an Ullmann coupling. The coupling reaction preferably takes place with the nitrogen atom of an arylamine compound or a carbazole compound.

The Y group is preferably selected from I, Br, Cl, an O-tosylate, an O-triflate, an O-sulfonate, boronic acid, a boronic ester, a partly fluorinated silyl group and a diazonium group. More preferably, the Y group is selected from I, Br and Cl.

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by R$^1$ or R$^2$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The inventive polymers, oligomers or dendrimers may be conjugated, partly conjugated or nonconjugated. The inventive oligomers or polymers may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are chosen from fluorenes (for example according to EP 842208 or WO 00/22026), spirobifluorenes (for example according to EP 707020, EP 894107 or WO 06/061181), paraphenylenes (for example according to WO 1992/18552), carbazoles (for example according to WO 04/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The inventive polymers, oligomers and dendrimers have advantageous properties, especially high lifetimes, high efficiencies and good color coordinates.

The inventive polymers and oligomers are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to C—C and C—N bonds are as follows:
(A) SUZUKI polymerization;
(B) YAMAMOTO polymerization;
(C) STILLE polymerization; and
(D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

For the processing of the inventive compounds from the liquid phase, for example by spin-coating or by printing methods, formulations of the inventive compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) or at least one polymer, oligomer or dendrimer containing at least one unit of formula (I) and at least one solvent, preferably an organic solvent. The way in which such solutions can be prepared is known to those skilled in the art and is described, for example, in WO 2002/072714, WO 2003/019694 and the literature cited therein.

The inventive compounds are suitable for use in electronic devices, especially in organic electroluminescent devices (OLEDs). The compounds, depending on the substitution among other factors, may be used in different functions and/or layers. Preferably, the compounds are used as matrix materials, more preferably as matrix materials for phosphorescent emitters in an emitting layer, or as hole transport materials in a hole transport layer. In an alternative embodiment of the invention, the compounds may also be used as electron transport materials in an electron transport layer.

The invention further provides for the use of the compounds of formula (I) in electronic devices. These electronic devices are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and more preferably selected from organic electroluminescent devices (OLEDs).

The invention further provides an electronic device comprising anode, cathode and at least one organic layer, wherein the organic layer comprises at least one compound of the formula (I). This electronic device is preferably selected from the abovementioned devices and is more preferably an organic electroluminescent device (OLED).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), outcoupling layers and/or organic or inorganic p/n junctions. However, it should be pointed out that not every one of these layers need necessarily be present and the choice of layers always depends on the compounds used and especially also on whether the device is a fluorescent or phosphorescent electroluminescent device. The compounds used with preference in the particular layers and functions are disclosed explicitly in later paragraphs.

The sequence of layers in the organic electroluminescent device is preferably as follows:
anode
hole injection layer
hole transport layer
optionally 1, 2 or 3 further hole transport layers
emitting layer
electron transport layer
electron injection layer
cathode.

It is not necessary for all the layers mentioned to be present, and/or further layers may additionally be present.

The inventive organic electroluminescent device may contain two or more emitting layers. More preferably, these emission layers in this case have several emission maxima between 380 nm and 750 nm overall, such that the overall result is white emission; in other words, various emitting compounds which may fluoresce or phosphoresce and which emit blue or yellow or orange or red light are used in the emitting layers. Especially preferred are three-layer systems, i.e. systems having three emitting layers, where preferably at least one of these layers comprises at least one compound of formula (I) and where the three layers show blue, green and orange or red emission (for the basic construction see, for example, WO 2005/011013). Alternatively and/or additionally, the compounds of the invention may also be present in the hole transport layer or in another layer.

In white-emitting OLEDs according to the present application, rather than a plurality of color-emitting emitter compounds, it is also possible to use a single emitter compound which emits over a wide wavelength range.

It is preferable in accordance with the invention when the compound of formula (I) is used in an electronic device comprising one or more phosphorescent emitters. In this case, the compound may be used in different layers, preferably in a hole transport layer or in an emitting layer.

The term "phosphorescent emitters", according to the present application, encompasses compounds where the emission of light is effected through a spin-forbidden transition, for example a transition from an excited triplet state or a state having a higher spin quantum number, such as a quintet state.

Suitable phosphorescent emitters are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitters, compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of phosphorescent emitters can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices. It is also possible for the person skilled in the art, without exercising inventive skill, to use further phosphorescent complexes in combination with the inventive compounds in OLEDs. Further examples of suitable phosphorescent emitters can be found in the table which follows in a later section.

In a preferred embodiment of the present invention, the compounds of the formula (I) are used as matrix material in an emitting layer in combination with one or more fluorescent or phosphorescent emitters, preferably phosphorescent emitters. Preferably, the compounds of the formula (I) in this case have an X group which is a single bond, and so the compounds contain a carbazole group.

The proportion of the matrix material in the emitting layer in this case is between 50.0% and 99.9%, preferably between 80.0% and 99.5%, and more preferably between 92.0% and 99.5% for fluorescent emitting layers and between 85.0% and 97.0% for phosphorescent emitting layers. Correspondingly, the proportion of the emitter is between 0.1% and 50.0%, preferably between 0.5% and 20.0%, and more preferably between 0.5% and 8.0% for fluorescent emitting layers and between 3.0% and 15.0% for phosphorescent emitting layers.

Figures for the proportions of compounds in % in those cases where the compound are applied from the gas phase are understood to mean percent by volume, and in those cases where the compounds are applied from the liquid phase percent by weight.

An emitting layer of an organic electroluminescent device may also comprise systems comprising a plurality of matrix materials (mixed matrix systems) and/or a plurality of emitters. In this case too, the emitters are generally those materials having the smaller proportion in the system and the matrix materials are those materials having the greater proportion in the system. In individual cases, however, the proportion of a single matrix material in the system may be less than the proportion of a single emitter material.

In a further preferred embodiment of the invention, the compounds of formula (I) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The mixed matrix systems may comprise one or more emitter compounds. According to the invention, the emitter compounds together have a proportion of 0.1% to 50.0% of the overall mixture and preferably a proportion of 0.5% to 20.0% of the overall mixture. Correspondingly, the matrix compounds together have a proportion of 50.0% to 99.9% of the overall mixture and preferably a proportion of 80.0% to 99.5% of the overall mixture.

Particularly suitable matrix materials which can be used in combination with the inventive compounds as matrix components of a mixed matrix system are selected from the preferred matrix materials specified below for phosphorescent emitters or the preferred matrix materials for fluorescent emitters, according to what type of emitter is used in the mixed matrix system.

Preferred phosphorescent emitters for use in mixed matrix systems comprising the compounds of the invention are the phosphorescent emitters listed in a table which follows.

In a further preferred embodiment of the invention, the compounds of formula (I) are used as hole transport material. In that case, the compounds are preferably used in a hole transport layer, an electron blocker layer or a hole injection layer. Preferably, the compounds of the formula (I) in this case do not have any X group, meaning that the compounds have A groups that are arylamino groups.

A hole transport layer according to the present application is a layer having a hole-transporting function between the anode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side.

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer containing the compound of the formula (I) then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, 8,057,712, WO 2009/003455, WO 2010/094378, WO 2011/120709, US 2010/0096600 and WO 2012/095143.

Particularly preferred p-dopants are quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

In a further embodiment of the invention, the compound of formula (I) is used as electron transport material in an electron transport layer or electron injection layer or hole blocker layer. For this purpose, it is preferable that the compound of the formula (I) has an X group which is a single bond, such that the compound contains a carbazole group. Preferably, the compound, in the case of this use, additionally contains one or more electron-withdrawing groups, for example electron-deficient heteroaryl groups such as pyrimidine groups, triazine groups or benzimidazole groups.

The further functional materials used with preference in the electronic devices of the invention are detailed hereinafter.

The compounds listed in the table which follows are particularly suitable phosphorescent emitters.

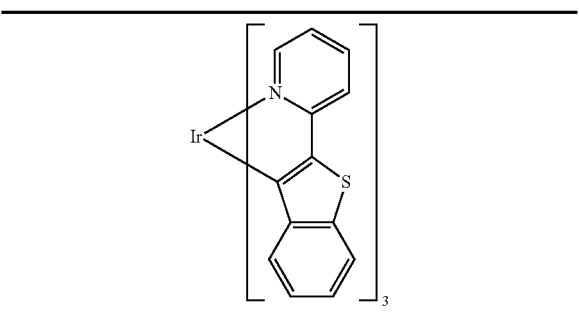
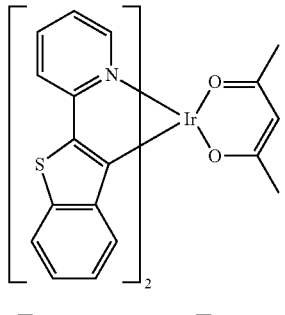
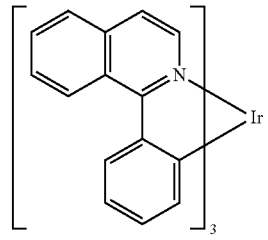
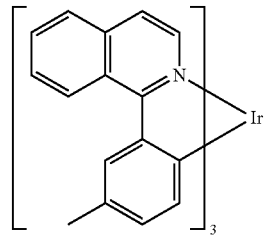
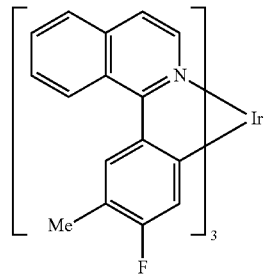
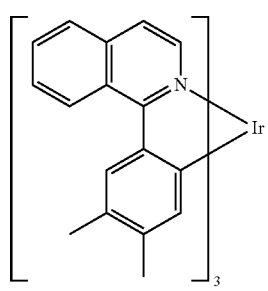
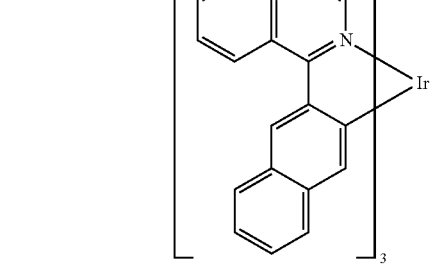
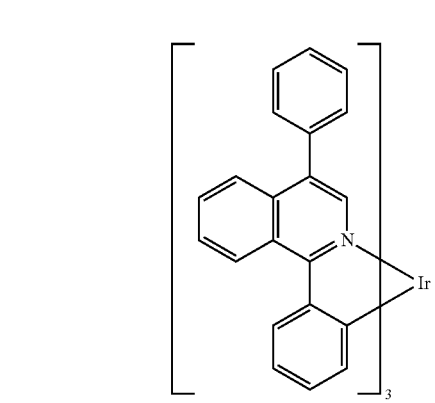
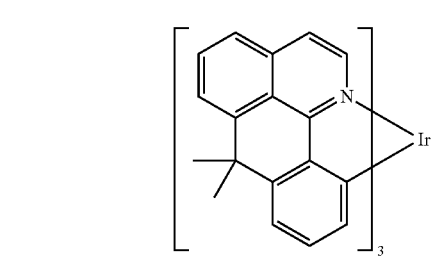
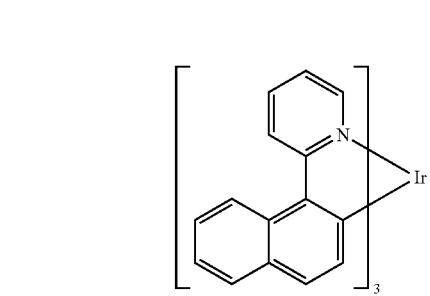
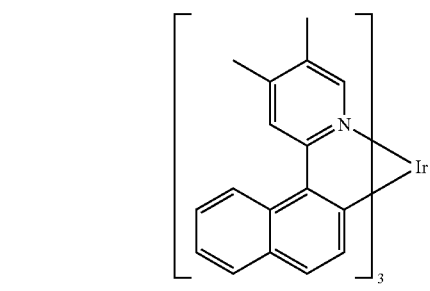

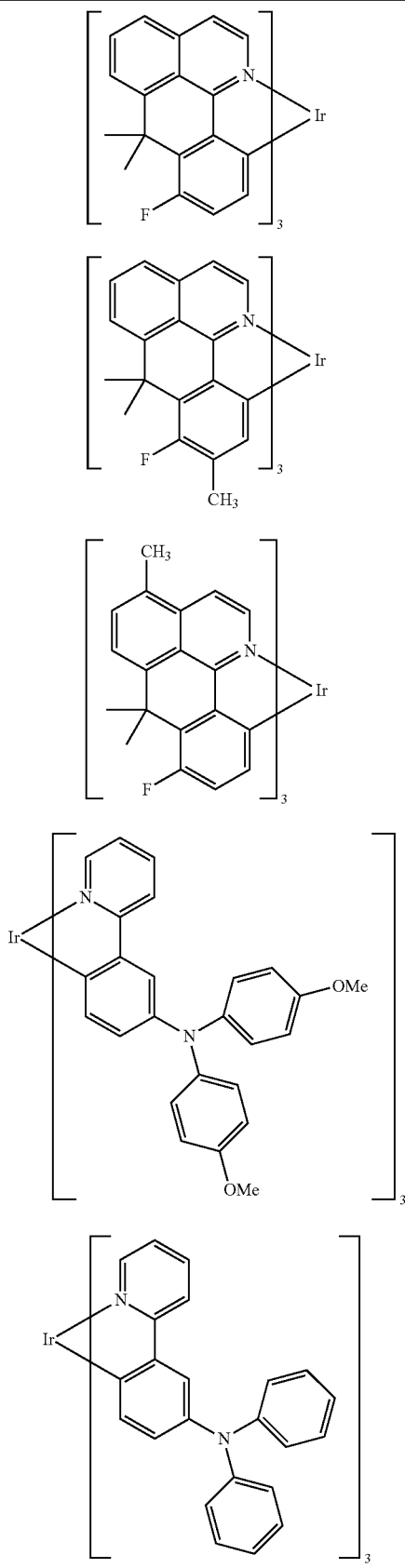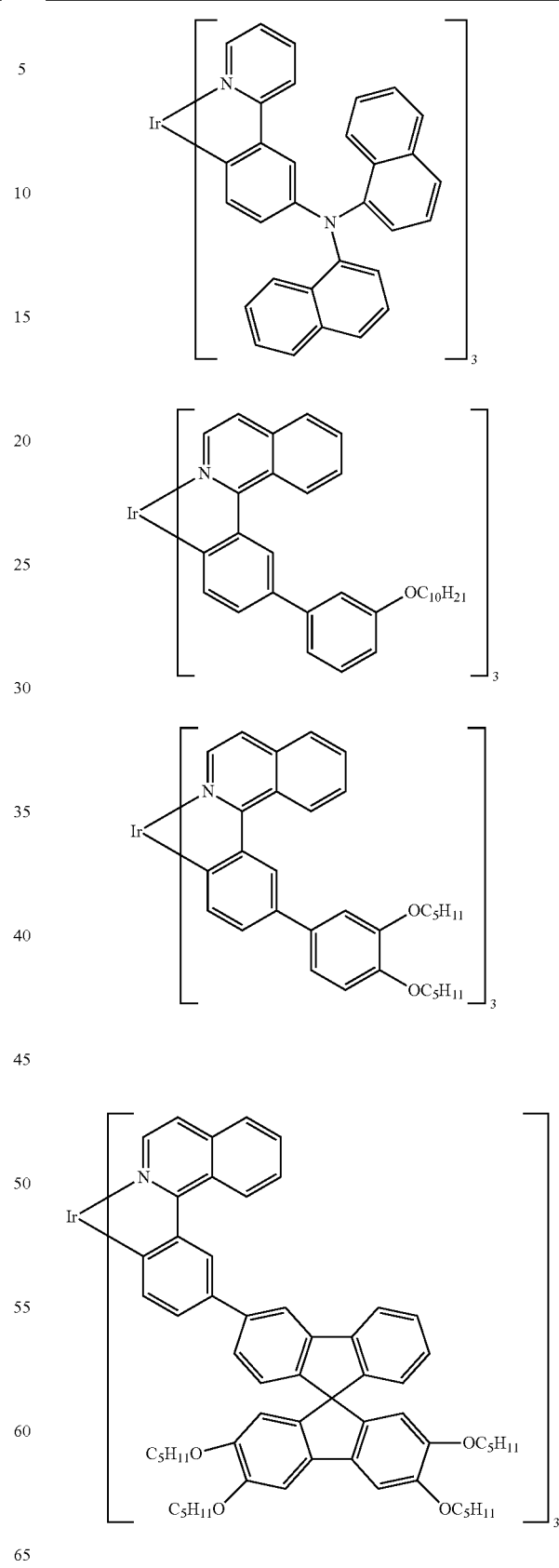

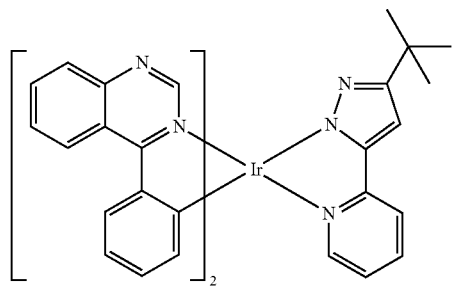
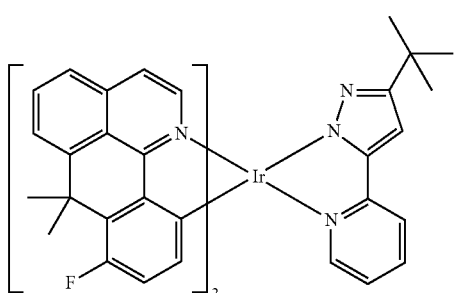
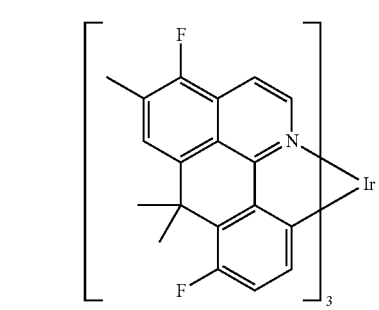
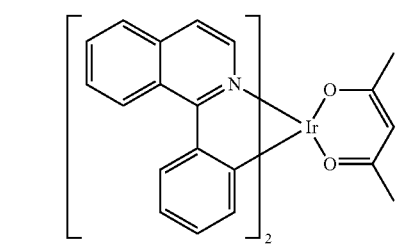
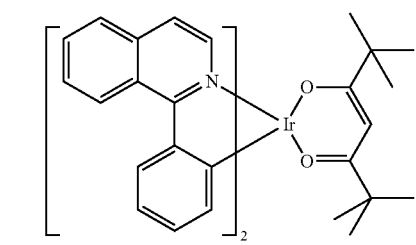
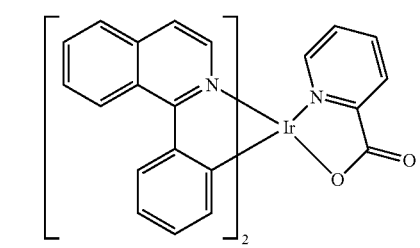
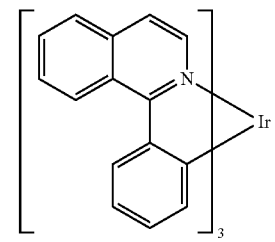
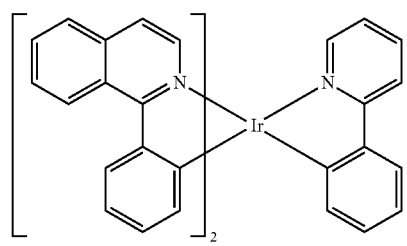
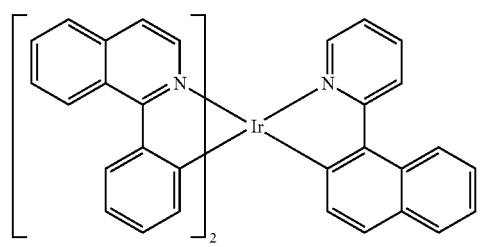
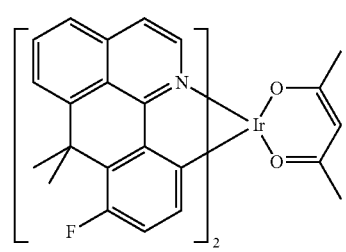
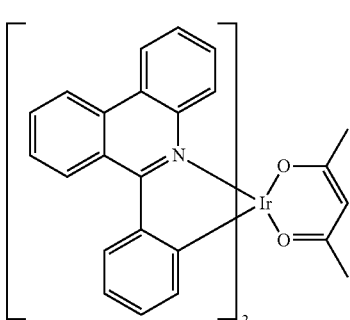
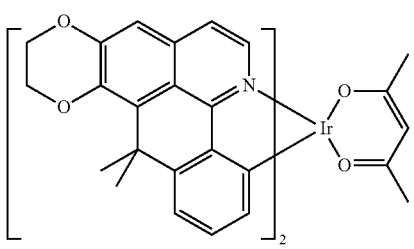

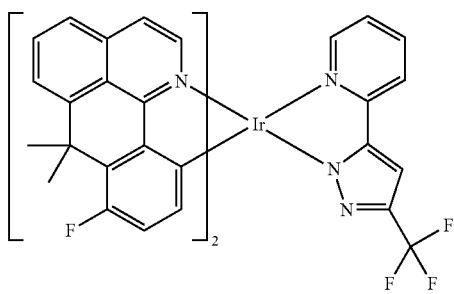
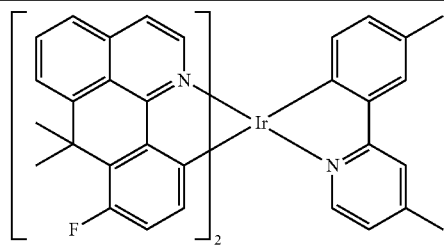
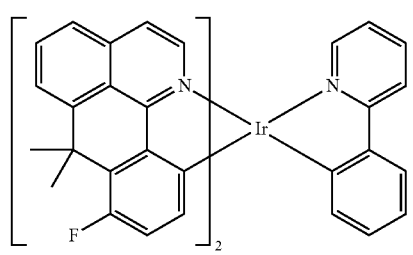
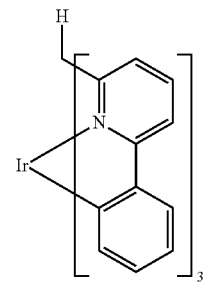
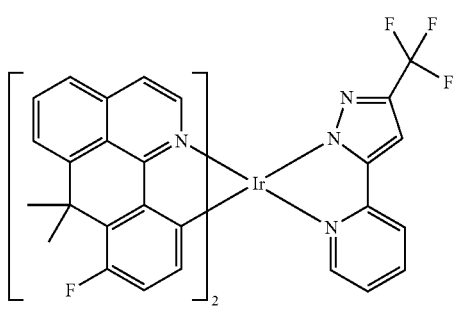
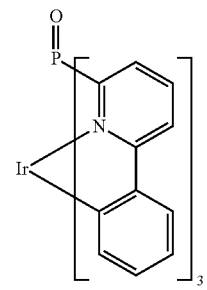
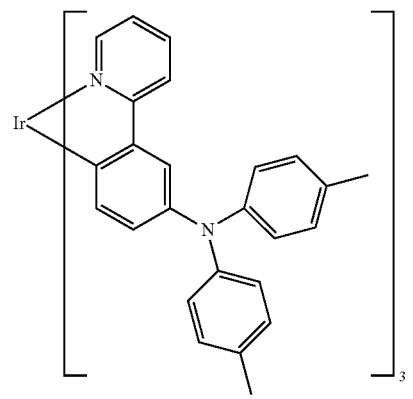
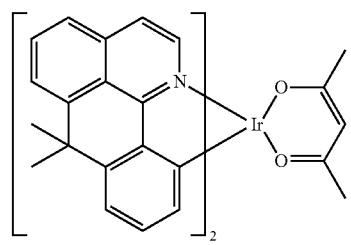
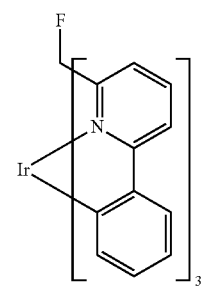
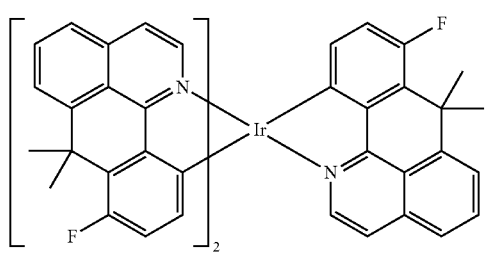
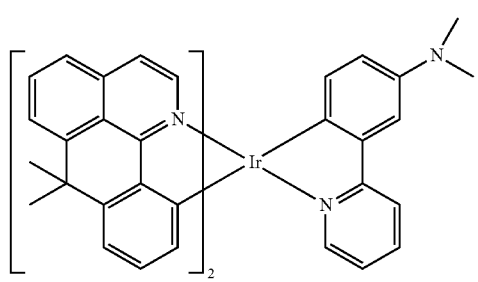

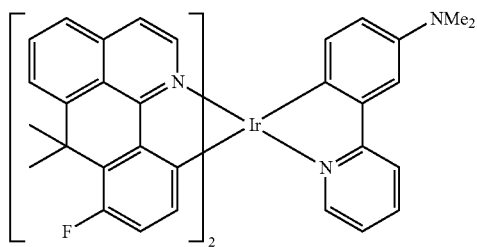
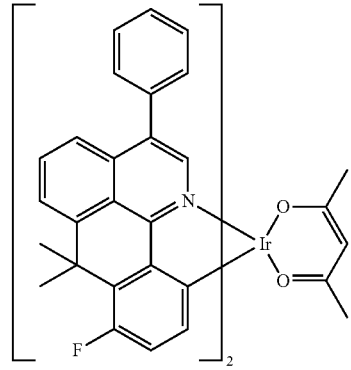
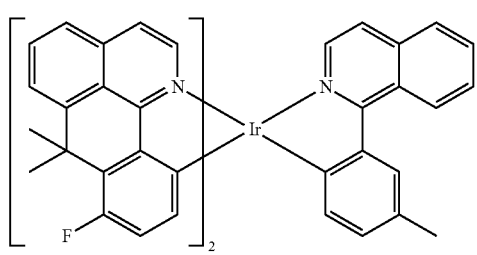
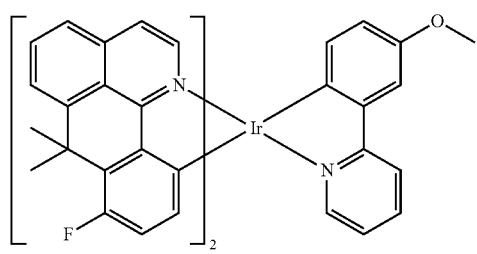
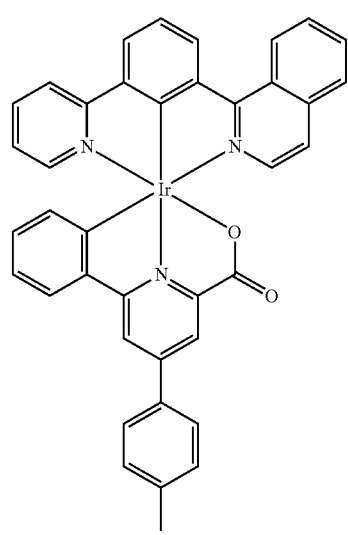
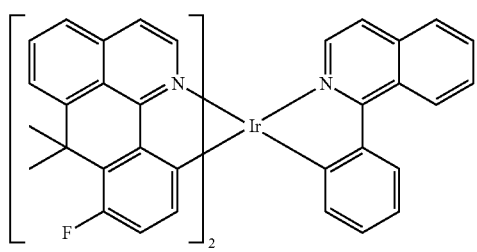
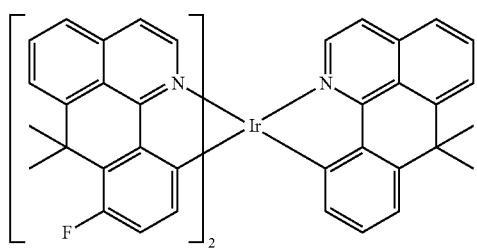
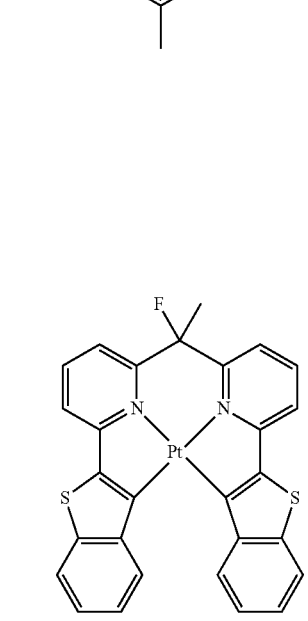

-continued
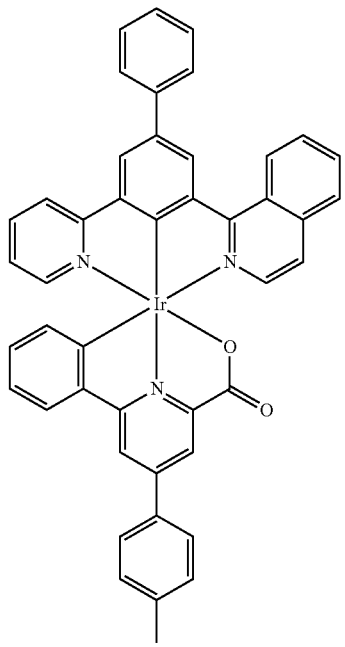
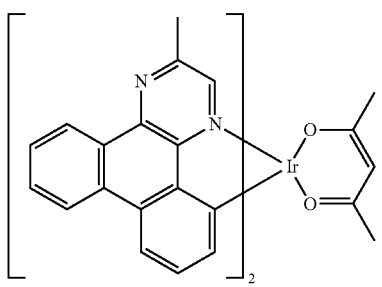
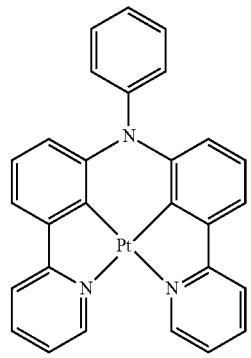
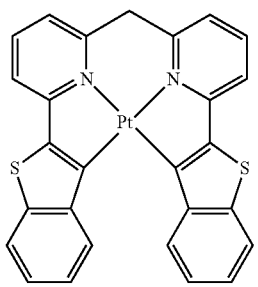
-continued
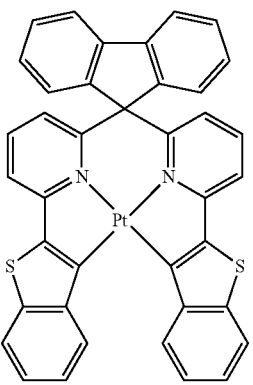
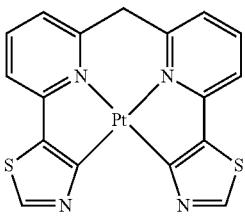
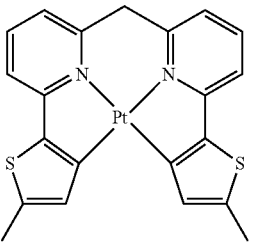
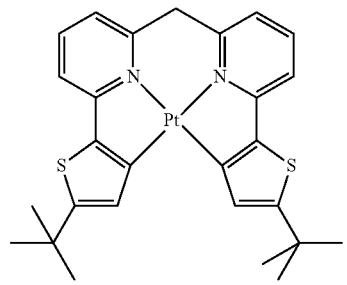
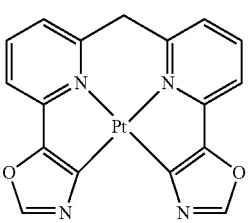

95
-continued
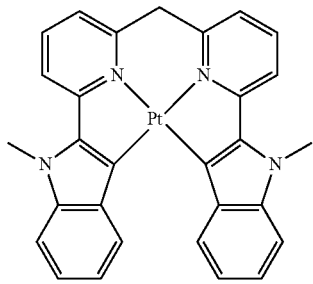
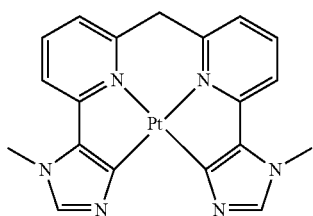
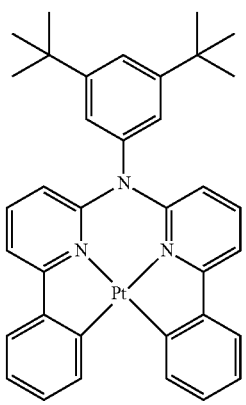
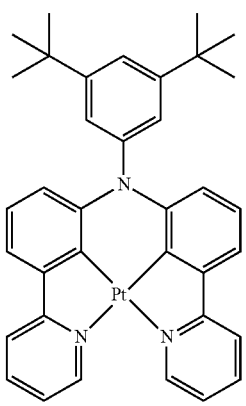
96
-continued
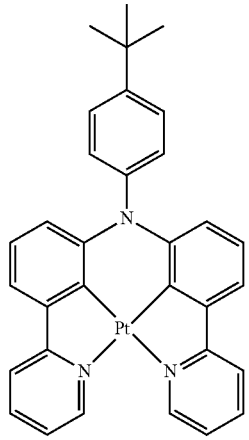
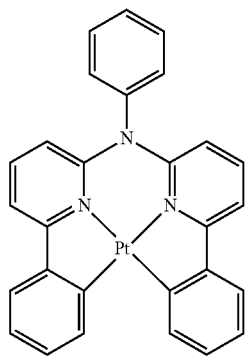
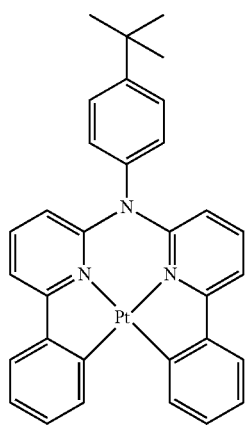
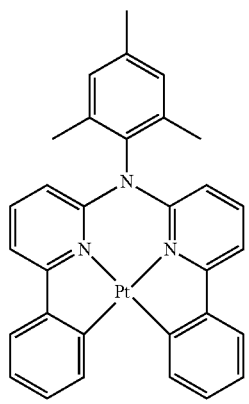

| 97 -continued | 98 -continued |
|---|---|
| 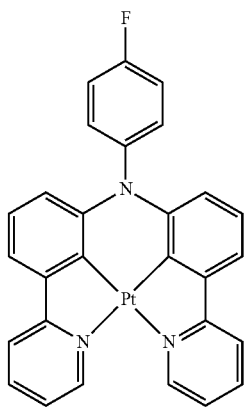 | 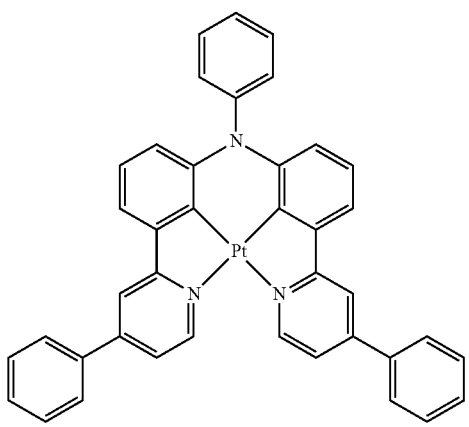 |
| 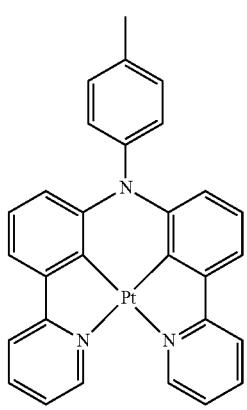 | 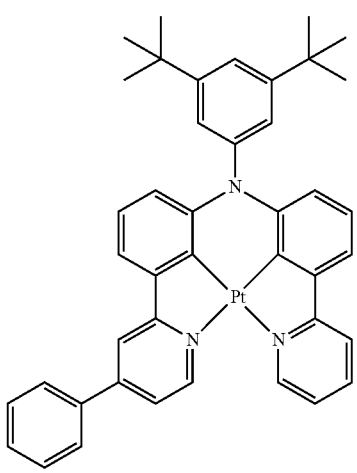 |
| 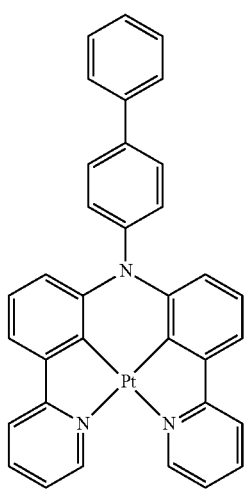 | 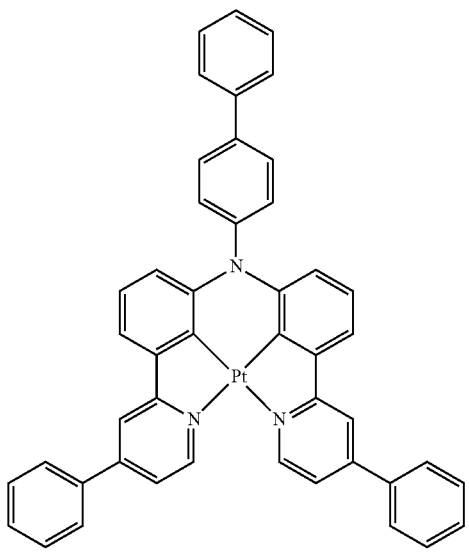 |

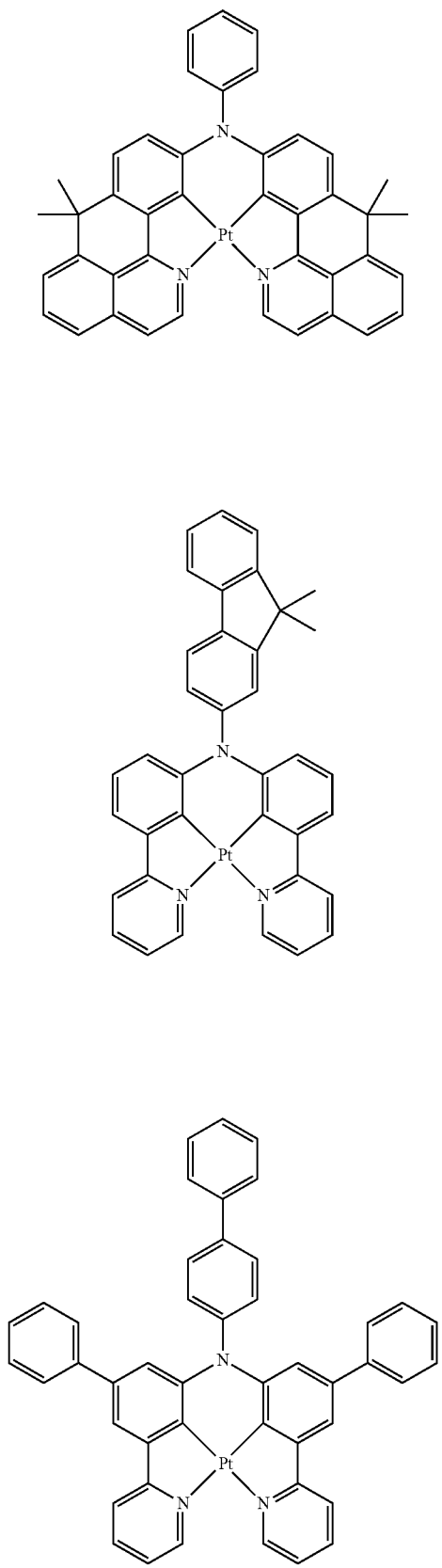
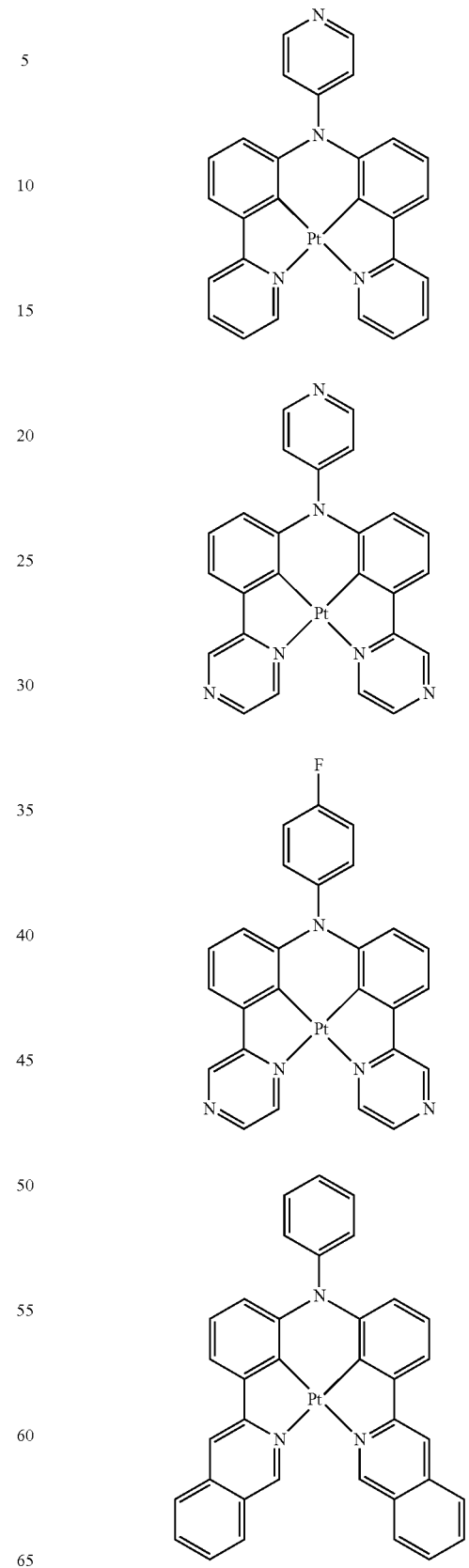

| 101 -continued | 102 -continued |
|---|---|
| 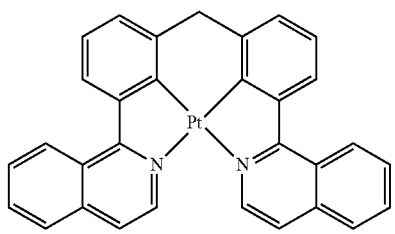 | 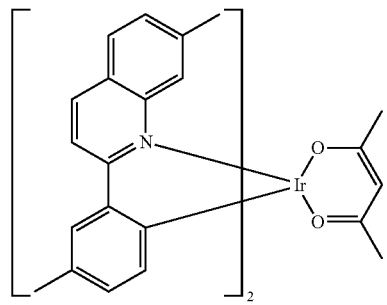 |
| 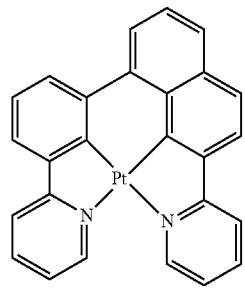 | 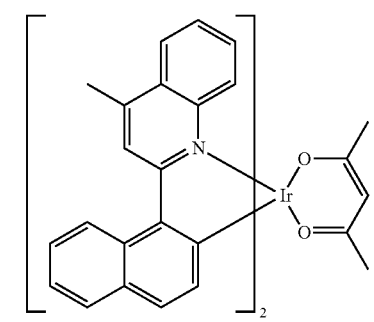 |
| 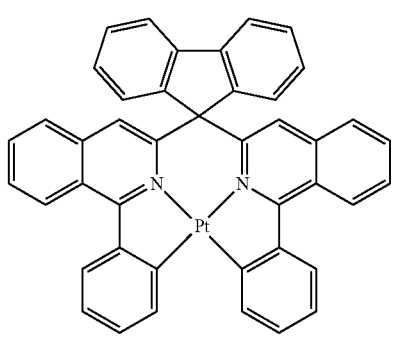 | 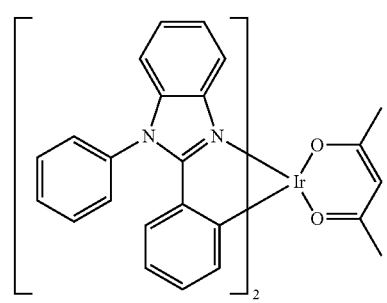 |
| 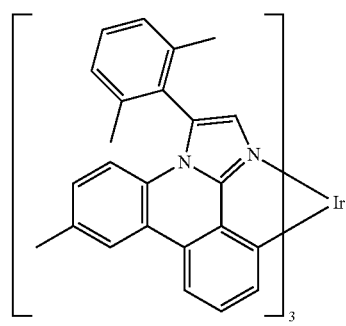 | 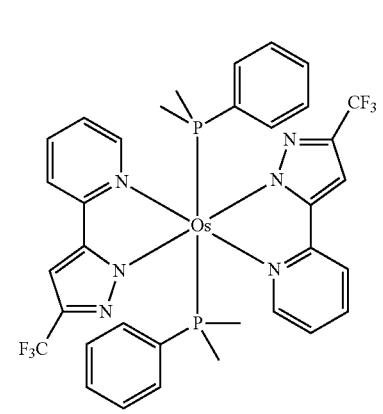 |
| 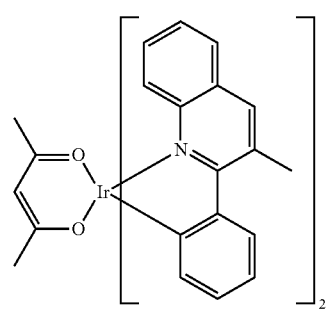 | 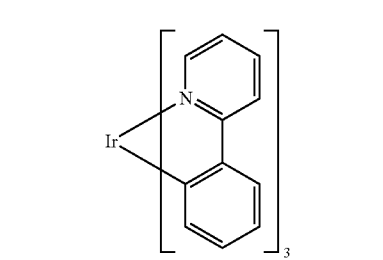 |

| 103 -continued | 104 -continued |
|---|---|
| 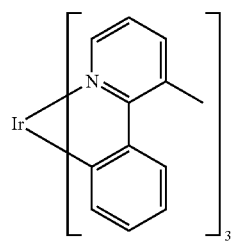 | 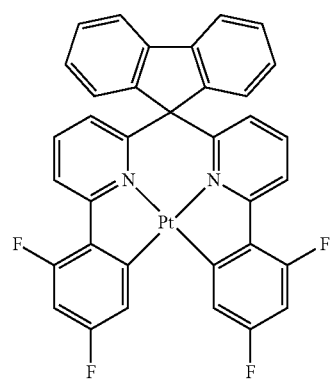 |
| 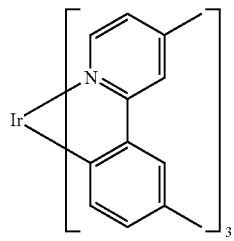 | 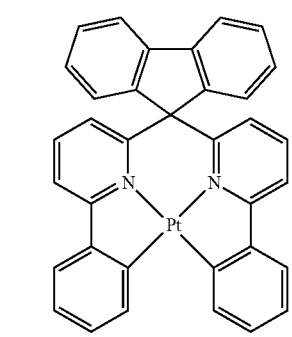 |
| 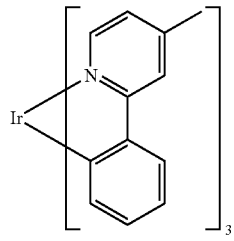 | |
| 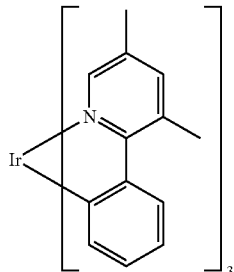 | 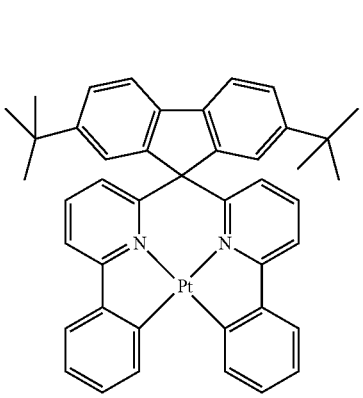 |
| 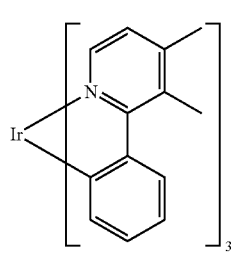 | |
| 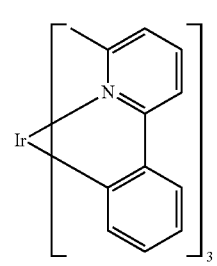 | 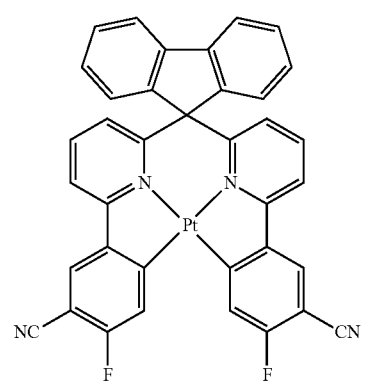 |

105
-continued
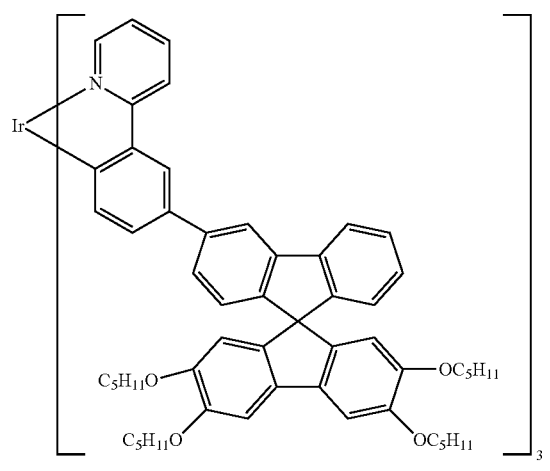
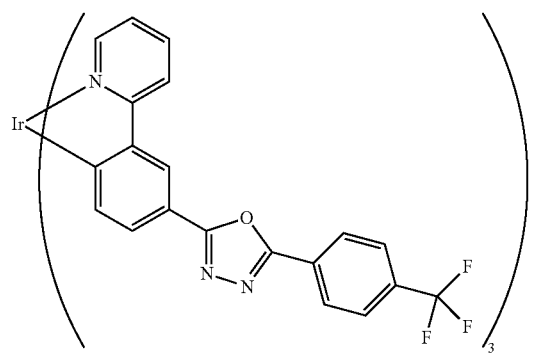
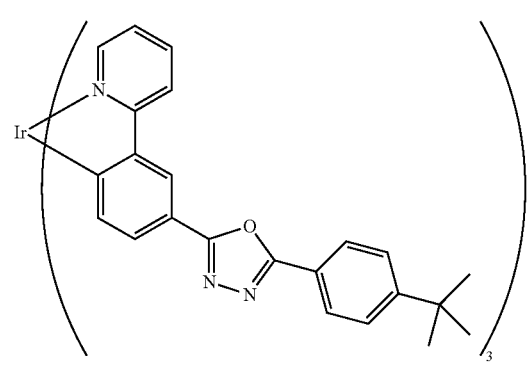
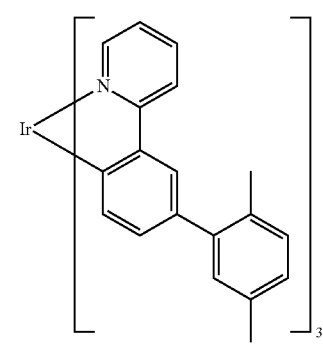
106
-continued
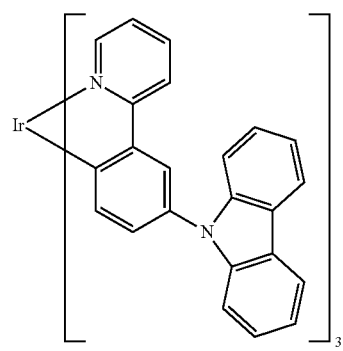
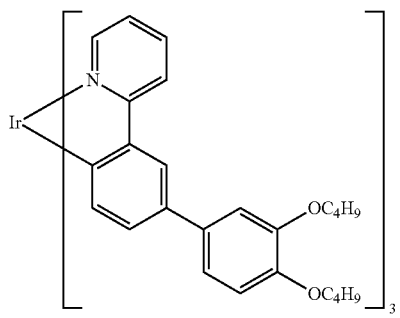
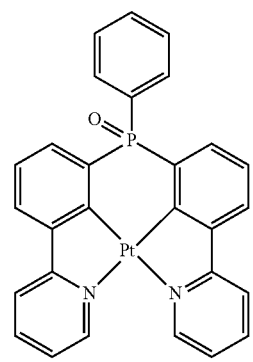
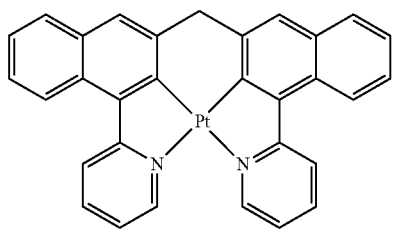

107
-continued
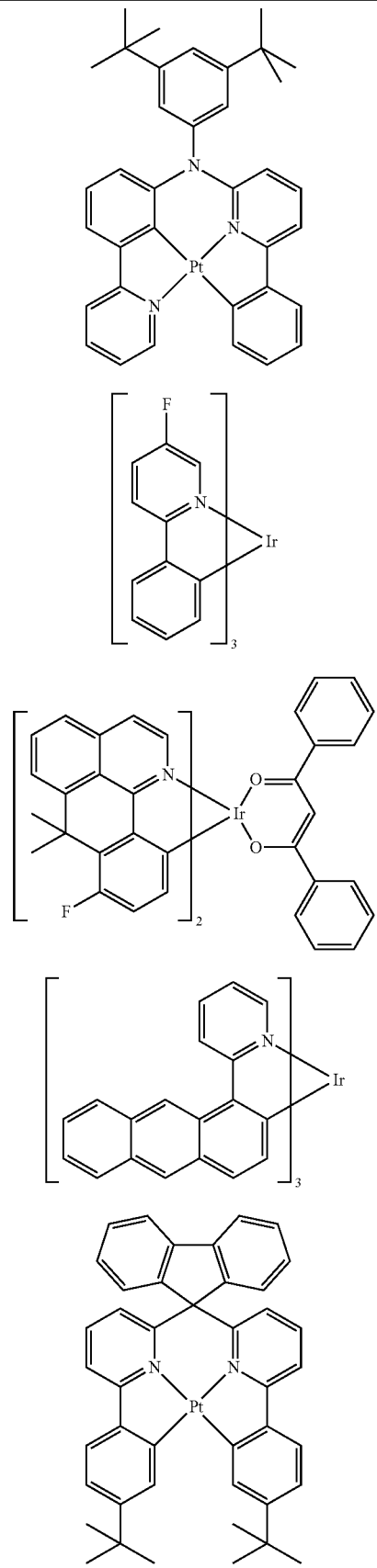
108
-continued
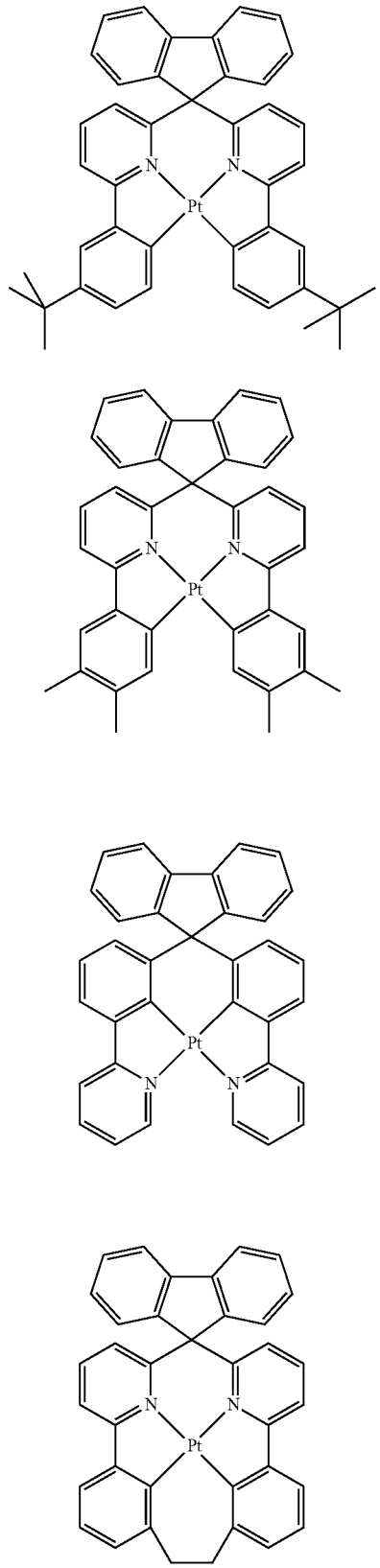

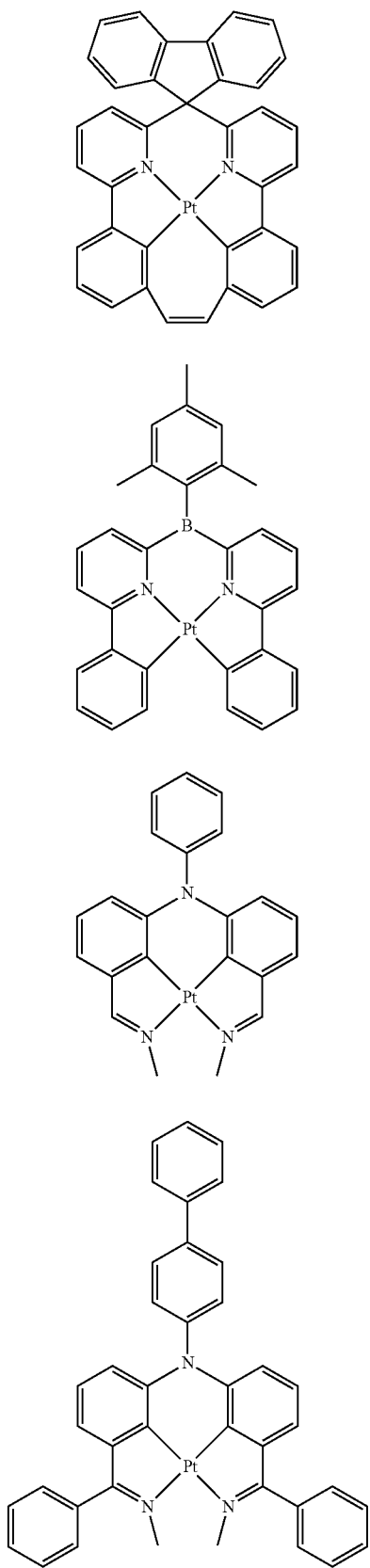
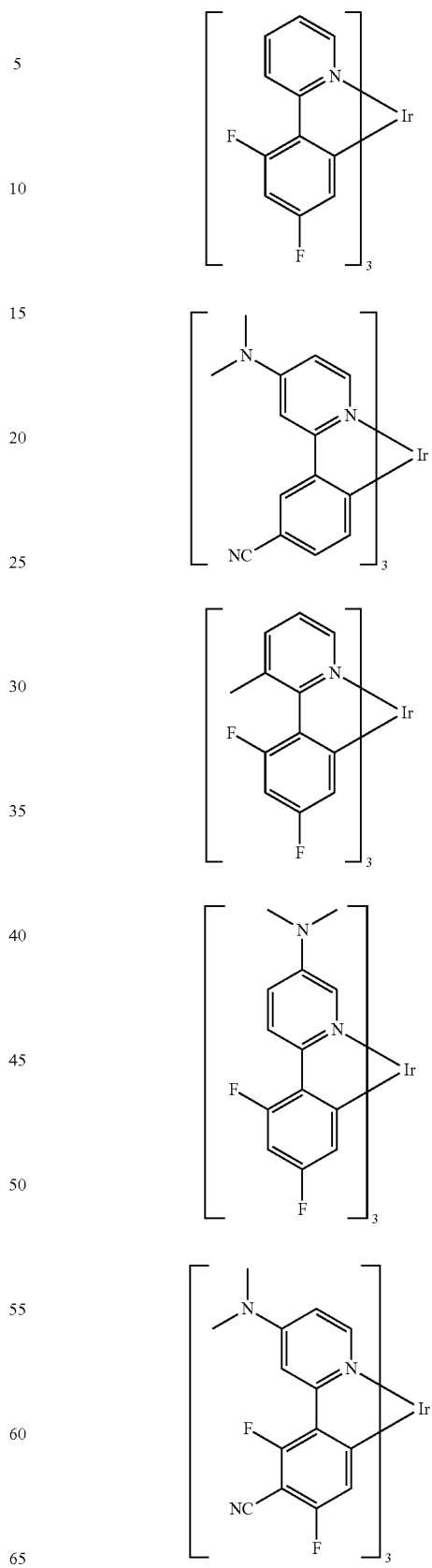

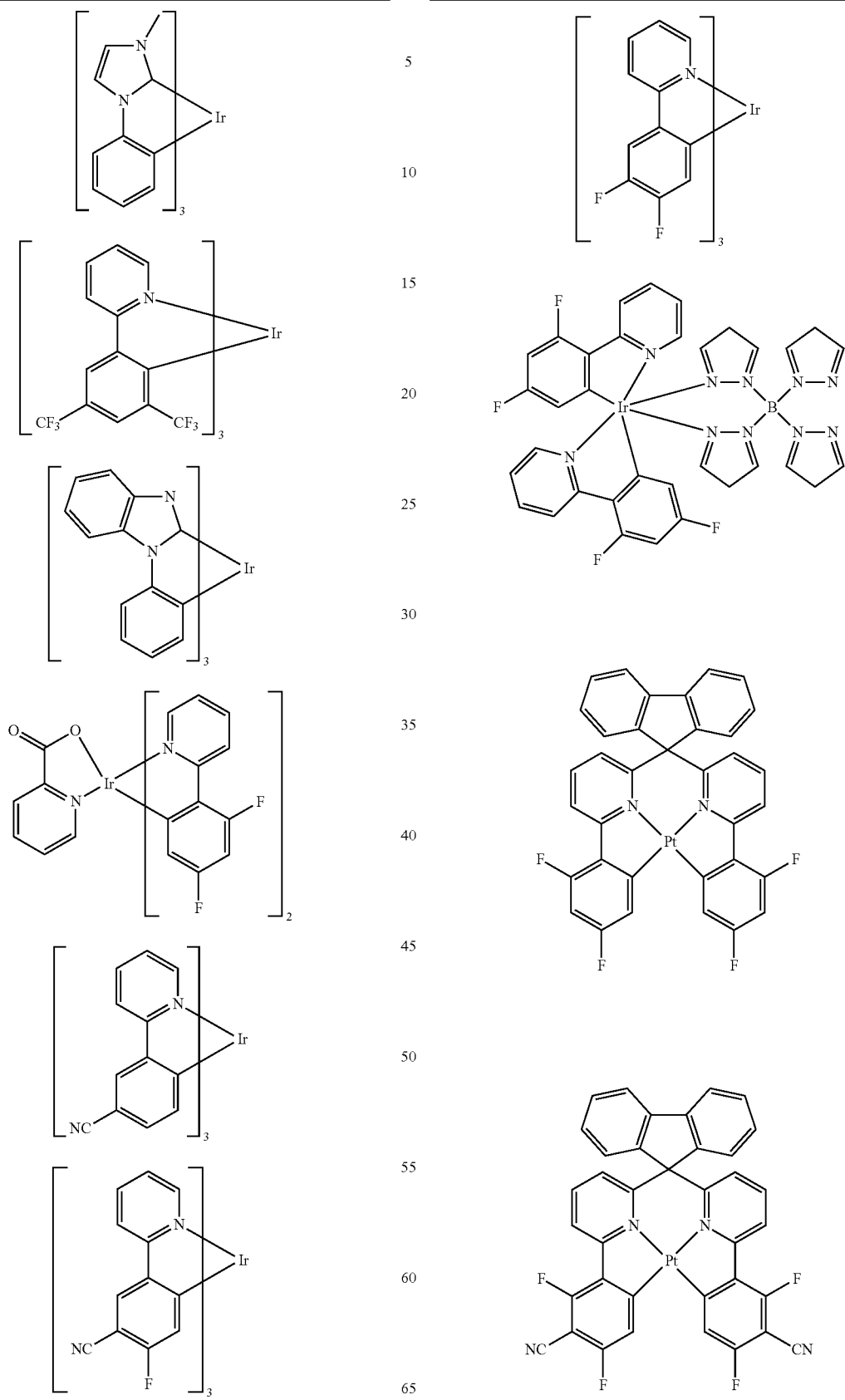

-continued
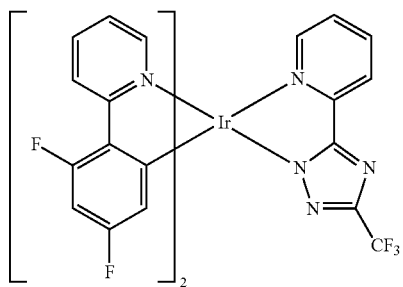
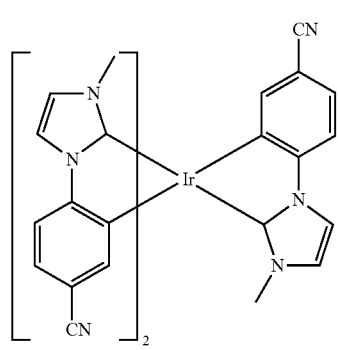
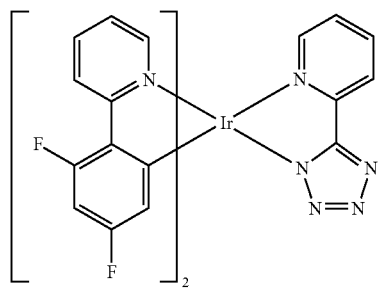
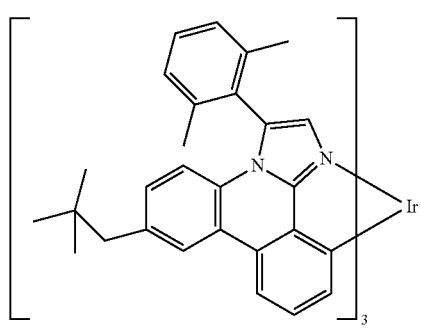
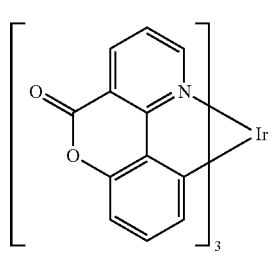
-continued
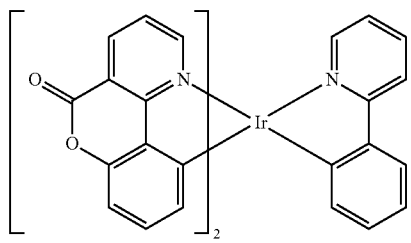
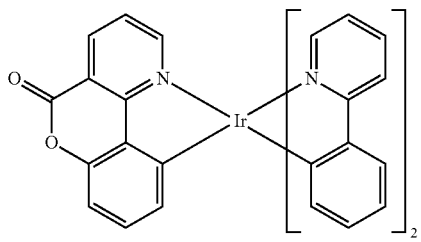
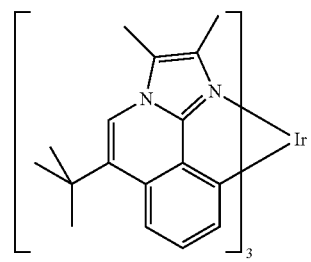
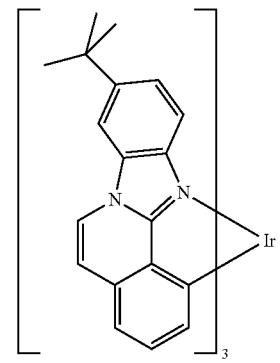
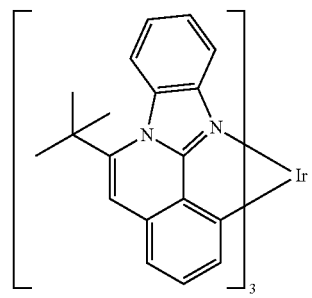

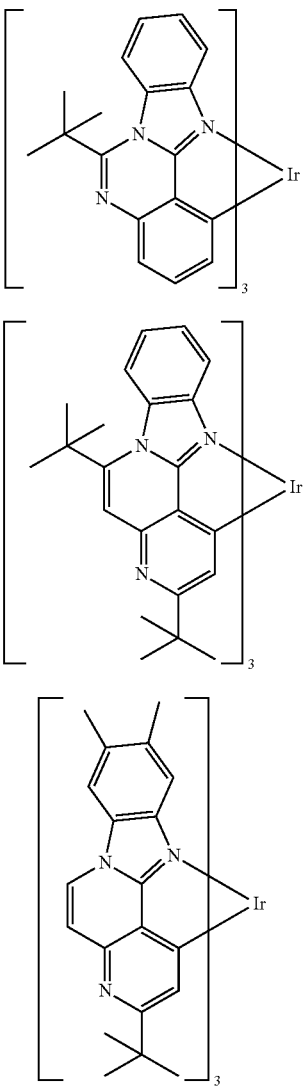

Preferred fluorescent emitters are selected from the class of the arylamines. An arylamine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1 position or 1,6 positions. Further preferred emitters are indenofluorenamines or -fluorenediamines, for example according to WO 2006/108497 or WO 2006/122630, benzoindenofluorenamines or -fluorenediamines, for example according to WO 2008/006449, and dibenzoindenofluorenamines or -fluorenediamines, for example according to WO 2007/140847, and the indenofluorene derivatives having fused aryl groups disclosed in WO 2010/012328. Likewise preferred are the pyrenearylamines disclosed in WO 2012/048780 and the as yet unpublished EP 12004426.8. Likewise preferred are the benzoindenofluorenamines disclosed in the as yet unpublished EP 12006239.3 and the benzofluorenamines disclosed in the as yet unpublished EP 13000012.8.

Useful matrix materials, preferably for fluorescent emitters, as well as the compounds of the invention, are materials from various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent emitters are, as well as the compounds of the invention, aromatic amines, especially triarylamines, for example according to US 2005/0069729, carbazole derivatives (e.g. CBP, N,N-biscarbazolylbiphenyl) or compounds according to WO 2005/039246, US 2005/0069729, JP 2004/288381, EP 1205527 or WO 2008/086851, bridged carbazole derivatives, for example according to WO 2011/088877 and WO 2011/128017, indenocarbazole derivatives, for example according to WO 2010/136109 and WO 2011/000455, azacarbazole derivatives, for example according to EP 1617710, EP 1617711, EP 1731584, JP 2005/347160, indolocarbazole derivatives, for example according to WO 2007/063754 or WO 2008/056746, ketones, for example according to WO 2004/093207 or WO 2010/006680, phosphine oxides, sulfoxides and sulfones, for example according to WO 2005/003253, oligophenylenes, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, aluminum complexes, e.g. BAlq, diazasilole derivatives and tetraazasilole derivatives, for example according to WO 2010/054729, diazaphosphole derivatives, for example according to WO 2010/054730, and aluminum complexes, e.g. BAlQ.

Suitable charge transport materials as usable in the hole injection or hole transport layer or electron blocker layer or in the electron transport layer of the electronic device of the invention are, as well as the compounds of the invention, for example, the compounds disclosed in Y. Shirota et al., Chem. Rev. 2007, 107(4), 953-1010, or other materials as used in these layers according to the prior art.

Materials used for the electron transport layer may be any materials as used according to the prior art as electron transport materials in the electron transport layer. Especially suitable are aluminum complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the organic electroluminescent device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is appropriately (according to the application) structured, contact-connected and finally sealed, since the lifetime of the devices of the invention is shortened in the presence of water and/or air.

In a preferred embodiment, the organic electroluminescent device of the invention is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an organic electroluminescent device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

WORKING EXAMPLES

The working examples which follow serve to elucidate the present invention. They should not be interpreted in a restrictive manner.

A) Synthesis Examples

The starting compound 10-bromobenzo[h]quinoline is known from the literature (CAS number [152583-10-3]). A corresponding N-heterocyclic derivative, as further starting compound, is known by CAS [66693-82-1].

119

Benzo[h]quinolin-10-yl(biphenyl-4-yl)(9,9-dimethyl-9H-fluoren-2-yl)amine

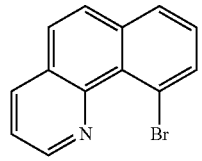  +

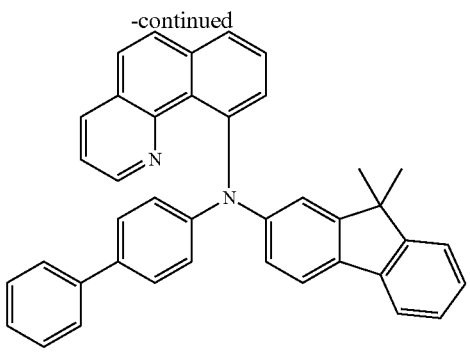
-continued

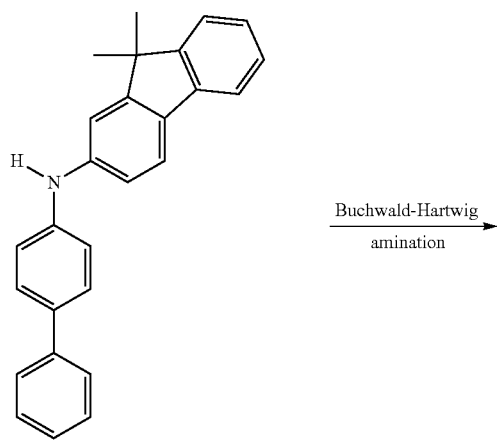

Buchwald-Hartwig amination →

27.1 g of biphenyl-4-yl(9,9-dimethyl-9H-fluoren-2-yl)amine (75 mmol) and 19.4 g of 10-bromobenzo[h]quinoline (75 mmol) are dissolved in 500 mL of toluene. The solution is degassed and saturated with $N_2$. Thereafter, 3.0 mL (3.0 mmol) of a tri-tert-butylphosphine solution and 0.33 g (1.52 mmol) of palladium(II) acetate are added thereto. Subsequently, 11.2 g of sodium tert-butoxide (116 mmol) are added. The reaction mixture is heated to boiling under a protective atmosphere for 5 h. The mixture is subsequently partitioned between toluene and water, and the organic phase is washed twice with water and dried over $Na_2SO_4$ and concentrated by rotary evaporation. After the crude product has been filtered through silica gel with toluene, the remaining residue is recrystallized from heptane/toluene and finally sublimed under high vacuum. The purity is 99.9%; the yield is 28.3 g (70% of theory).

In an analogous manner, the following compounds are prepared:

| | Reactant 1 | Reactant 2 |
|---|---|---|
| 1-2 | [152583-10-3] | |

1-3 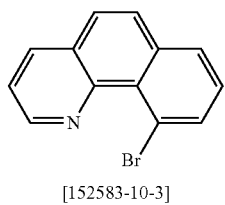 [SMILES: Brc1cccc2ccc3cccnc3c12] 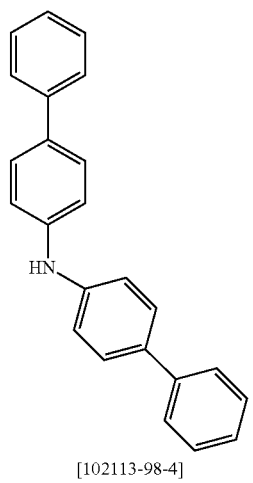
[152583-10-3]   [102113-98-4]
1-4 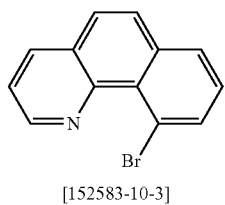 [SMILES: Brc1cccc2ccc3cccnc3c12] 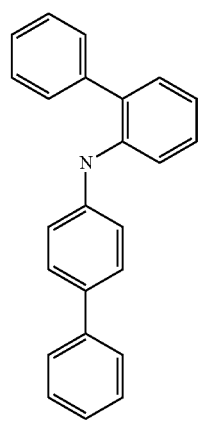 [SMILES: c1ccc(-c2ccc(Nc3ccccc3-c3ccccc3)cc2)cc1]
[152583-10-3]
1-5 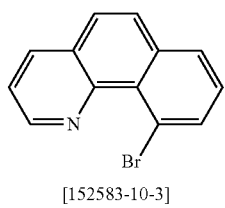 [SMILES: Brc1cccc2ccc3cccnc3c12] 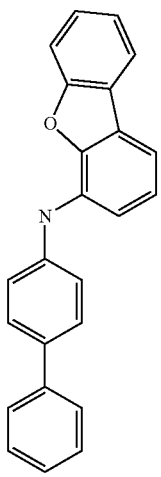 [SMILES: c1ccc(-c2ccc(Nc3cccc4c3oc3ccccc34)cc2)cc1]
[152583-10-3]

1-6 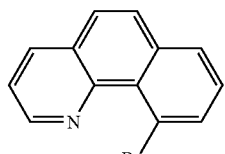 [152583-10-3] 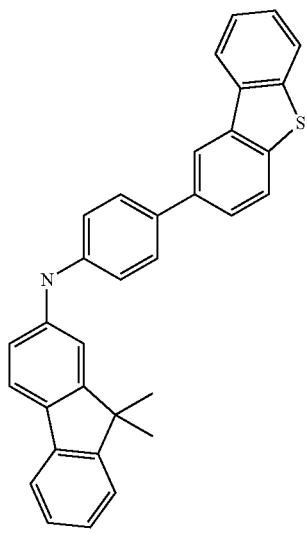 [SMILES: CC1(C)c2ccccc2-c2ccc(Nc3ccc(-c4ccc5sc6ccccc6c5c4)cc3)cc21]
1-7 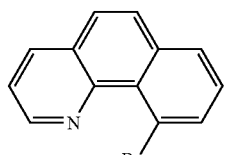 [152583-10-3] 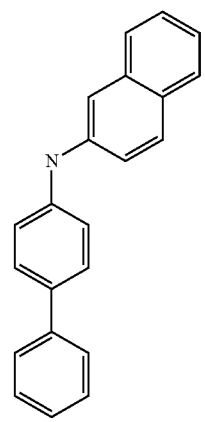 [SMILES: c1ccc(-c2ccc(Nc3ccc4ccccc4c3)cc2)cc1]
1-8 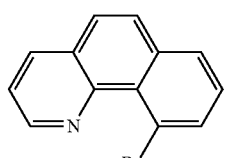 [152583-10-3] 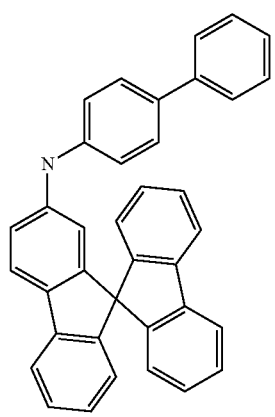 [SMILES: c1ccc(-c2ccc(Nc3ccc4c(c3)C3(c5ccccc5-c5ccccc53)c3ccccc3-4)cc2)cc1]

1-9 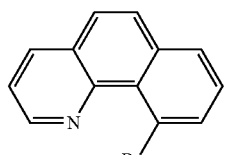
[152583-10-3]
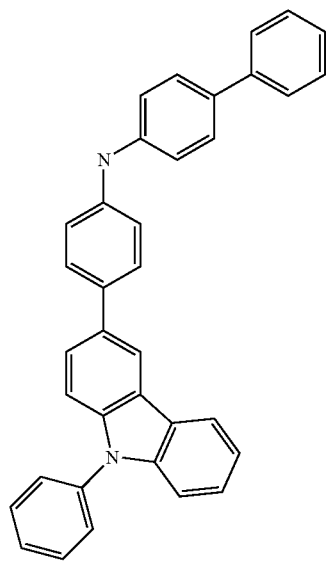 [SMILES: c1ccc(-c2ccc(Nc3ccc(-c4ccc5c(c4)c4ccccc4n5-c4ccccc4)cc3)cc2)cc1]
1-10 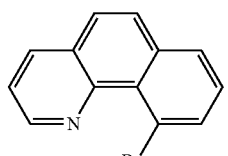
[152583-10-3]
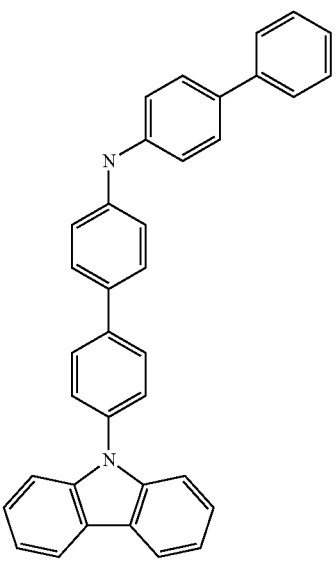 [SMILES: c1ccc(-c2ccc(Nc3ccc(-c4ccc(-n5c6ccccc6c6ccccc65)cc4)cc3)cc2)cc1]
1-11 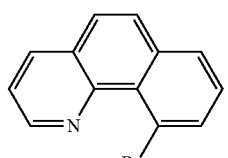
[152583-10-3]
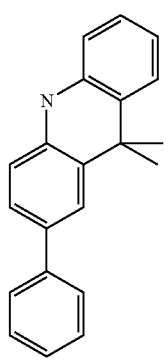 [SMILES: CC1(C)c2ccccc2Nc2ccc(-c3ccccc3)cc21]

1-12 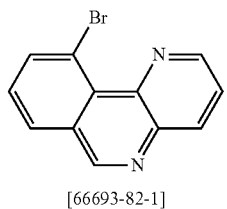 [SMILES: Brc1cccc2cnc3cccnc3c12]
[66693-82-1]
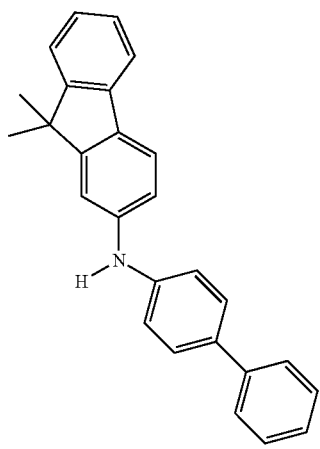
[1386375-27-4]
1-13 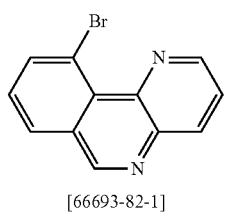 [SMILES: Brc1cccc2cnc3cccnc3c12]
[66693-82-1]
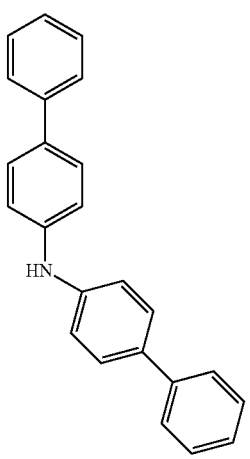
[102113-98-4]
1-14 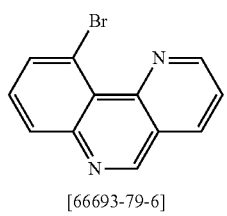 [SMILES: Brc1cccc2ncc3cccnc3c12]
[66693-79-6]
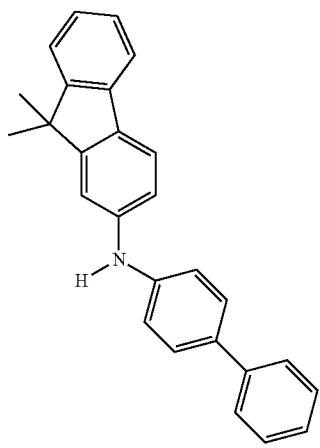
[1386375-27-4]

| | | |
|---|---|---|
| 1-15 | 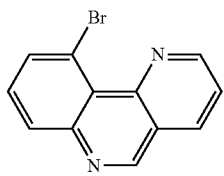\n[66693-79-6] | 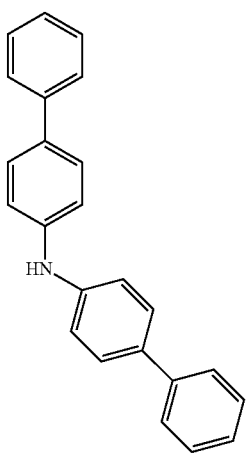\n[102113-98-4] |
| 1-16 | 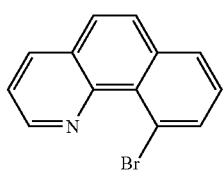\n[152583-10-3] | 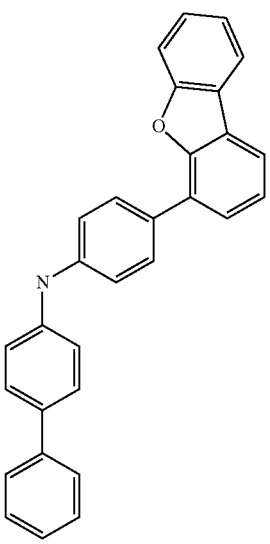 [SMILES: c1ccc(-c2ccc(Nc3ccc(-c4cccc5c4oc4ccccc45)cc3)cc2)cc1] |
| | Product | Yield |
|---|---|---|
| 1-2 | 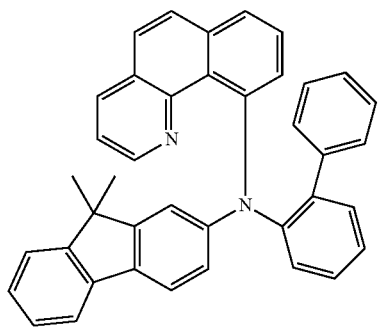 [SMILES: CC1(C)c2ccccc2-c2ccc(N(c3ccccc3-c3ccccc3)c3cccc4ccc5cccnc5c34)cc21] | 68% |

| | | |
|---|---|---|
| 1-3 | 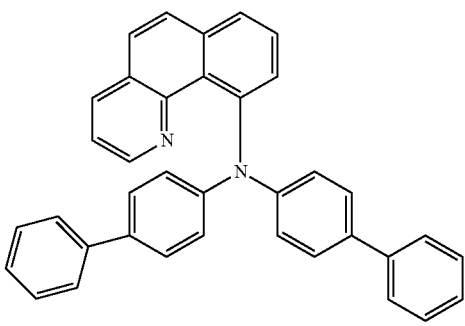 [SMILES: c1ccc(-c2ccc(N(c3ccc(-c4ccccc4)cc3)c3cccc4ccc5cccnc5c34)cc2)cc1] | 78% |
| 1-4 | 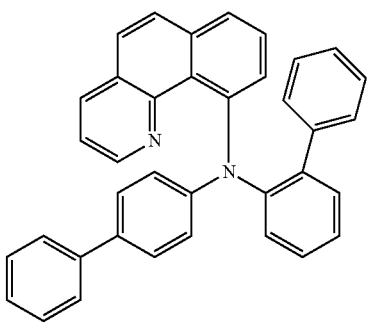 [SMILES: c1ccc(-c2ccc(N(c3ccccc3-c3ccccc3)c3cccc4ccc5cccnc5c34)cc2)cc1] | 74% |
| 1-5 | 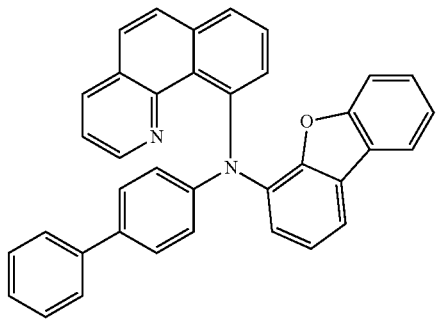 [SMILES: c1ccc(-c2ccc(N(c3cccc4c3oc3ccccc34)c3cccc4ccc5cccnc5c34)cc2)cc1] | 78% |
| 1-6 | 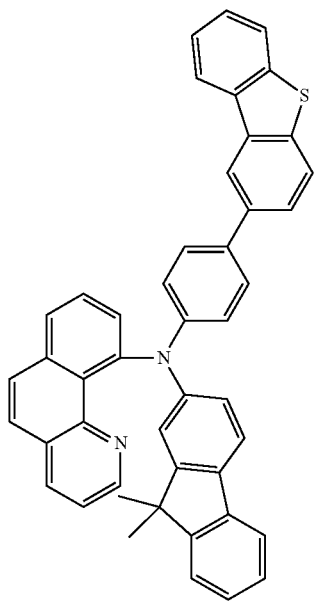 [SMILES: CC1(C)c2ccccc2-c2ccc(N(c3ccc(-c4ccc5sc6ccccc6c5c4)cc3)c3cccc4ccc5cccnc5c34)cc21] | 62% |

| | | |
|---|---|---|
| 1-7 | 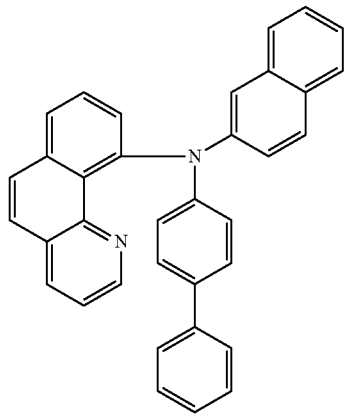 [SMILES: c1ccc(-c2ccc(N(c3ccc4ccccc4c3)c3cccc4ccc5cccnc5c34)cc2)cc1] | 75% |
| 1-8 | 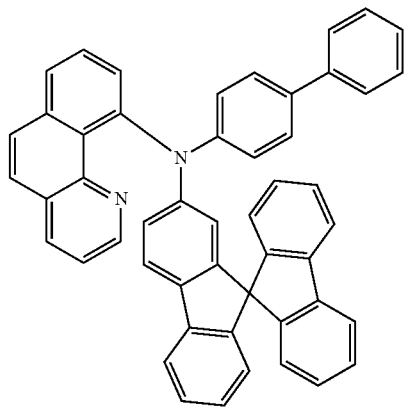 [SMILES: c1ccc(-c2ccc(N(c3ccc4c(c3)C3(c5ccccc5-c5ccccc53)c3ccccc3-4)c3cccc4ccc5cccnc5c34)cc2)cc1] | 68% |
| 1-9 | 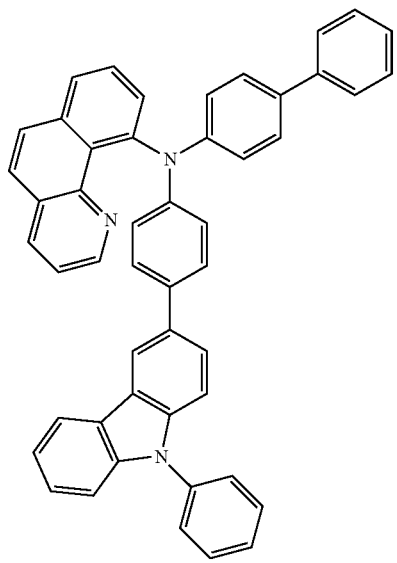 [SMILES: c1ccc(-c2ccc(N(c3ccc(-c4ccc5c(c4)c4ccccc4n5-c4ccccc4)cc3)c3cccc4ccc5cccnc5c34)cc2)cc1] | 71% |

| | | |
|---|---|---|
| 1-10 | 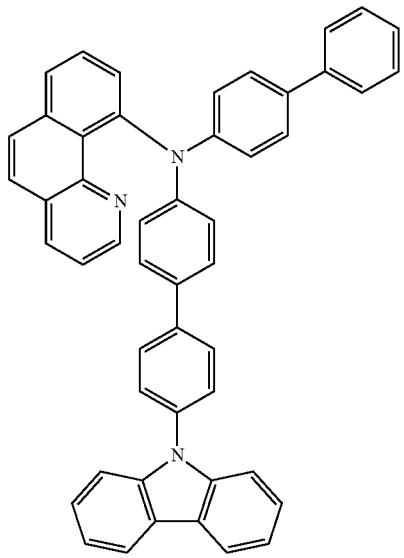 [SMILES: c1ccc(-c2ccc(N(c3ccc(-c4ccc(-n5c6ccccc6c6ccccc65)cc4)cc3)c3cccc4ccc5cccnc5c34)cc2)cc1] | 75% |
| 1-11 | 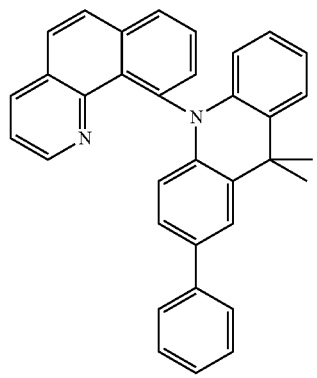 [SMILES: CC1(C)c2ccccc2N(c2cccc3ccc4cccnc4c23)c2ccc(-c3ccccc3)cc21] | 70% |
| 1-12 | 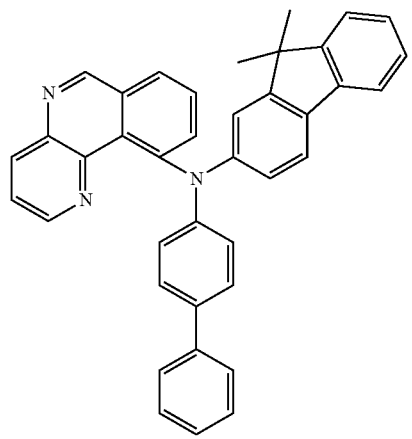 | 56% |

| | | |
|---|---|---|
| 1-13 | 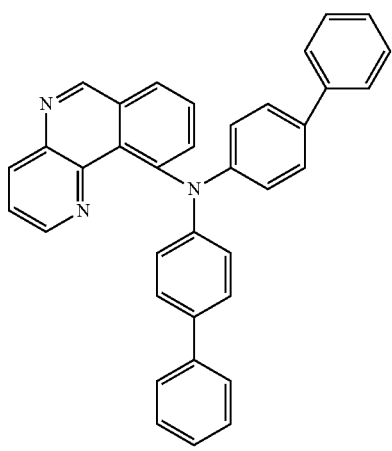 [SMILES: c1ccc(-c2ccc(N(c3ccc(-c4ccccc4)cc3)c3cccc4cnc5cccnc5c34)cc2)cc1] | 63% |
| 1-14 | 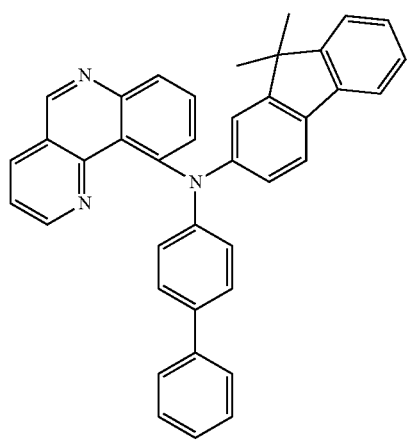 | 58% |
| 1-15 | 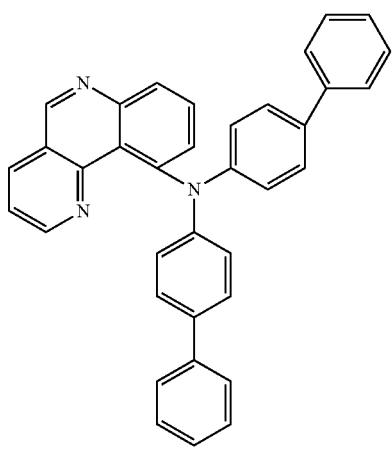 | 67% |

| | | |
|---|---|---|
| 1-16 | 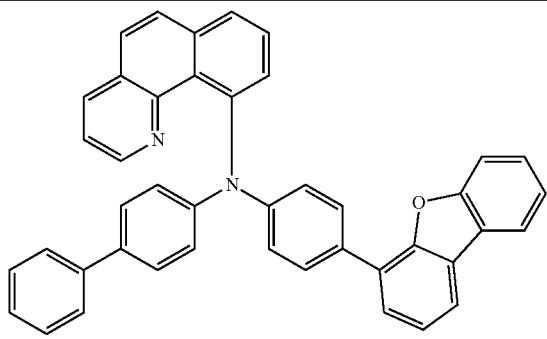 | 78% |

Example 2-1

(4-Benzo[h]quinolin-10-ylphenyl)biphenyl-4-yl(9,9-dimethyl-9H-fluoren-2-yl)amine

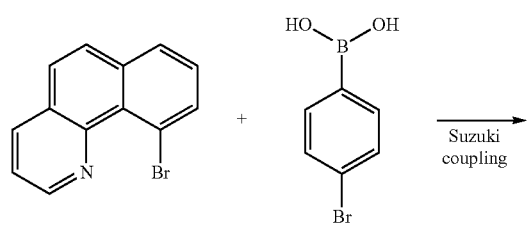

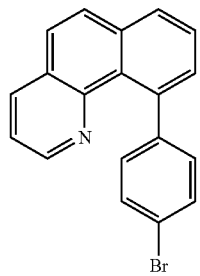

15.47 g (75 mmol) of 4-bromobenzeneboronic acid, 19.4 g of 10-bromobenzo[h]quinoline (75 mmol) and 110 mL of a 2M NaHCO$_3$-containing aqueous solution (163 mmol) are suspended in 500 mL of dimethoxyethane. 3.0 g (3.45 mmol) of tetrakis(triphenylphosphine)palladium(0) are added to this suspension, and the reaction mixture is heated under reflux for 22 h. After cooling, the organic phase is removed, filtered through silica gel, washed four times with 400 mL of water and then concentrated to dryness. After filtration of the crude product through silica gel with heptane/toluene (10:1), 39 g (71%) of 10-(4-bromophenyl)benzo[h]quinoline are obtained.

In an analogous manner, the following compounds are prepared:

| | Reactant 1 | Reactant 2 |
|---|---|---|
| Int-2-2 | 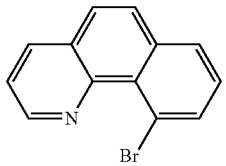<br>[152583-10-3] | 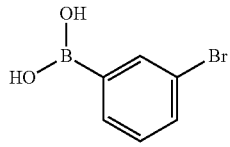 |
| Int-2-3 | 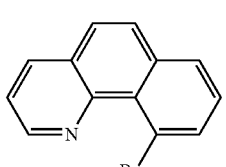<br>[152583-10-3] | 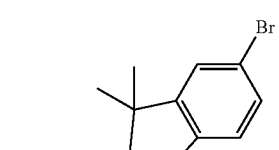 |

| | | |
|---|---|---|
| Int-2-4 | 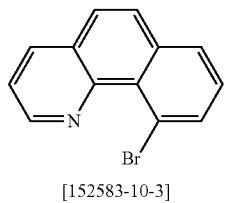 [SMILES: Brc1cccc2ccc3cccnc3c12]<br>[152583-10-3] | 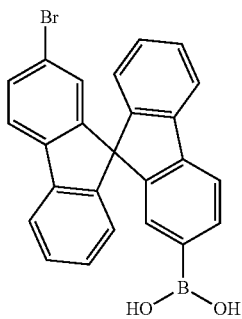 [SMILES: OB(O)c1ccc2c(c1)C1(c3ccccc3-c3ccc(Br)cc31)c1ccccc1-2] |
| Int-2-5 | 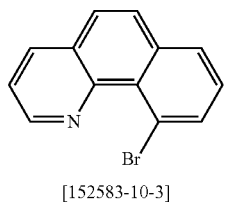 [SMILES: Brc1cccc2ccc3cccnc3c12]<br>[152583-10-3] | 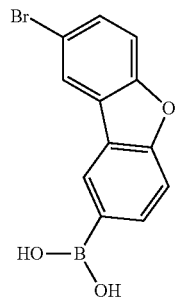 |
| Int-2-6 | 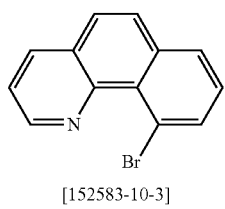 [SMILES: Brc1cccc2ccc3cccnc3c12]<br>[152583-10-3] | 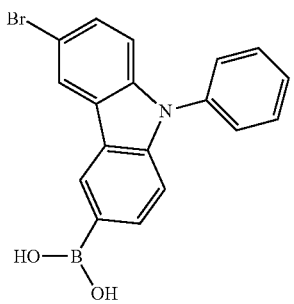 [SMILES: OB(O)c1ccc2c(c1)c1cc(Br)ccc1n2-c1ccccc1] |
| Int-2-7 | 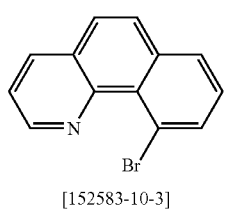<br>[152583-10-3] | 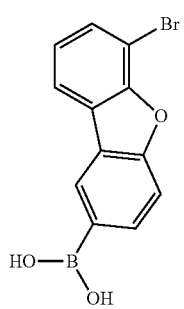 |
| Int-2-8 | 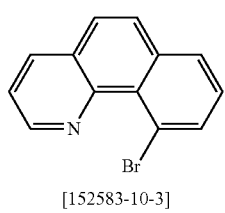 [SMILES: Brc1cccc2ccc3cccnc3c12]<br>[152583-10-3] | 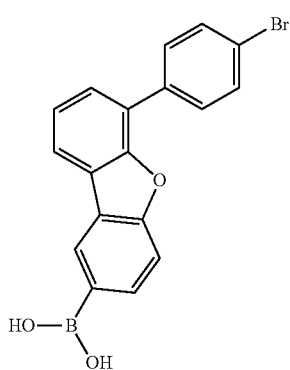 [SMILES: OB(O)c1ccc2oc3c(-c4ccc(Br)cc4)cccc3c2c1] |

-continued

| | Product | Yield |
|---|---|---|
| Int-2-2 | | 58% |
| Int-2-3 | | 49% |
| Int-2-4 | | 51% |
| Int-2-5 | | 56% |
| Int-2-6 | | 56% |

| | | |
|---|---|---|
| Int-2-7 | 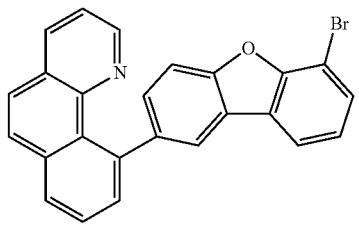 [SMILES: Brc1cccc2c1oc1ccc(-c3cccc4ccc5cccnc5c34)cc12] | 54% |
| Int-2-8 | 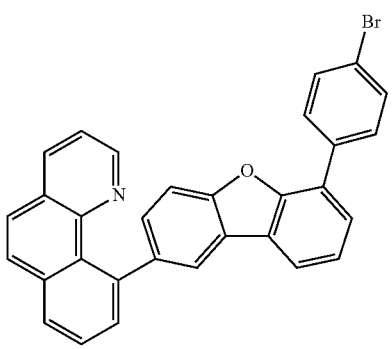 [SMILES: Brc1ccc(-c2cccc3c2oc2ccc(-c4cccc5ccc6cccnc6c45)cc23)cc1] | 49% |

Example 3-1

(4-Benzo[h]quinolin-10-ylphenyl)biphenyl-4-yl(9,9-dimethyl-9H-fluoren-2-yl)amine

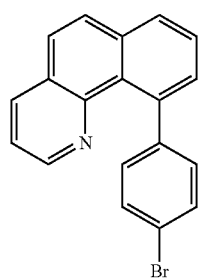 Buchwald-Hartwig amination → 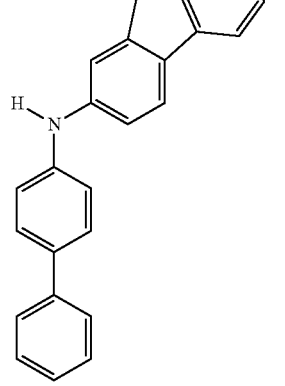

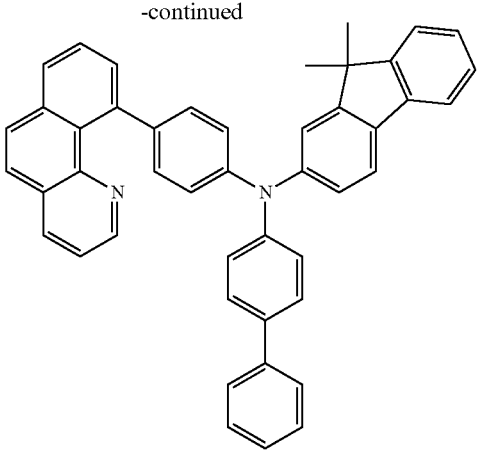

16.27 g of biphenyl-2-yl(9,9-dimethyl-9H-fluoren-2-yl)amine (45 mmol) and 15.0 g of product from example 2-1 (45 mol) are dissolved in 300 mL of toluene. The solution is degassed and saturated with $N_2$. Thereafter, 2.4 g (2.9 mmol) of a tri-tert-butylphosphine solution and 0.20 g (0.9 mmol) of palladium(II) acetate are added thereto. Subsequently, 6.68 g of sodium tert-butoxide (67.5 mmol) are added. The reaction mixture is heated to boiling under a protective atmosphere for 16 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene and finally sublimed under high vacuum. The purity is 99.9%. The yield is 20 g (60% of theory).

In an analogous manner, the following compounds are prepared:

| | Reactant 1 | Reactant 2 |
|---|---|---|
| 3-2 | 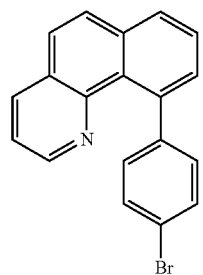 [SMILES: Brc1ccc(-c2cccc3ccc4cccnc4c23)cc1] | 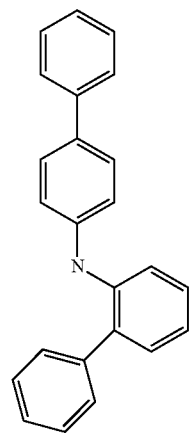 [SMILES: c1ccc(-c2ccc(Nc3ccccc3-c3ccccc3)cc2)cc1] |
| 3-3 | 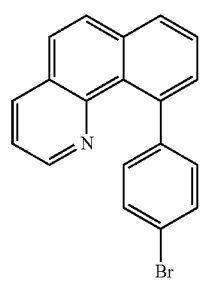 [SMILES: Brc1ccc(-c2cccc3ccc4cccnc4c23)cc1] | 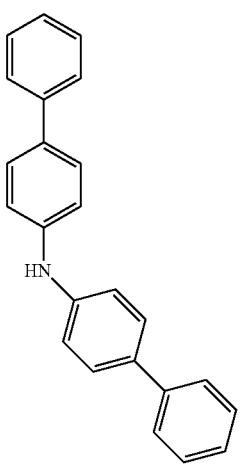 [102113-98-4] |
| 3-4 | 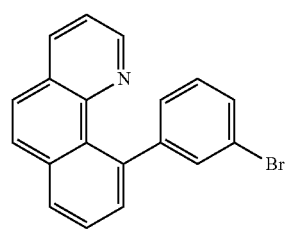 [SMILES: Brc1cccc(-c2cccc3ccc4cccnc4c23)c1] | 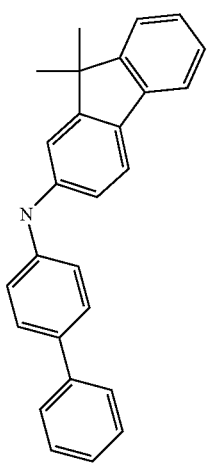 [SMILES: CC1(C)c2ccccc2-c2ccc(Nc3ccc(-c4ccccc4)cc3)cc21] |

3-5 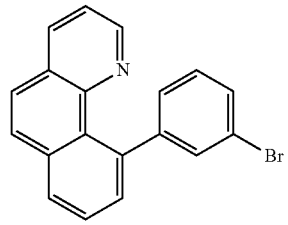 [SMILES: Brc1cccc(-c2cccc3ccc4cccnc4c23)c1] 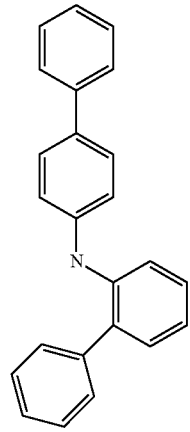 [SMILES: c1ccc(-c2ccc(Nc3ccccc3-c3ccccc3)cc2)cc1]
3-6 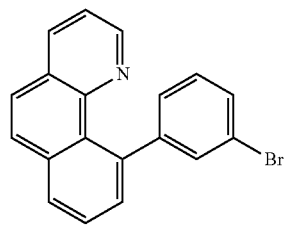 [SMILES: Brc1cccc(-c2cccc3ccc4cccnc4c23)c1] 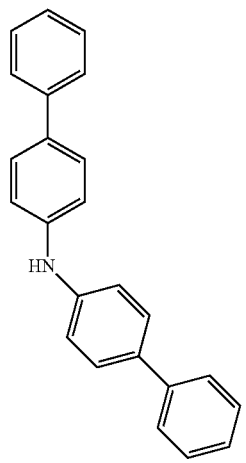
[102113-98-4]
3-7 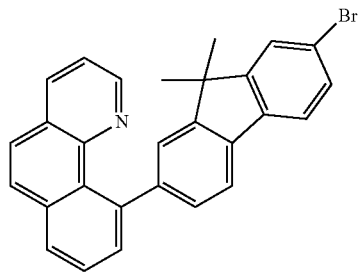 [SMILES: CC1(C)c2cc(Br)ccc2-c2ccc(-c3cccc4ccc5cccnc5c34)cc21] 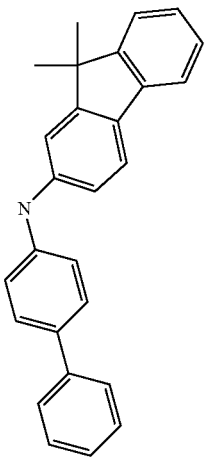 [SMILES: CC1(C)c2ccccc2-c2ccc(Nc3ccc(-c4ccccc4)cc3)cc21]

-continued
3-8 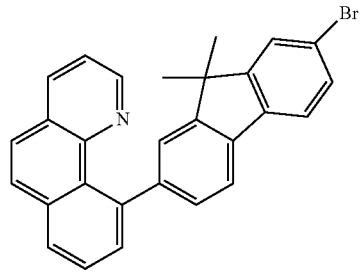 [SMILES: CC1(C)c2cc(Br)ccc2-c2ccc(-c3cccc4ccc5cccnc5c34)cc21] 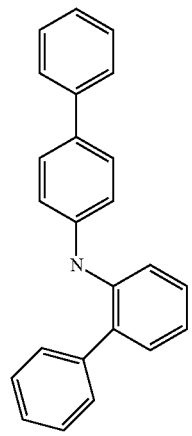 [SMILES: c1ccc(-c2ccc(Nc3ccccc3-c3ccccc3)cc2)cc1]
3-9 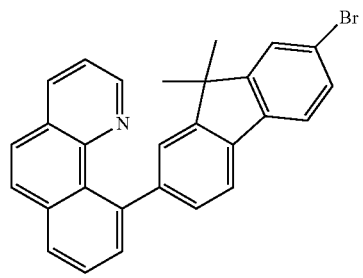 [SMILES: CC1(C)c2cc(Br)ccc2-c2ccc(-c3cccc4ccc5cccnc5c34)cc21] 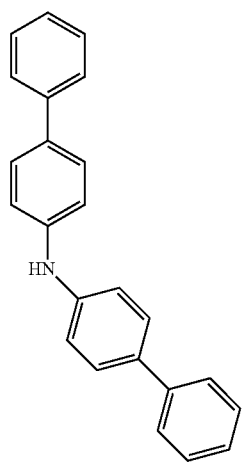
[102113-98-4]
3-10 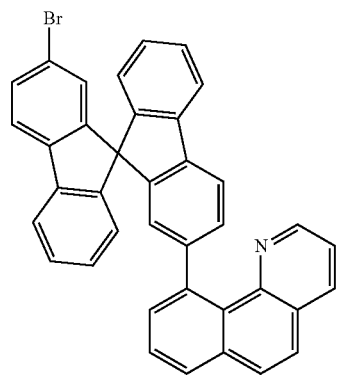 [SMILES: Brc1ccc2c(c1)C1(c3ccccc3-2)c2ccccc2-c2ccc(-c3cccc4ccc5cccnc5c34)cc21] 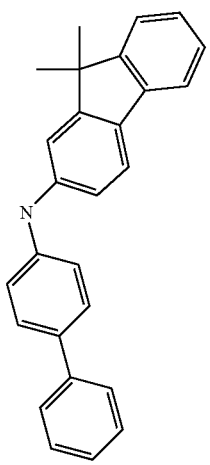 [SMILES: CC1(C)c2ccccc2-c2ccc(Nc3ccc(-c4ccccc4)cc3)cc21]

-continued
3-11 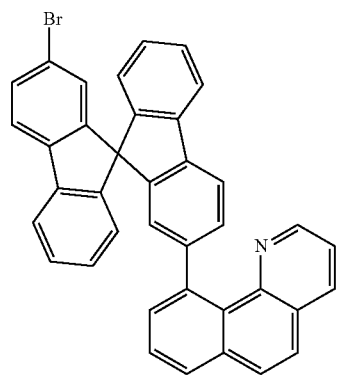 [SMILES: Brc1ccc2c(c1)C1(c3ccccc3-2)c2ccccc2-c2ccc(-c3cccc4ccc5cccnc5c34)cc21] 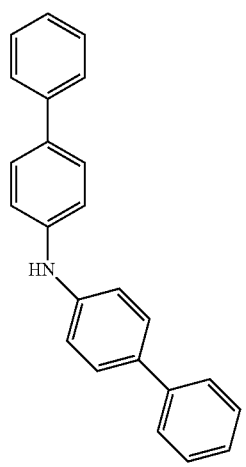
[102113-98-4]
3-12 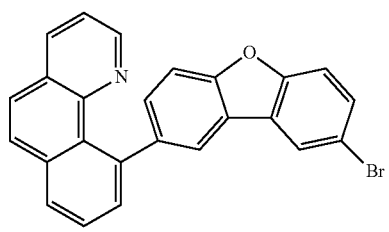 [SMILES: Brc1ccc2oc3ccc(-c4cccc5ccc6cccnc6c45)cc3c2c1] 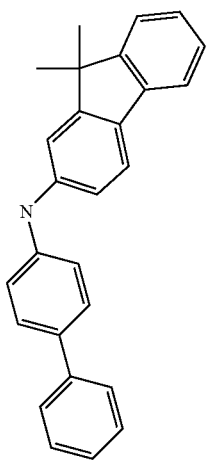 [SMILES: CC1(C)c2ccccc2-c2ccc(Nc3ccc(-c4ccccc4)cc3)cc21]
3-13 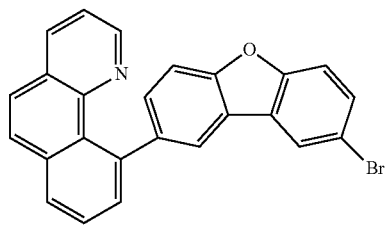 [SMILES: Brc1ccc2oc3ccc(-c4cccc5ccc6cccnc6c45)cc3c2c1] 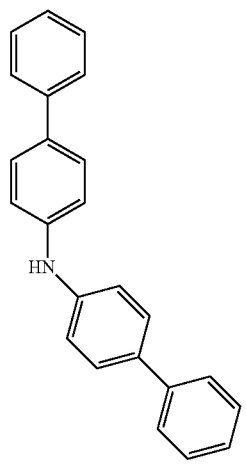
[102113-98-4]

-continued
3-14
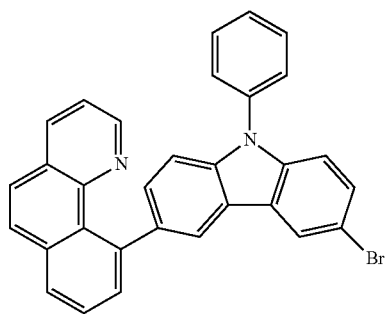 [SMILES: Brc1ccc2c(c1)c1cc(-c3cccc4ccc5cccnc5c34)ccc1n2-c1ccccc1]
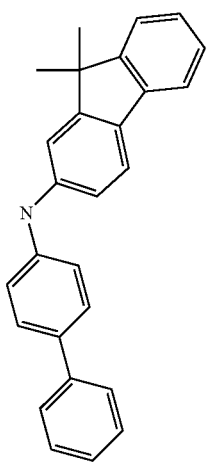 [SMILES: CC1(C)c2ccccc2-c2ccc(Nc3ccc(-c4ccccc4)cc3)cc21]
3-15
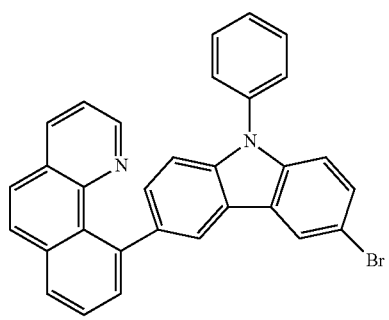 [SMILES: Brc1ccc2c(c1)c1cc(-c3cccc4ccc5cccnc5c34)ccc1n2-c1ccccc1]
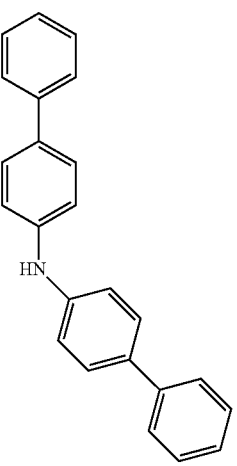
[102113-98-4]
3-16
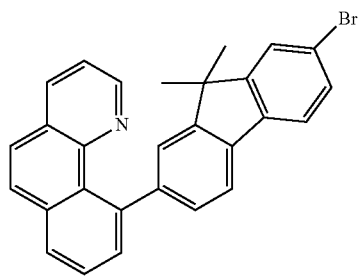 [SMILES: CC1(C)c2cc(Br)ccc2-c2ccc(-c3cccc4ccc5cccnc5c34)cc21]
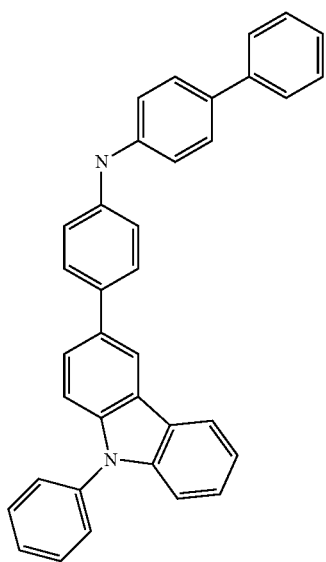 [SMILES: c1ccc(-c2ccc(Nc3ccc(-c4ccc5c(c4)c4ccccc4n5-c4ccccc4)cc3)cc2)cc1]

| | | |
|---|---|---|
| 3-17 | 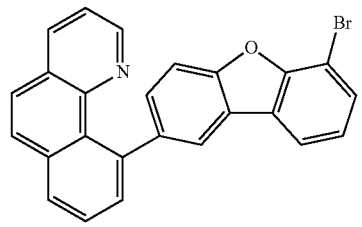 [SMILES: Brc1cccc2c1oc1ccc(-c3cccc4ccc5cccnc5c34)cc12] | 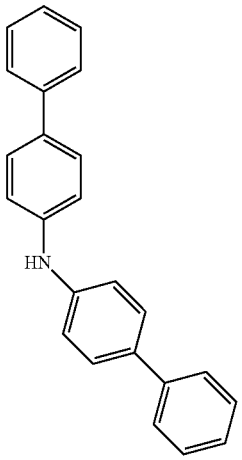[102113-98-4] |
| 3-18 | 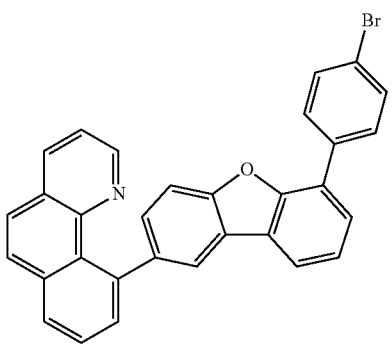 [SMILES: Brc1ccc(-c2cccc3c2oc2ccc(-c4cccc5ccc6cccnc6c45)cc23)cc1] | 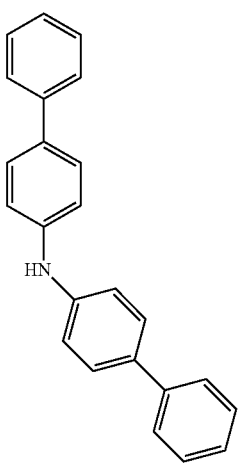[102113-98-4] |
| | Product | Yield |
| 3-2 | 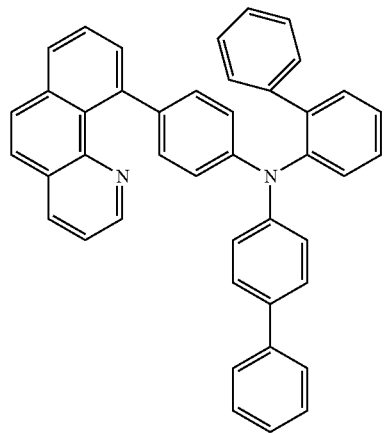 [SMILES: c1ccc(-c2ccc(N(c3ccc(-c4cccc5ccc6cccnc6c45)cc3)c3ccccc3-c3ccccc3)cc2)cc1] | 65% |

| | | |
|---|---|---|
| 3-3 | 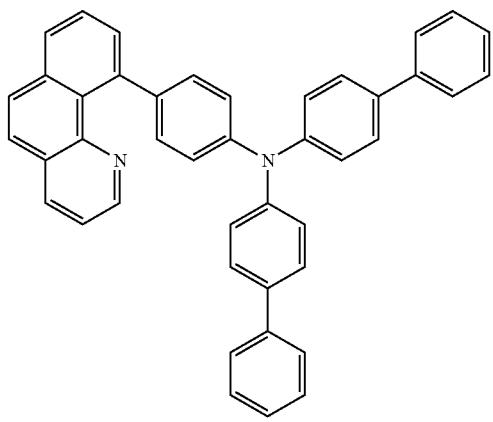 [SMILES: c1ccc(-c2ccc(N(c3ccc(-c4ccccc4)cc3)c3ccc(-c4cccc5ccc6cccnc6c45)cc3)cc2)cc1] | 75% |
| 3-4 | 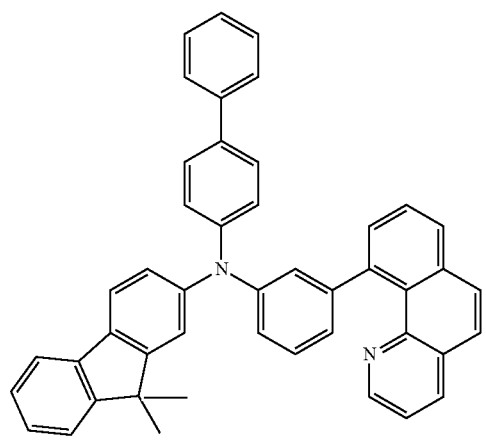 | 65% |
| 3-5 | 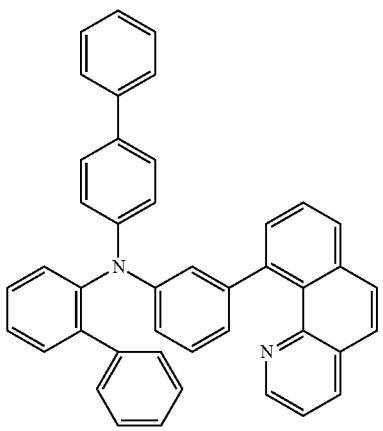 [SMILES: c1ccc(-c2ccc(N(c3cccc(-c4cccc5ccc6cccnc6c45)c3)c3ccccc3-c3ccccc3)cc2)cc1] | 55% |

| 3-6 | 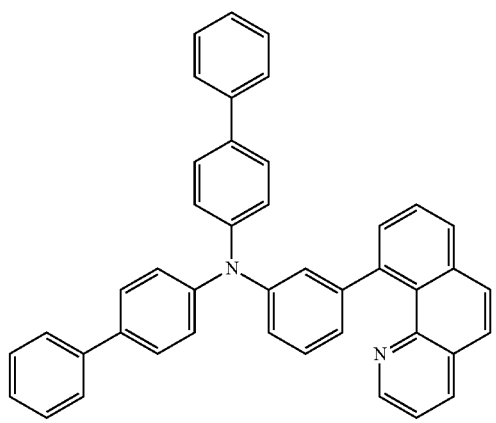 [SMILES: c1ccc(-c2ccc(N(c3ccc(-c4ccccc4)cc3)c3cccc(-c4cccc5ccc6cccnc6c45)c3)cc2)cc1] | 74% |
| 3-7 | 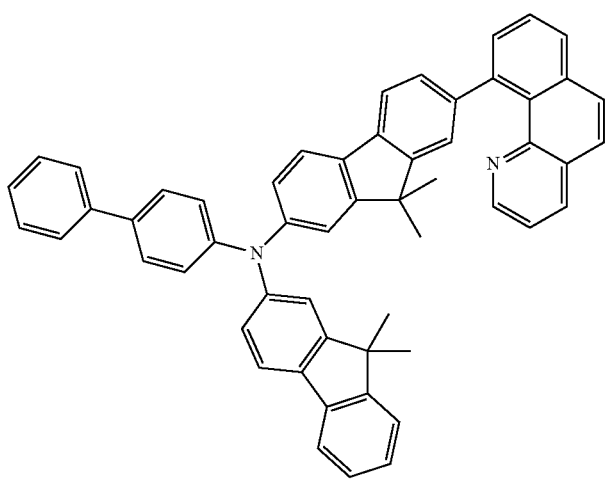 [SMILES: CC1(C)c2ccccc2-c2ccc(N(c3ccc(-c4ccccc4)cc3)c3ccc4c(c3)C(C)(C)c3cc(-c5cccc6ccc7cccnc7c56)ccc3-4)cc21] | 62% |
| 3-8 | 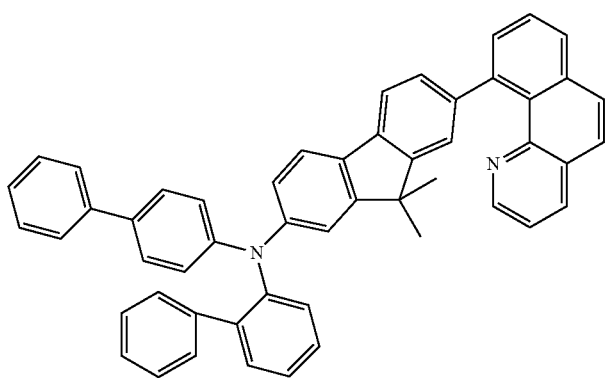 [SMILES: CC1(C)c2cc(-c3cccc4ccc5cccnc5c34)ccc2-c2ccc(N(c3ccc(-c4ccccc4)cc3)c3ccccc3-c3ccccc3)cc21] | 55% |

3-9 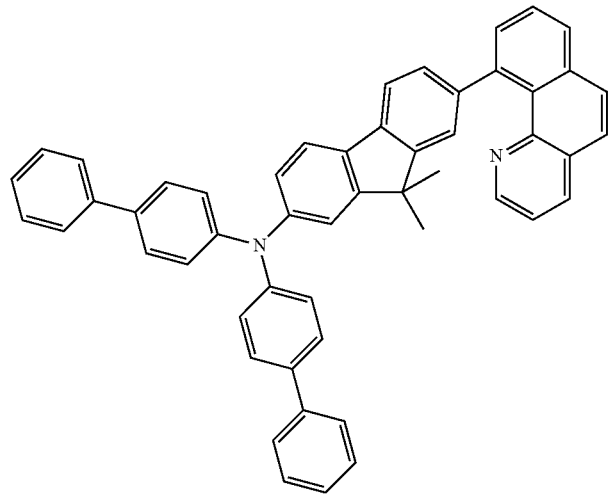 [SMILES: CC1(C)c2cc(-c3cccc4ccc5cccnc5c34)ccc2-c2ccc(N(c3ccc(-c4ccccc4)cc3)c3ccc(-c4ccccc4)cc3)cc21] 64%
3-10 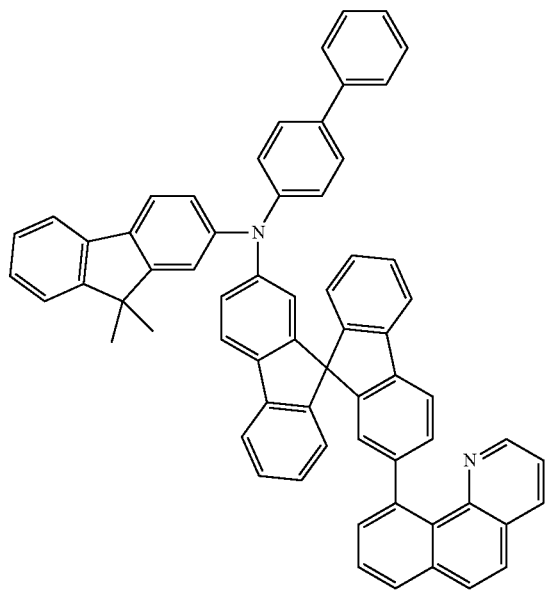 [SMILES: CC1(C)c2ccccc2-c2ccc(N(c3ccc(-c4ccccc4)cc3)c3ccc4c(c3)C3(c5ccccc5-c5ccc(-c6cccc7ccc8cccnc8c67)cc53)c3ccccc3-4)cc21] 52%

3-11 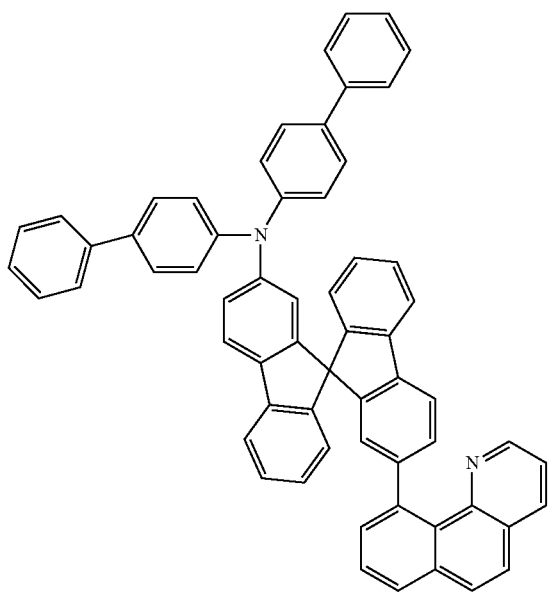 [SMILES: c1ccc(-c2ccc(N(c3ccc(-c4ccccc4)cc3)c3ccc4c(c3)C3(c5ccccc5-c5ccc(-c6cccc7ccc8cccnc8c67)cc53)c3ccccc3-4)cc2)cc1] 44%
3-12 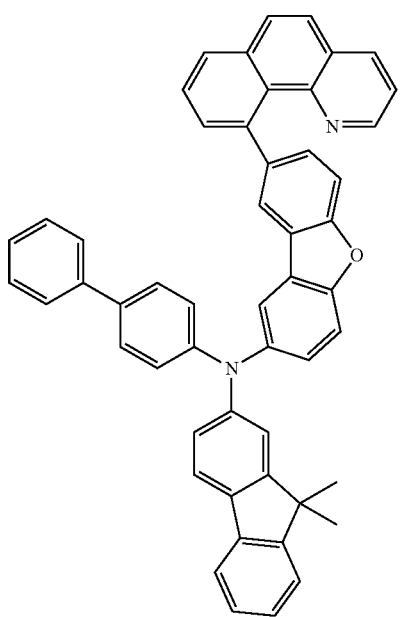 [SMILES: CC1(C)c2ccccc2-c2ccc(N(c3ccc(-c4ccccc4)cc3)c3ccc4oc5ccc(-c6cccc7ccc8cccnc8c67)cc5c4c3)cc21] 62%

| 3-13 | 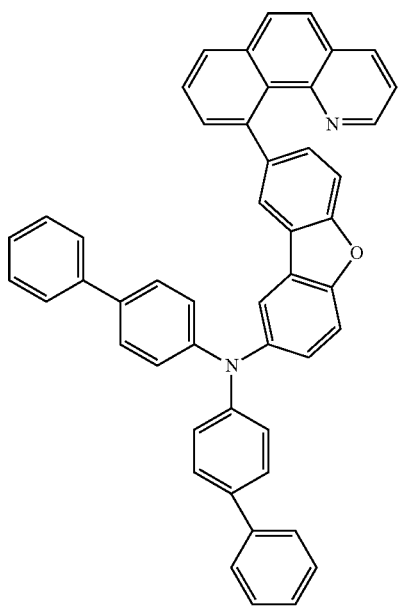 [SMILES: c1ccc(-c2ccc(N(c3ccc(-c4ccccc4)cc3)c3ccc4oc5ccc(-c6cccc7ccc8cccnc8c67)cc5c4c3)cc2)cc1] | 64% |
| 3-14 | 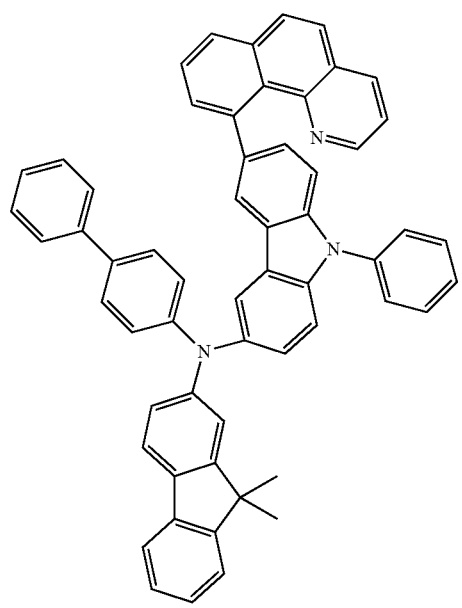 [SMILES: CC1(C)c2ccccc2-c2ccc(N(c3ccc(-c4ccccc4)cc3)c3ccc4c(c3)c3cc(-c5cccc6ccc7cccnc7c56)ccc3n4-c3ccccc3)cc21] | 62% |

3-15 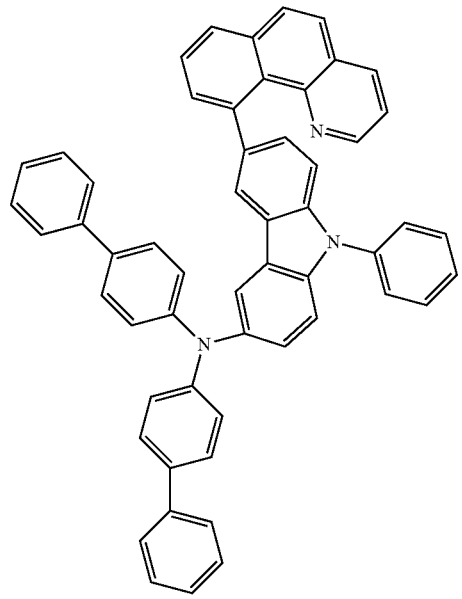 [SMILES: c1ccc(-c2ccc(N(c3ccc(-c4ccccc4)cc3)c3ccc4c(c3)c3cc(-c5cccc6ccc7cccnc7c56)ccc3n4-c3ccccc3)cc2)cc1] 64%
3-16 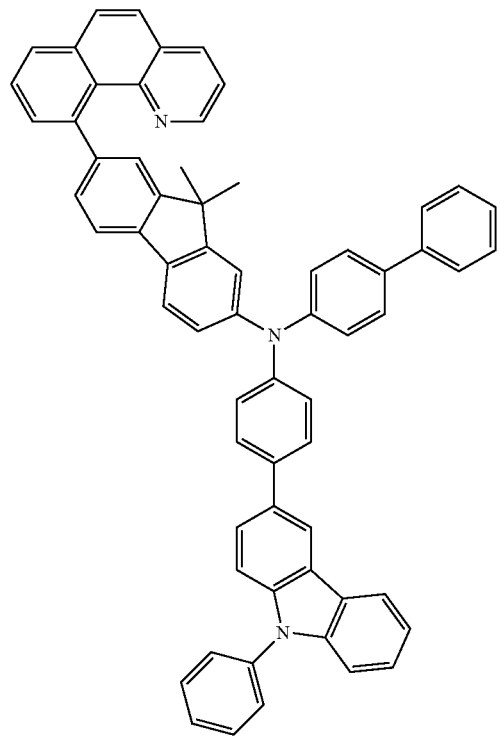 [SMILES: CC1(C)c2cc(-c3cccc4ccc5cccnc5c34)ccc2-c2ccc(N(c3ccc(-c4ccccc4)cc3)c3ccc(-c4ccc5c(c4)c4ccccc4n5-c4ccccc4)cc3)cc21] 76%

| | | |
|---|---|---|
| 3-17 | 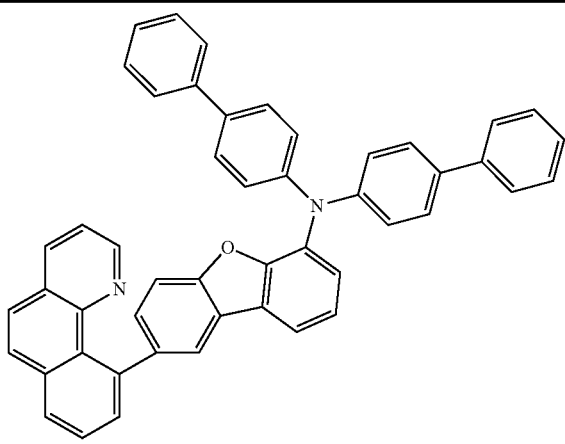 | 64% |
| 3-18 | 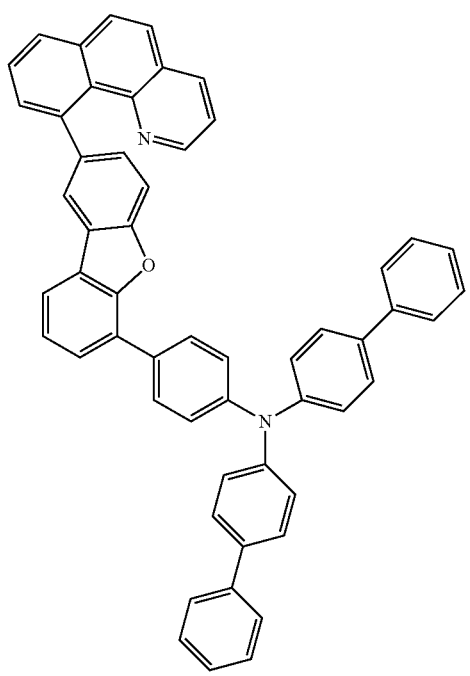 [SMILES: c1ccc(-c2ccc(N(c3ccc(-c4ccccc4)cc3)c3ccc(-c4cccc5c4oc4ccc(-c6cccc7ccc8cccnc8c67)cc45)cc3)cc2)cc1] | 64% |
Example 4-1
10-Benzo[h]quinolin-10-yl-12,12-dimethyl-10,12-dihydro-10-azaindeno[2,1-b]fluorene
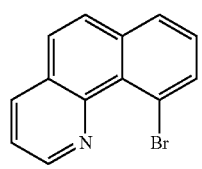 +
-continued
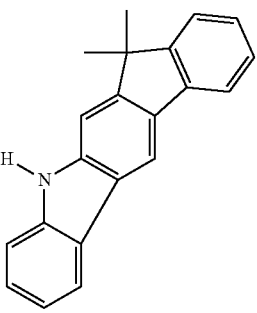 $\xrightarrow{\text{Ullmann reaction}}$

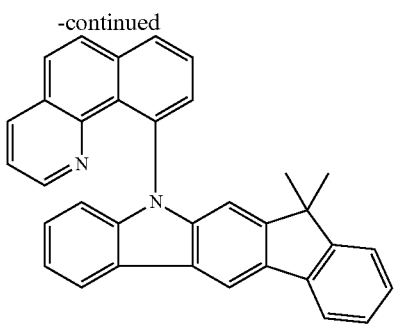

30 g (116 mmol) of 10-bromobenzo[h]quinoline, 32 g (116 mmol) of 2,12-dimethyl-10-phenyl-10,12-dihydro-10-azaindeno[2,1-b]fluorene, 32 g (232 mmol) of potassium carbonate, 2.6 g (11.6 mmol) of 1,3-di(2-pyridyl)-1,3-propanedione and 2.2 (11.6 mmol) of copper iodide are initially charged in 1000 mL of DMF. The solution is degassed, saturated with N₂ and heated to 100° C. for 60 h. Thereafter, water and toluene are added, the phases are separated, and the organic phase is washed twice with water and dried over Na₂SO₄ and concentrated by rotary evaporation. After the crude product has been filtered through silica gel with toluene, the remaining residue is recrystallized from heptane/toluene and finally sublimed under high vacuum. The purity is 99.9%. The yield is 37 g (71% of theory).

In an analogous manner, the following compounds are prepared:

| | Reactant 1 | Reactant 2 |
|---|---|---|
| 4-2 | 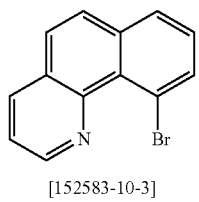 [SMILES: Brc1cccc2ccc3cccnc3c12]<br>[152583-10-3] | 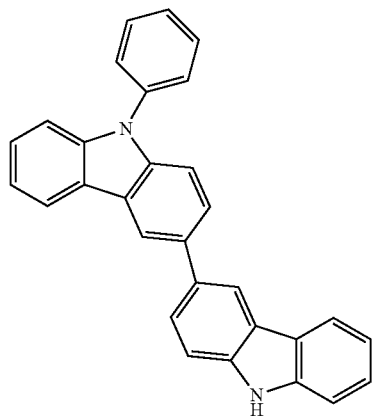<br>[1060735-14-9] |
| 4-3 | 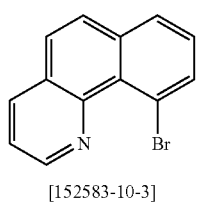 [SMILES: Brc1cccc2ccc3cccnc3c12]<br>[152583-10-3] | 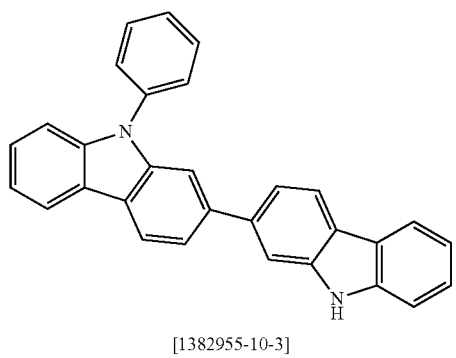 [SMILES: c1ccc(-n2c3ccccc3c3ccc(-c4ccc5c(c4)[nH]c4ccccc45)cc32)cc1]<br>[1382955-10-3] |
| 4-4 | 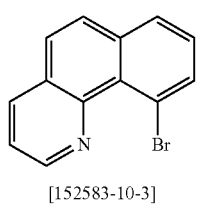 [SMILES: Brc1cccc2ccc3cccnc3c12]<br>[152583-10-3] | 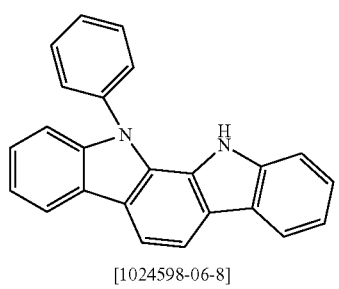 [SMILES: c1ccc(-n2c3ccccc3c3ccc4c5ccccc5[nH]c4c32)cc1]<br>[1024598-06-8] |

| | | |
|---|---|---|
| 4-5 | 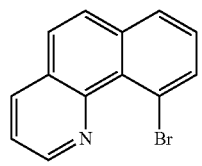 [152583-10-3] | 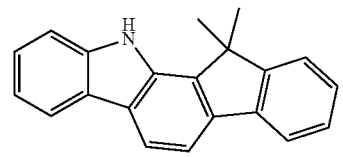 [1329054-41-2] |
| 4-6 | 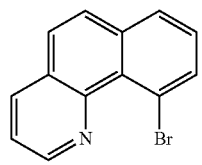 [152583-10-3] | 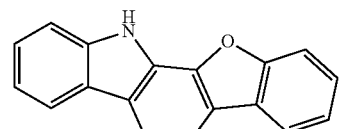 [1338919-70-2] |
| 4-7 | 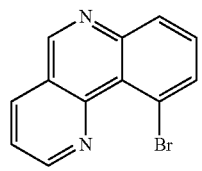 [66693-79-6] | 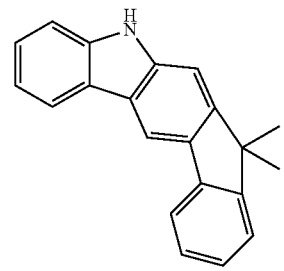 [1257220-47-5] |
| 4-8 | 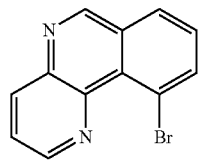 [66693-82-1] | 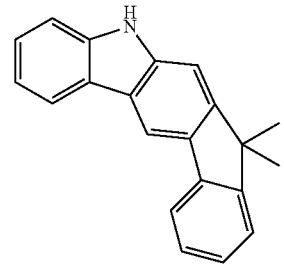 [1257220-47-5] |
| 4-9 | 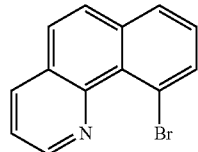 [1114904-98-1] | [1257220-47-5] |
| 4-10 | 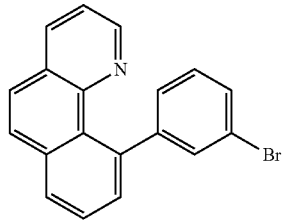 [SMILES: Brc1cccc(-c2cccc3ccc4cccnc4c23)c1] | 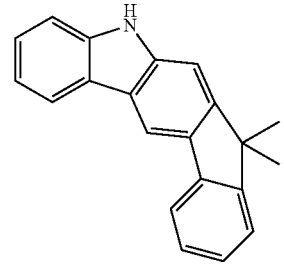 [1257220-47-5] |

-continued
| 4-11 | 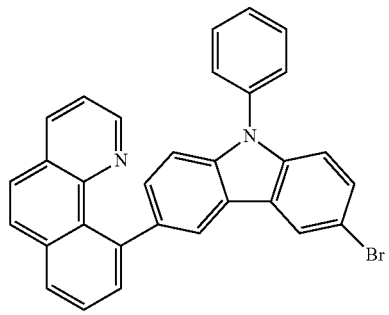 [SMILES: Brc1ccc2c(c1)c1cc(-c3cccc4ccc5cccnc5c34)ccc1n2-c1ccccc1] | 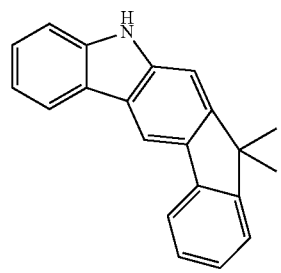
[1257220-47-5] |
|---|---|---|
| | Product | Yield |
| 4-2 | 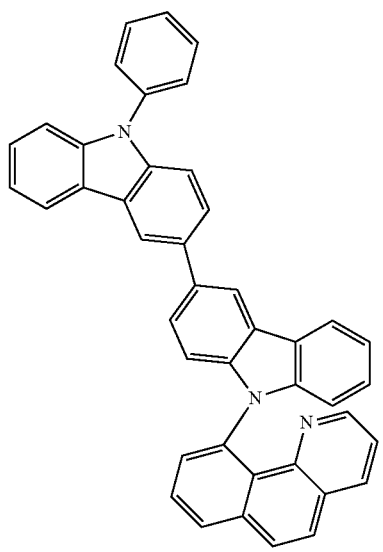 [SMILES: c1ccc(-n2c3ccccc3c3cc(-c4ccc5c(c4)c4ccccc4n5-c4cccc5ccc6cccnc6c45)ccc32)cc1] | 64% |
| 4-3 | 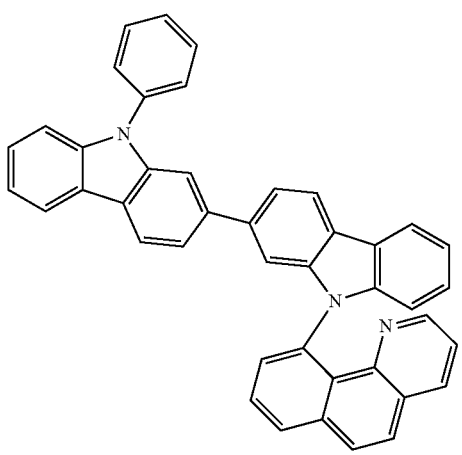 [SMILES: c1ccc(-n2c3ccccc3c3ccc(-c4ccc5c6ccccc6n(-c6cccc7ccc8cccnc8c67)c5c4)cc32)cc1] | 60% |
| 4-4 | 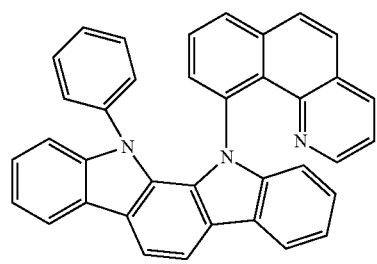 [SMILES: c1ccc(-n2c3ccccc3c3ccc4c5ccccc5n(-c5cccc6ccc7cccnc7c56)c4c32)cc1] | 69% |

| | | |
|---|---|---|
| 4-5 | 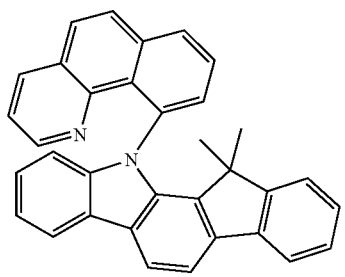 [SMILES: CC1(C)c2ccccc2-c2ccc3c4ccccc4n(-c4cccc5ccc6cccnc6c45)c3c21] | 73% |
| 4-6 | 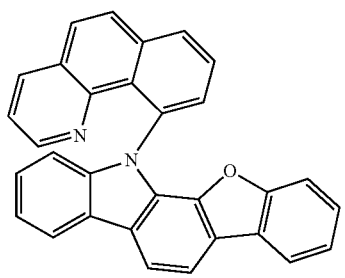 [SMILES: c1cnc2c(c1)ccc1cccc(-n3c4ccccc4c4ccc5c6ccccc6oc5c43)c12] | 67% |
| 4-7 | 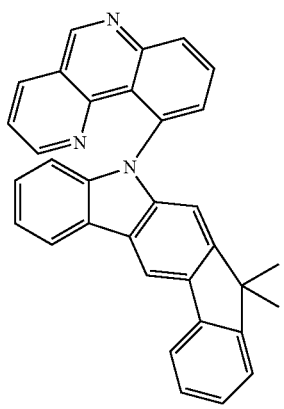 [SMILES: CC1(C)c2ccccc2-c2cc3c4ccccc4n(-c4cccc5ncc6cccnc6c45)c3cc21] | 67% |
| 4-8 | 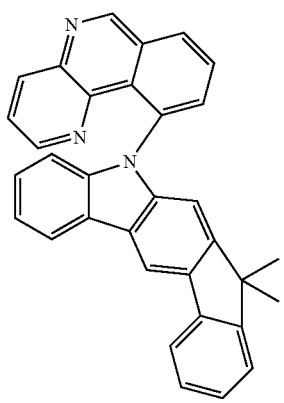 [SMILES: CC1(C)c2ccccc2-c2cc3c4ccccc4n(-c4cccc5cnc6cccnc6c45)c3cc21] | 63% |

| | | |
|---|---|---|
| 4-9 | 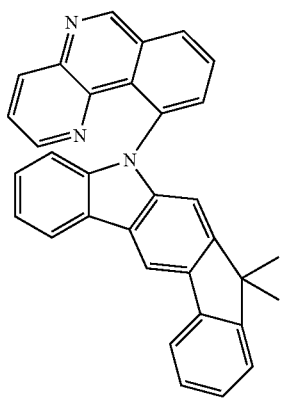 [SMILES: CC1(C)c2ccccc2-c2cc3c4ccccc4n(-c4cccc5cnc6cccnc6c45)c3cc21] | 62% |
| 4-10 | 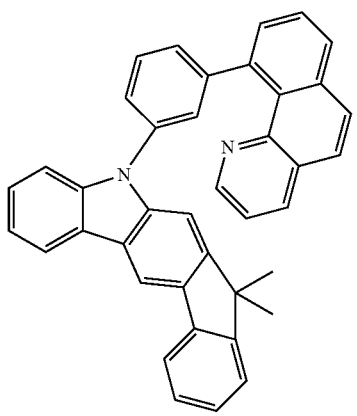[1257220-47-5] | 72% |
| 4-11 | 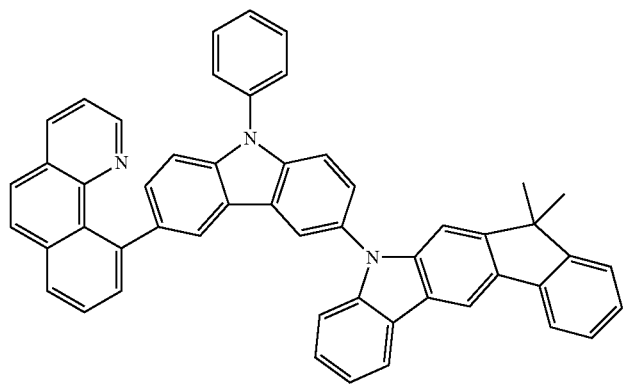 [SMILES: CC1(C)c2ccccc2-c2cc3c4ccccc4n(-c4ccc5c(c4)c4cc(-c6cccc7ccc8cccnc8c67)ccc4n5-c4ccccc4)c3cc21] | 59% |

Analogously, the following compounds are prepared with 58 mmol of carbazole derivative:
| | Reactant 1 | Reactant 2 |
|---|---|---|
| 4-12 | | |
| 4-13 | | |
| 4-14 | | |
| 4-15 | | |
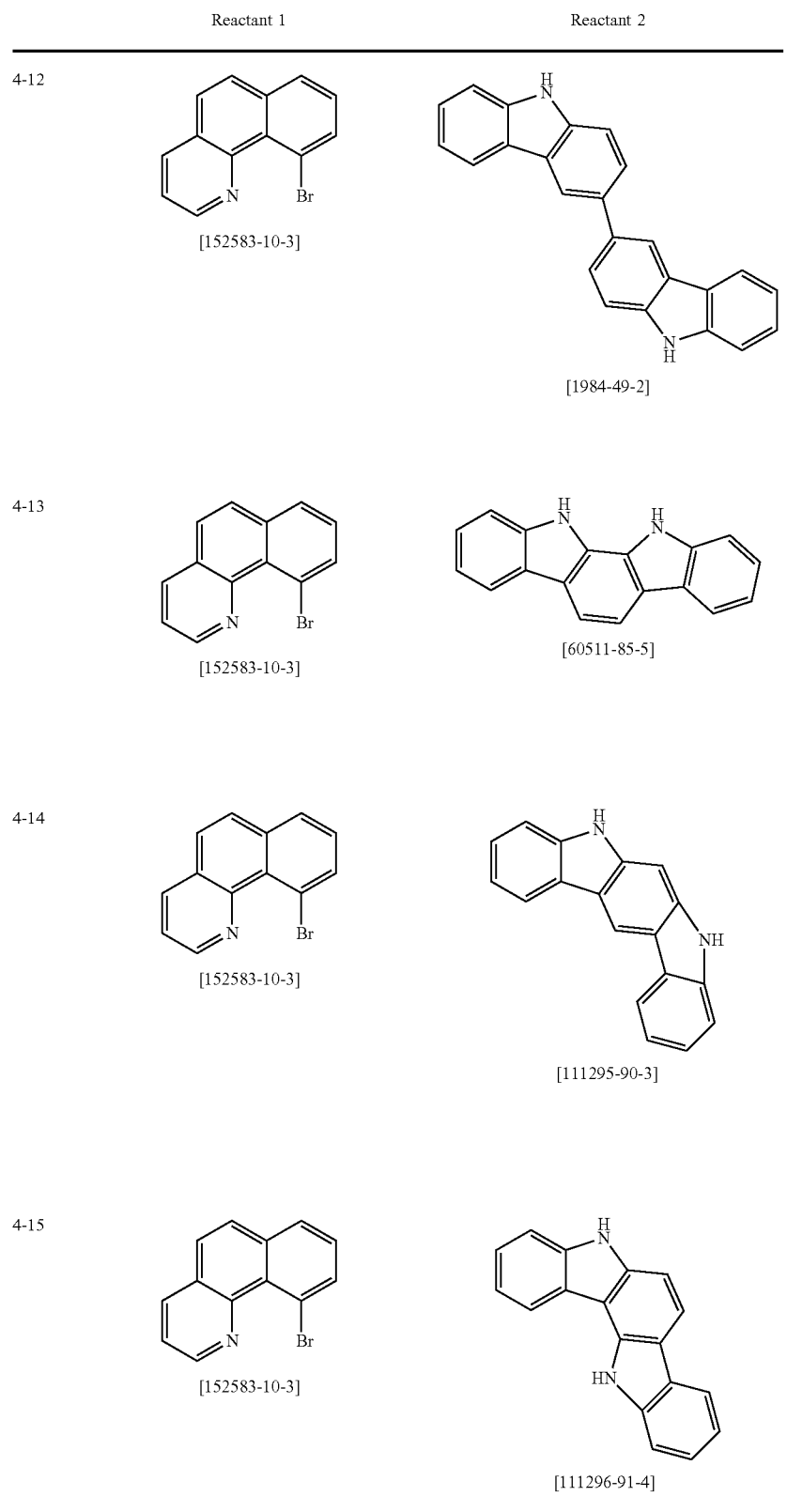

| Product | Yield |
|---|---|
| 4-12 [structure] | 67% |
| 4-13 [structure] | 72% |
| 4-14 [structure] | 78% |

| | | |
|---|---|---|
| 4-15 | 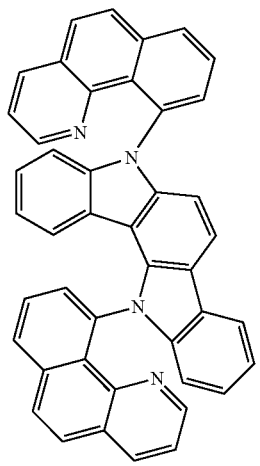 [SMILES: c1cnc2c(c1)ccc1cccc(-n3c4ccccc4c4c3ccc3c5ccccc5n(-c5cccc6ccc7cccnc7c56)c34)c12] | 70% |

B) Device Examples

OLEDs of the invention and OLEDs according to the prior art are produced by a general method according to WO 04/058911, which is adapted to the circumstances described here (variation in layer thickness, materials).

In inventive examples I1 to I6 and in reference example C1 which follow, the data of various OLEDs are presented. Substrates used are glass plates coated with structured ITO (indium tin oxide) of thickness 50 nm. The OLEDs basically have the following layer structure: substrate/p-doped hole transport layer HIL1/hole transport layer HTL/p-doped hole transport layer HIL2/hole transport layer EBL/emission layer EML/electron transport layer ETL/electron injection layer EIL and finally a cathode. The cathode is formed by an aluminum layer of thickness 100 nm. The materials required for production of the OLEDs are shown in table 1, and the structure of the various electronic devices produced in table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by coevaporation. Details given in such a form as H1:TEG (10%) mean here that the material H1 is present in the layer in a proportion by volume of 90% and TEG in a proportion of 10%. In an analogous manner, the electron transport layer or the hole injection layers may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian radiation characteristics, and also the lifetime are determined. The electroluminescence spectra are determined at a luminance of 1000 cd/m$^2$, and the CIE 1931 x and y color coordinates are calculated therefrom. The parameter EQE @2 mA/cm$^2$ refers to the external quantum efficiency at a current density of 2 mA/cm$^2$. LD80 @10 000 cd/m$^2$, reported in hours, is the time by which the OLED has dropped to 80% of the starting intensity, i.e. to 8000 cd/m$^2$, at constant current.

TABLE 1

Structures of the materials used

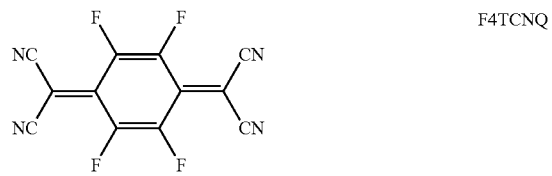

F4TCNQ

TABLE 1-continued
Structures of the materials used
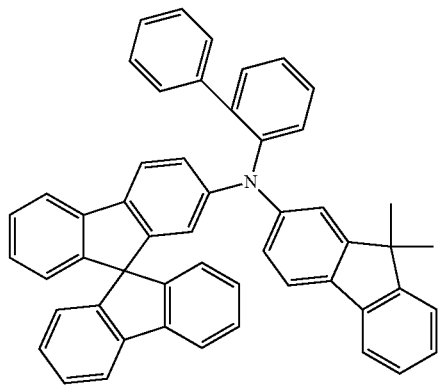 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HIM
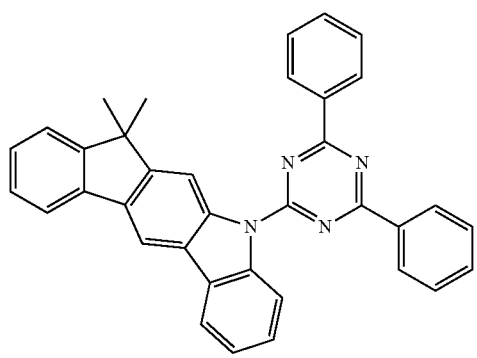 [SMILES: CC1(C)c2ccccc2-c2cc3c4ccccc4n(-c4nc(-c5ccccc5)nc(-c5ccccc5)n4)c3cc21]
H1
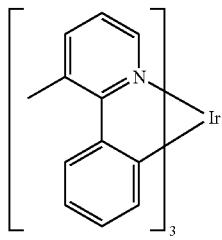
TEG
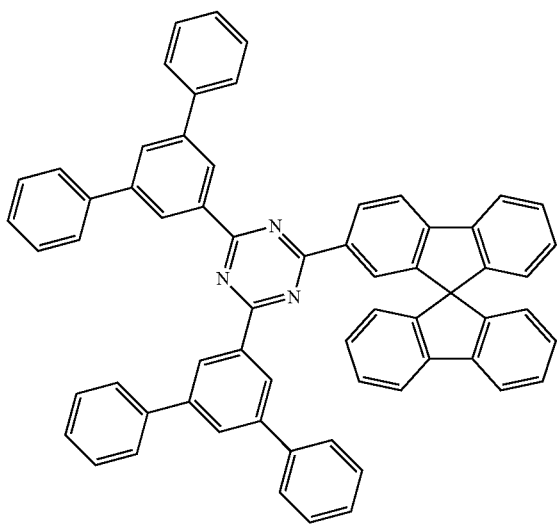 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM TABLE 1-continued
Structures of the materials used
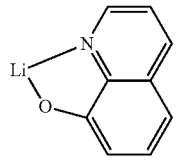
LiQ
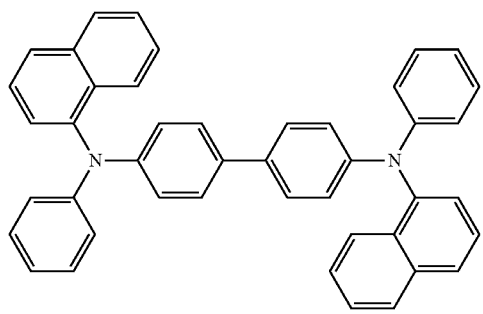 [SMILES: c1ccc(N(c2ccc(-c3ccc(N(c4ccccc4)c4cccc5ccccc45)cc3)cc2)c2cccc3ccccc23)cc1]
NPB
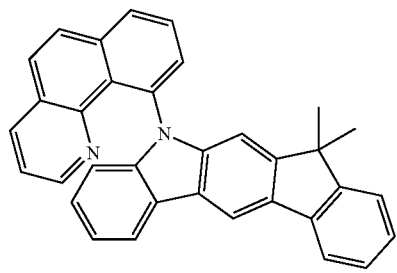 [SMILES: CC1(C)c2ccccc2-c2cc3c4ccccc4n(-c4cccc5ccc6cccnc6c45)c3cc21]
HTM1
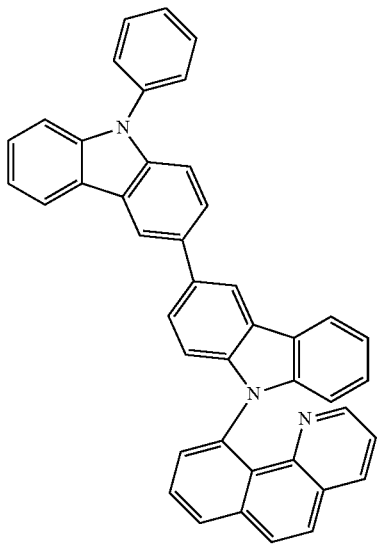 [SMILES: c1ccc(-n2c3ccccc3c3cc(-c4ccc5c(c4)c4ccccc4n5-c4cccc5ccc6cccnc6c45)ccc32)cc1]
HTM2

TABLE 1-continued
Structures of the materials used
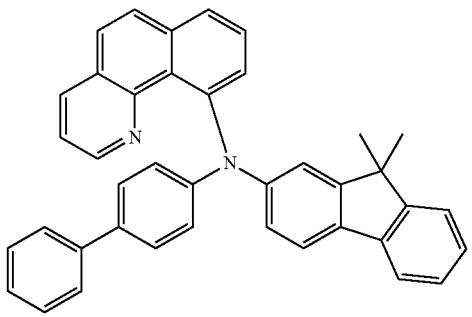 [SMILES: CC1(C)c2ccccc2-c2ccc(N(c3ccc(-c4ccccc4)cc3)c3cccc4ccc5cccnc5c34)cc21]
HTM3
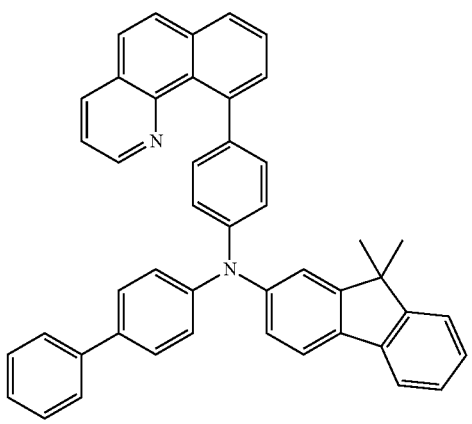 [SMILES: CC1(C)c2ccccc2-c2ccc(N(c3ccc(-c4ccccc4)cc3)c3ccc(-c4cccc5ccc6cccnc6c45)cc3)cc21]
HTM4
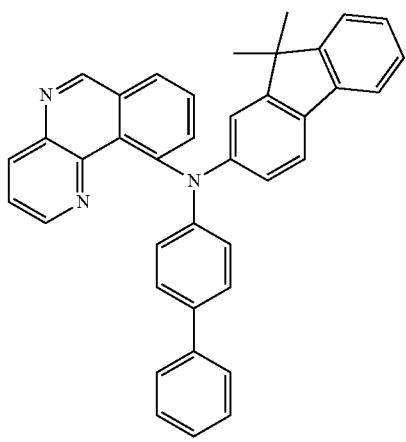 [SMILES: CC1(C)c2ccccc2-c2ccc(N(c3ccc(-c4ccccc4)cc3)c3cccc4cnc5cccnc5c34)cc21]
HTM5
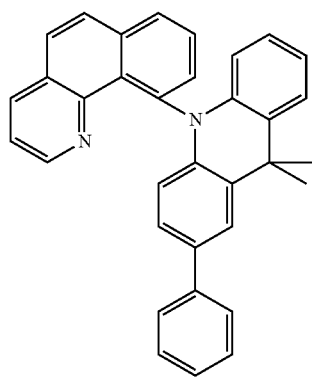 [SMILES: CC1(C)c2ccccc2N(c2cccc3ccc4cccnc4c23)c2ccc(-c3ccccc3)cc21]
HTM6

TABLE 2

| | | HTL | | EBL | EML | | EIL |
| Ex. | HIL1 Thickness/nm | Thickness/nm | HIL2 Thickness/nm | Thickness/nm | Thickness/nm | ETL Thickness/nm | Thickness/nm |
|---|---|---|---|---|---|---|---|
| C1 | HIM1:F4TCNQ(3%) 20 nm | HIM1 210 nm | NPB:F4TCNQ(3%) 20 nm | NPB 20 nm | H1:TEG(10%) 30 nm | ETM(50%):LiQ(50%) 40 nm | LiQ 1 nm |
| I1 | HIM1:F4TCNQ(3%) 20 nm | HIM1 210 nm | HTM1:F4TCNQ(3%) 20 nm | HTM1 20 nm | H1:TEG(10%) 30 nm | ETM(50%):LiQ(50%) 40 nm | LiQ 1 nm |
| I2 | HTM2:F4TCNQ(3%) 20 nm | HTM2 210 nm | NPB:F4TCNQ(3%) 20 nm | NPB 20 nm | H1:TEG(10%) 30 nm | ETM(50%):LiQ(50%) 40 nm | LiQ 1 nm |
| I3 | HTM3:F4TCNQ(3%) 20 nm | HTM3 210 nm | NPB:F4TCNQ(3%) 20 nm | NPB 20 nm | H1:TEG(10%) 30 nm | ETM(50%):LiQ(50%) 40 nm | LiQ 1 nm |
| I4 | HTM4:F4TCNQ(3%) 20 nm | HTM4 210 nm | NPB:F4TCNQ(3%) 20 nm | NPB 20 nm | H1:TEG(10%) 30 nm | ETM(50%):LiQ(50%) 40 nm | LiQ 1 nm |
| I5 | HTM5:F4TCNQ(3%) 20 nm | HTM5 210 nm | NPB:F4TCNQ(3%) 20 nm | NPB 20 nm | H1:TEG(10%) 30 nm | ETM(50%):LiQ(50%) 40 nm | LiQ 1 nm |
| I6 | HIM1:F4TCNQ(3%) 20 nm | HIM1 210 nm | HTM6:F4TCNQ(3%) 20 nm | HTM6 20 nm | H1:TEG(10%) 30 nm | ETM(50%):LiQ(50%) 40 nm | LiQ 1 nm |

The examples which follow show the use of the compounds HTM1 to HTM6 of the invention as hole transport materials in a phosphorescent OLED. The emitting layer is formed from the materials TEG1 as emitter material and H1 as matrix material.

Device Examples 1 and 2

A green-phosphorescing reference device C1 was produced and compared with the devices I1 and I2 of the invention. The reference device C1 at a current density of 2 mA/cm$^2$ has an external quantum efficiency of 11.7% and a lifetime (LD80 @10 000 cd/m$^2$) of 90 h. By comparison, the device I1 of the invention has a better external quantum efficiency of 15.5% and a better LD80 at 10 000 cd/m$^2$ of 120 h. The device I2 of the invention has a quantum efficiency of 15.8% and a lifetime of 100 h.

Device Examples 3 to 6

A green-phosphorescing reference device C1 was produced and compared with the devices I3 to I6 of the invention. The reference device C1 at a current density of 2 mA/cm$^2$ has an external quantum efficiency of 11.7%. By comparison, the devices I3-I6 of the invention have a better external quantum efficiency of 13.3% (I3), 14.2% (I4), 13.7% (I5) and 12.8% (I6).

The examples show that the compounds of the invention are of very good suitability for use in OLEDs, especially for use as hole-transporting materials. However, the use is not limited to this function. The materials are also suitable, for example, for use as matrix materials in the emitting layer.

The invention claimed is:

1. A compound of formulae (I-1), (I-2) or (I-3)

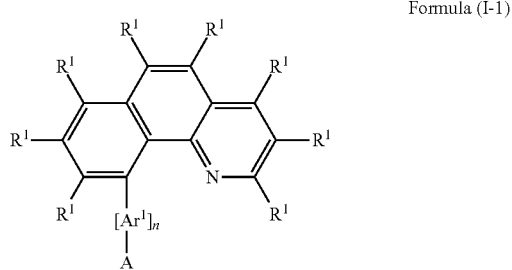

Formula (I-1)

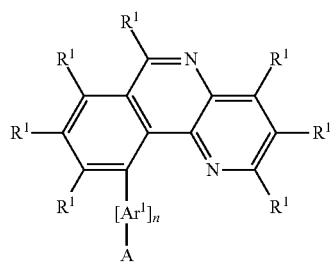

Formula (I-2)

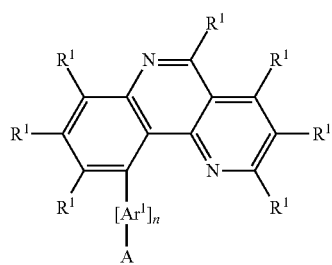

Formula (I-3)

where:
A is a group (A-1)

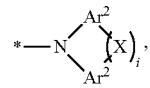

Formula (A-1)

which are bonded via the bond marked *,
Ar$^1$ is the same or different at each instance and is selected from benzene, pyridine, pyrimidine, triazine, naphthalene, quinoline, fluorene, spirobifluorene, indenofluorene, carbazole, indenocarbazole, indolocarbazole, dibenzofuran and dibenzothiophene, each of which may be substituted by one or more R$^1$ radicals;
Ar$_2$ is the same or different at each instance and is selected from benzene, biphenyl, terphenyl, quaterphenyl, pyridine, pyrimidine, pyrazine, pyridazine, triazine, naphthalene, quinoline, fluorene, spirobifluorene, indenofluorene, carbazole, indenocarbazole, indolocarbazole, dibenzofuran or dibenzothiophene, each of which may be substituted by one or more R$^1$ radicals;

X is the same or different at each instance and is a single bond or a group selected from $BR^2$, $C(R^2)_2$, —$C(R^2)_2$—$C(R^2)_2$—, —$C(R^2)$=$C(R^2)$—, —$C(R^2)_2$—O—, —$C(R^2)_2$—$NR^2$—, $Si(R^2)_2$, C=O, $NR^2$, $PR^2$, P(=O)$R^2$, O, S, S=O and $SO_2$;

$R^1$, $R^2$ are the same or different at each instance and are H, D, F, C(=O)$R^3$, CN, $Si(R^3)_3$, $N(R^3)_2$, P(=O)$(R^3)_2$, $OR^3$, S(=O)$R^3$, S(=O)$_2R^3$, a straight-chain alkyl or alkoxy group having 1 to 20 carbon atoms or a branched or cyclic alkyl or alkoxy group having 3 to 20 carbon atoms or an alkenyl or alkynyl group having 2 to 20 carbon atoms, where the abovementioned groups may each be substituted by one or more $R^3$ radicals and where one or more $CH_2$ groups in the abovementioned groups may be replaced by —$R^3C$=$CR^3$—, —C≡C—, $Si(R^3)_2$, C=O, C=$NR^3$, —C(=O)O—, —C(=O)$NR^3$—, $NR^3$, P(=O)$(R^3)$, —O—, —S—, SO or $SO_2$, or an aromatic or heteroaromatic ring system which has 5 to 30 aromatic ring atoms and may be substituted by one or more $R^3$ radicals; two or more $R^2$ radicals may be joined to one another and form a ring;

$R^3$ is the same or different at each instance and is H, D, F, C(=O)$R^4$, CN, $Si(R^4)_3$, $N(R^4)_2$, P(=O)$(R^4)_2$, $OR^4$, S(=O)$R^4$, S(=O)$_2R^4$, a straight-chain alkyl or alkoxy group having 1 to 20 carbon atoms or a branched or cyclic alkyl or alkoxy group having 3 to 20 carbon atoms or an alkenyl or alkynyl group having 2 to 20 carbon atoms, where the abovementioned groups may each be substituted by one or more $R^4$ radicals and where one or more $CH_2$ groups in the abovementioned groups may be replaced by —$R^4C$=$CR^4$—, —C≡C—, $Si(R^4)_2$, C=O, C=$NR^4$, —C(=O)O—, —C(=O)$NR^4$—, $NR^4$, P(=O)$(R^4)$, —O—, —S—, SO or $SO_2$, or an aromatic or heteroaromatic ring system which has 5 to 30 aromatic ring atoms and may be substituted by one or more $R^4$ radicals; two or more $R^3$ radicals may be joined to one another and form a ring;

$R^4$ is the same or different at each instance and is H, D, F, CN or an aliphatic, aromatic or heteroaromatic organic radical having 1 to 20 carbon atoms, in which one or more hydrogen atoms may also be replaced by D, F or CN; two or more $R^4$ substituents may be joined to one another and form a ring;

n is 0, 1, 2 or 3;

i is the same or different at each instance and is 0 or 1; and wherein the compound of formulae (I-1), (I-2) or (I-3) does not have any fused aryl or heteroaryl group having more than 10 aromatic ring atoms, as substituent $R^1$, $R^2$, $R^3$ and $R^4$.

2. A compound of claim 1, wherein n is 0.

3. A compound of claim 1, wherein X is the same or different at each instance and is selected from a single bond and a group selected from $C(R^2)_2$, C=O, $NR^2$, O or S.

4. A compound of claim 1, wherein the compound does not have any further arylamino group, any further bridged arylamino group or any further carbazole group in addition to the A group.

5. A process for preparing a compound of claim 1, comprising converting a compound of formulae (I-1), (I-2) or (I-3)

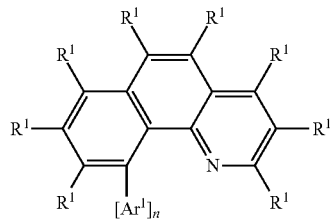
Formula (I-1)

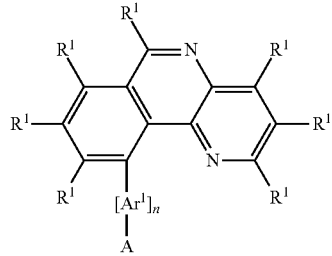
Formula (I-2)

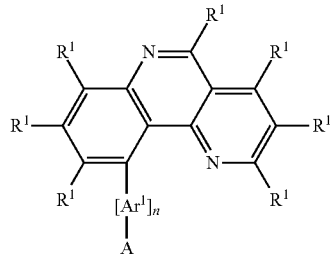
Formula (I-3)

in a coupling reaction,
where the variable groups and indices are as defined in claim 1,
and where Y is any reactive group.

6. An oligomer, polymer or dendrimer comprising one or more compounds of claim 1, wherein the bonds to the polymer, oligomer or dendrimer may be localized at any desired positions substituted by $R^1$ or $R^2$ in formulae (I-1), (I-2) or (I-3).

7. A formulation comprising at least one compound of claim 1, and at least one solvent.

8. An electronic device comprising anode, cathode and at least one organic layer, wherein the organic layer comprises at least one compound of claim 1.

9. The electronic device of claim 8, that is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes and organic electroluminescent devices.

10. The electronic device of claim 8, wherein the organic layer is an emitting layer, and the at least one compound of formulae (I-1), (I-2) or (I-3) is present as matrix material, and the electronic device is an organic electroluminescent device.

11. The electronic device of claim 8, wherein the organic layer is a hole transporting layer, and the at least one compound of formulae (I-1), (I-2) or (I-3) is present as a hole transport material, and the electronic device is an organic electroluminescent device.

12. The compound of claim 1, wherein the compound is a compound of formula (I-1).

13. The compound of claim 1, wherein
$R^1$ is the same or different at each instance and is H, D, F, CN, Si($R^3$)$_3$, N($R^3$)$_2$, a straight-chain alkyl or alkoxy group having 1 to 20 carbon atoms or a branched or cyclic alkyl or alkoxy group having 3 to 20 carbon atoms, optionally substituted by one or more $R^3$ radicals and where one or more CH$_2$ groups optionally replaced by —C≡C—, —$R^3$C═C$R^3$—, Si($R^3$)$_2$, C═O, C═N$R^3$, —N$R^3$—, —O—, —S—, —C(═O)O— or —C(═O)N$R^3$—, or an aromatic or heteroaromatic ring system having 5 to 20 aromatic ring atoms, each of which may be substituted by one or more $R^3$ radicals, $R^2$ is the same or different at each instance and is H, D, F, Si($R^3$)$_3$, a straight-chain alkyl or alkoxy group having 1 to 20 carbon atoms or a branched or cyclic alkyl or alkoxy group having 3 to 20 carbon atoms, optionally substituted by one or more $R^3$ radicals and where one or more CH$_2$ groups optionally replaced by —C≡C—, —$R^3$C═C$R^3$—, Si($R^3$)$_2$, C═O, C═N$R^3$, —N$R^3$—, —O—, —S—, —C(═O)O— or —C(═O)N$R^3$—, or an aromatic or heteroaromatic ring system having 5 to 20 aromatic ring atoms, each of which may be substituted by one or more $R^3$ radicals, $R^3$ is the same or different at each instance and is H, D, F, CN, Si($R^4$)$_3$, N($R^4$)$_2$, a straight-chain alkyl or alkoxy group having 1 to 20 carbon atoms or a branched or cyclic alkyl or alkoxy group having 3 to 20 carbon atoms, optionally substituted by one or more $R^4$ radicals and where one or more CH$_2$ groups is optionally replaced by —C≡C—, —$R^4$C═C$R^4$—, Si($R^4$)$_2$, C═O, C═N$R^4$, —N$R^4$—, —O—, —S—, —C(═O)O— or —C(═O)N$R^4$—, or an aromatic or heteroaromatic ring system having 5 to 20 aromatic ring atoms, each of which may be substituted by one or more $R^4$ radicals, and $R^4$ is the same or different at each instance and is H, D, F, CN or an aliphatic, aromatic or heteroaromatic organic radical having 1 to 20 carbon atoms, in which one or more hydrogen atoms may also be replaced by D, F or CN.

14. The compound of claim 1, wherein
i is 0.

15. A compound of formulae (I-1), (I-2) or (I-3)

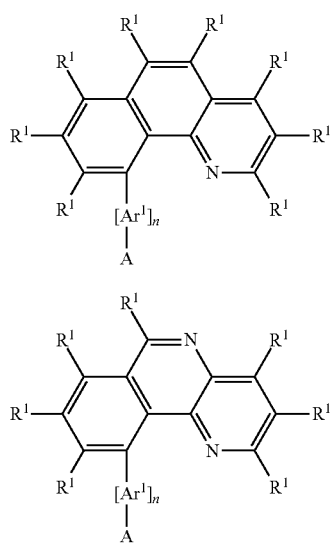

Formula (I-1)

Formula (I-2)

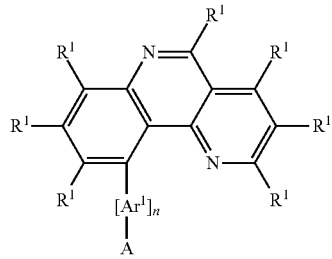

Formula (I-3)

where:
A is a group (A-1)

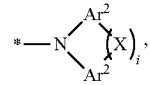

Formula (A-1)

which are bonded via the bond marked *,
in formula (A-1) index i=1,
$Ar^1$ is the same or different at each instance and is selected from benzene, pyridine, pyrimidine, triazine, naphthalene, quinoline, fluorene, spirobifluorene, indenofluorene, carbazole, indenocarbazole, indolocarbazole, dibenzofuran and dibenzothiophene, each of which may be substituted by one or more R1 radicals;
$Ar^2$ is the same or different at each instance and is selected from benzene, biphenyl, terphenyl, quaterphenyl, pyridine, pyrimidine, pyrazine, pyridazine, triazine, naphthalene, quinoline, fluorene, spirobifluorene, indenofluorene, carbazole, indenocarbazole, indolocarbazole, dibenzofuran or dibenzothiophene, each of which may be substituted by one or more R1 radicals; and i is 0 or 1,
X is a single bond;
$R^1$ are the same or different at each instance and are H, D, F, CN, Si($R^3$)$_3$, a straight-chain alkyl group having 1 to 20 carbon atoms or a branched or cyclic alkyl group having 3 to 20 carbon atoms, where the alkyl groups are optionally substituted by one or more $R^3$ radicals;
$R^2$ are the same or different at each instance and are H, D, F, C(═O)$R^3$, CN, Si($R^3$)$_3$, N($R^3$)$_2$, P(═O)($R^3$)$_2$, O$R^3$, S(═O)$R^3$, S(═O)$_2R^3$, a straight-chain alkyl or alkoxy group having 1 to 20 carbon atoms or a branched or cyclic alkyl or alkoxy group having 3 to 20 carbon atoms or an alkenyl or alkynyl group having 2 to 20 carbon atoms, where the abovementioned groups may each be substituted by one or more $R^3$ radicals and where one or more CH$_2$ groups in the abovementioned groups may be replaced by —$R^3$C═C$R^3$—, —C≡C—, Si($R^3$)$_2$, C═O, C═N$R^3$, —C(═O)O—, —C(═O)N$R^3$—, N$R^3$, P(═O)($R^3$), —O—, —S—, SO or SO$_2$, or an aromatic or heteroaromatic ring system which has 5 to 30 aromatic ring atoms and may be substituted by one or more $R^3$ radicals; two or more $R^2$ radicals may be joined to one another and form a ring;
$R^3$ is the same or different at each instance and is H, D, F, C(═O)$R^4$, CN, Si($R^4$)$_3$, N($R^4$)$_2$, P(═O)($R^4$)$_2$, O$R^4$, S(═O)$R^4$, S(═O)$_2R^4$, a straight-chain alkyl or alkoxy group having 1 to 20 carbon atoms or a branched or cyclic alkyl or alkoxy group having 3 to 20 carbon atoms or an alkenyl or alkynyl group having 2 to 20 carbon atoms, where the abovementioned groups may each be substituted by one or more $R^4$ radicals and where one or more $CH_2$ groups in the abovementioned groups may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, $SO$ or $SO_2$, or an aromatic or heteroaromatic ring system which has 5 to 30 aromatic ring atoms and may be substituted by one or more $R^4$ radicals; two or more $R^3$ radicals may be joined to one another and form a ring;

$R^4$ is the same or different at each instance and is H, D, F, CN or an aliphatic, aromatic or heteroaromatic organic radical having 1 to 20 carbon atoms, in which one or more hydrogen atoms may also be replaced by D, F or CN; two or more $R^4$ substituents may be joined to one another and form a ring; and n is 0, 1, 2 or 3.

* * * * *